(12) United States Patent
Holland et al.

(10) Patent No.: US 9,068,159 B2
(45) Date of Patent: Jun. 30, 2015

(54) BACTERIOPHAGE AND THEIR USES

(75) Inventors: Keith Holland, Yorkshire (GB); Richard Bojar, Yorkshire (GB); David West, Salisbury (GB)

(73) Assignee: MICREOS B.V., Wageningen (NL)

( * ) Notice: Subject to any disclaimer, the term of this patent is extended or adjusted under 35 U.S.C. 154(b) by 1156 days.

(21) Appl. No.: 12/654,176

(22) Filed: Dec. 11, 2009

(65) Prior Publication Data
US 2010/0226890 A1   Sep. 9, 2010

Related U.S. Application Data

(63) Continuation of application No. 12/216,074, filed on Jun. 30, 2008, now abandoned, which is a continuation of application No. 11/483,178, filed on Jul. 10, 2006, now Pat. No. 7,405,066.

(30) Foreign Application Priority Data

Jul. 12, 2005 (GB) .................................. 0514324.3
Dec. 15, 2005 (GB) .................................. 0525552.6

(51) Int. Cl.
*C12N 7/00* (2006.01)
*C07H 21/04* (2006.01)
*A61K 35/76* (2015.01)

(52) U.S. Cl.
CPC ......... *C12N 7/00* (2013.01); *C12N 2795/00032* (2013.01); *G01N 2500/00* (2013.01); *A61K 35/76* (2013.01); *G01N 2800/20* (2013.01)

(58) Field of Classification Search
USPC ....................................................... 435/235.1
See application file for complete search history.

(56) References Cited

U.S. PATENT DOCUMENTS

| | | | | |
|---|---|---|---|---|
| 6,121,036 | A * | 9/2000 | Ghanbari et al. ........... | 435/235.1 |
| 7,405,066 | B2 * | 7/2008 | Holland et al. ............. | 435/235.1 |
| 2003/0180319 | A1 * | 9/2003 | Rapson et al. ............. | 424/199.1 |
| 2004/0241825 | A1 | 12/2004 | Mandeville et al. | |
| 2005/0032036 | A1 | 2/2005 | Weber-Dabrowska et al. | |

FOREIGN PATENT DOCUMENTS

| | | |
|---|---|---|
| EP | 0 414 304 A3 | 2/1991 |
| WO | WO 01/51066 A2 | 7/2001 |
| WO | WO 01/90366 A2 | 11/2001 |
| WO | WO 02/07742 A2 | 1/2002 |
| WO | WO 03/080823 A2 | 10/2003 |
| WO | WO 2005/009451 A1 | 2/2005 |

OTHER PUBLICATIONS

Webster et al, J. Clin. Microbiology 7(1):84-90, 1978.*
Guo et al, Proc Natl Acad Sci 101(25):9205-9210, 2004.*
Farrar et al, J. Bacteriology 189(11): 4161-4167, 2007.*
Miskin et al, Microbiology 143:1745-1755, 1997.*
Bruggemann et al, Science 305:671-673, 2004.*
Puhvel, S.M., et al; "Changes in bochemical characterisation of phase sensitive . . . "; V 201; Abstract Annual Meeting Amer. Soc. Microbiology; 72 (1972).
Jong, E.C., et al; "Studies on Bacteriophages of *Propionibacterium acnes*"; *Med. Microbiol. Immunol.*; 161; pp. 263-271 (1975).
Shallta, A.R., et al; "Acne Vulgaris: Pathogenesis and Treatment"; *Cosmetics & Toiletries*; vol. 98; pp. 57-60 (1983).
Mills, O.H., et al; External Factors Aggravating Acne; *Dermatologic Clinics*; vol. 1, No. 3; pp. 365-370 (1983).
Williamson, P., et al; "A New method for the Quantitative Investigation of Cutaneous Bacteria"; *The Journal of Investigative Dermatology*; vol. 45, No. 5; pp. 498-503 (1965).
Cunliffe, B.; "Diseases of the Skin and their Treatment"; *The Pharmaceutical Journal*; vol. 267; pp. 749-752 (2001).
Besemer, J., et al; "Heuristic approach to deriving models for gene finding"; *Nucleic Acids Research*; vol. 27, No. 19; pp. 3911-3920 (1999).
Vieira, T., et al; (1999); "Viruses as Therapeutic Agents for Treating Bacterial Infections"; *Poster Presentation on* Apr. 24, 1999 *at the 53rd Annual Eastern Colleges Science Conference*; Sacred Heart University, Fairfield, CT.
Jedrzkiewicz, B., et al; (2000); "Combating the Antibiotic Resistance Crisis: Therapeutic use of Bacteriophages (Viruses) for Treating Acne, A Bacterial Disease"; *Poster Presentation on* Apr. 1, 2000 *at the 45th Annual Eastern Colleges Science Conference*, Wagner College, Staten Island, NY.
Hany, C., et al; (2001); "The Use of Bacteriophage to Treat Acne, A Bacterial Disease"; *Poster Presentation on* Mar. 31, 2001 *at the 55th Annual Eastern Colleges Science Conference*, Wilkes University, Wilkes-Barre, PA.
Armack, S., et al; (2002); "Bacteriophage Therapy for the Treatment of the Bacterial Disease Acne"; *Poster Presentation on* Apr. 27, 2002 *at the 56th Annual Eastern Colleges Science Conference*, Niagara University, Niagara, NY.
Aminti, K., et al; Bacteriophage Therapy for the disease Acne: Identification and Purification of Candidate Bacteriophage; *Poster Presentation on* Apr. 12, 2003 *at the 57th Annual Eastern Colleges Science Conference*, Ithaca College, Ithaca, NY.
Geronimo, J., et al; "Bacteriophage Therapy for the Skin disease Acne"; *Poster Presentation on* Apr. 2, 2004 *at the 58th Annual Eastern Colleges Science Conference*, Manhattan College, Riverdale, NY.
Summers, W.C., "Felix d'Herelle and the Origins of Molecular Biology", Chapter 8, pp. 108-124, 199-200 (1999).
Human ORF2466 cDNA SEQ ID No. 4931, WO200190366 from p. 18 of Office Action dated Jul. 2, 2007 mailed in U.S. Appl. No. 11/483,178.

* cited by examiner

*Primary Examiner* — Kevin Hill
(74) *Attorney, Agent, or Firm* — Nixon & Vanderhye P.C.

(57) ABSTRACT

There is provided a bacteriophage capable of lysing a *P. acnes* bacterium and incapable of lysing a bacterium which is not *P. acnes*, and which is incapable of sustaining lysogeny in a bacterium. There is also provided a pharmaceutical composition comprising such a bacteriophage.

11 Claims, 7 Drawing Sheets

P. acnes phage 103672

FIG. 7

| | | |
|---|---|---|
| 1894 | ATCCTTGTGTGGCTAGGGGT------------------------------------- | 25946 |
| 103609 | ATTCGTGTGTGGCTAGGGGT------------------------------------- | 25973 |
| 103672 | TTTCCTGTATGGTTAGATGT------------------------------------- | 25942 |
| PA6 | TTTCTTGTGTGGCTAGGGGTGATGGCTTCTTTCGCCCAATAGGATGTGCCACCGCTGGTC | 26281 |
| | * * *** *** *** *** ** | |
| 1894 | ------------------------------------------------------------ | |
| 103609 | ------------------------------------------------------------ | |
| 103672 | ------------------------------------------------------------ | |
| PA6 | CAGTATCCGAGTTTGTTGCGCTGCATGCCCTTGGCGTCCATCTCGTCGATAGTGAGGCAC | 26341 |
| 1894 | ------------------------------------------------------------ | |
| 103609 | ------------------------------------------------------------ | |
| 103672 | ------------------------------------------------------------ | |
| PA6 | CTGCGGCGATTGGGGCCCTGTCTTGACCCCGTGGTCCGTGTCCGGTGCATGTGCCTGAG | 26401 |
| 1894 | ------------------------------------------------------------ | |
| 103609 | ------------------------------------------------------------ | |
| 103672 | ------------------------------------------------------------ | |
| PA6 | GTGGTACTCCGTGAATGTTTCATGGCAGAGATGTACAGTGCTCTGGTCGATATCCGGTGATT | 26461 |
| 1894 | ------------------------------------------------------------ | |
| 103609 | ------------------------------------------------------------ | |
| 103672 | ------------------------------------------------------------ | |
| PA6 | GTGCTATCGCACTTGTGGCATGTCCATTCCATGATTGCTCCTATTTCCATTATAAGACT | 26521 |
| 1894 | ------------------------------------------------------------ | |
| 103609 | ------------------------------------------------------------ | |
| 103672 | ------------------------------------------------------------ | |
| PA6 | TCCTGTAGTGCCATTTTAGCGCCCTTGCGGGTCTTGGGGGTACAACTATATAGGTCAGGTG | 26581 |
| 1894 | -------TTTATCGGGCACACAGGGTGA | 25967 |
| 103609 | -------TTTATCGGCTGTACAGGGTGA | 25994 |
| 103672 | -------TTTATCGGGCACACAGGGTGA | 25963 |
| PA6 | TTTCTAGGCGATTCTAGGCTCATTGTGTGGCTGGGTTTTATCGGGCACACAGGGTGA | 26641 |
| | ******** ********* | |

FIG. 8

BACTERIOPHAGE AND THEIR USES

This application is a continuation of application Ser. No. 12/216,074 filed Jun. 30, 2008 now abandoned, which is a continuation of application Ser. No. 11/483,178, filed Jul. 10, 2006 now U.S. Pat. No. 7,405,066, the entire contents of each of which are hereby incorporated by reference.

The invention relates to bacteriophage and their uses. In particular, though not exclusively, it relates to their use in compositions for the treatment of acne.

BACKGROUND

Acne vulgaris is one of the most common diseases of the skin and in cases of extreme disfigurement can sometimes have severe consequences for the personality development of young people with ensuing social and economic problems. Adolescents suffering from acne show higher levels of anxiety, greater social inhibition and increased aggression compared to non-acne individuals. Amongst skin diseases, acne is the second highest cause of suicides.

Acne is an exclusively human disease and a unique condition of human sebaceous follicles of the face, chest and back. Spontaneous regression is common, taking about 15 years to complete. However, in about 5 percent of cases, acne persists beyond the age of 25 years and extends into the fourth and fifth decades of life. The earlier the symptoms start, the more severe is the course of the disease. The prevalence of the disease does not reflect any preference for male or female but usually the course is more severe in males.

The onset of the disease in an individual coincides with entry into puberty and is associated with an androgen-driven rise in sebum excretion rate and an increased colonisation of the sebaceous follicles with *Propionibacterium acnes* (*P. acnes*). Recent data indicates that the initiation of individual lesions is primarily inflammatory rather than via keratinocyte hyperproliferation.

Contrary to popular opinion, hygiene and diet have little or no effect on the aetiology of acne. Acne can be exacerbated by external factors such as friction (acne mechanica) (Shalita A R (1983) *Cosmetics and Toiletries* 98: 57-60) and pore-clogging cosmetics (acne cosmetica) (Mills O. H. & Kilgman A. M. (1988) *Dermatol. Clin.* 1: 365-370). The bacterium *P. acnes* is an inhabitant of the human skin and forms a major part of the natural skin flora. There is a wealth of circumstantial evidence implicating *P. acnes* as a major factor in the disease: increased colonisation of the skin by *P. acnes* is associated with the onset of the disease; patients with severe acne are significantly more sensitised to *P. acnes* than normal individuals; the overall immunological status of patients is elevated compared to acne-free individuals of the same age; successful antibiotic treatment reduces the density of *P. acnes* on the skin; and antibiotic therapeutic failure is associated with the presence of antibiotic resistant *P. acnes* on the skin of the patient.

Current treatments for acne focus on various factors contributing to the disease. In summary, anti-comedonal treatments include retinoids and azelaic acid (topical treatments) and isotretinoin (oral treatments); anti-*P. acnes* treatments include benzoyl peroxide, azelaic acid, erythromycin, tetracycline and clindamycin (topical treatments) and tetracycline, erythromycin, minocycline and trimethoprim (oral treatments); anti-inflammatory treatments include tetracycline, erythromycin, clindamycin and nicotinamide (topical treatments) and tetracycline, minocycline, trimethoprim and isotretinoin (oral treatments); and anti-seborrhoeic treatments include spironolactone (topical treatments) and Dianette™ and isotretinoin (oral treatments).

The more common mild and moderate cases of acne are treated with antibiotics, usually topically. There are increasing concerns emerging over the use of antibiotics for acne, where treatments last for long periods of time, up to 2-3 years in some cases. The concerns are two fold. First, the emergence of antibiotic resistant *P. acnes* world-wide with the consequence of reducing their efficacy for acne therapy. Second and possibly more importantly, there is the selection of an increasing pool of antibiotic resistant genes in the commensal microflora, mainly coagulase-negative *staphylococci* and *corynebacteria*, on patients' skin. These resistance genes may be horizontally transferred to related species, e.g. *Staphylococcus aureus*, which is a major opportunistic pathogen in the hospital and community environments. Therefore all efforts are required to restrict the use of antibiotics over extended treatment periods as used in the treatment of acne. Obtaining licences to market antibiotic therapies for acne is becoming especially difficult.

Side effects from these treatments are commonplace. Mild irritant dermatitis is associated with virtually all topical therapies (Cunliffe W. J., (2001) *Pharmaceut. J.* 267 749-752). Oral courses of antibiotics have side effects regardless of the condition for which they are prescribed and these often result from their lack of specificity, unbalancing (in due course) much of the bacterial flora in many sites in the body. This leaves room for resistant flora to flourish, resulting in, for example, vaginal candidiasis in women. Retinoid treatment has many side effects: it is a teratogen; causes cheilitis, facial dermatitis and conjunctivitis; leads to secondary skin infections; and has been associated with mood swings and depression.

Therefore, there is a need to develop new approaches for acne therapy which specifically target *P. acnes*.

The idea of employing bacteriophage (naturally occurring bacterial viruses) for the treatment or prevention of bacterial diseases was realised relatively soon after the discovery of phage (the words "bacteriophage" and "phage" are used interchangeably throughout this specification) by Felix d'Herelle in 1917. The fact that bacteriophage can specifically infect a bacterial host and rapidly kill it suggested to d'Herelle that this was potentially a very effective way of controlling bacterial infection in man (for review, see "Felix d'Herelle and the Origins of Molecular Biology" William C. Summers (Yale University Press, ISBN 0-300-07127-2)). This potential was never fully realised because of the advent of the antibiotic era, but phage therapy has been pursued since then, in many cases successfully, in former states of the USSR and Eastern Europe.

The emergence of drug resistance and the difficulty in developing novel antibiotics and vaccines has highlighted a growing need to find alternative methods of treatment.

WO03/080823 discloses a method for generating candidate bacteriophage for use in therapy by mutating temperate bacteriophage and producing a cocktail of phages. This disclosure specifically selects lysogenic phage, observing that for some bacteria they are more numerous and, therefore, easier to isolate than lytic phage. The phage then have to be mutated to produce lytic vir mutants, in order to avoid the problems associated with lysogenic phage as a therapy, as discussed further below. Treatment of *P. acnes* is mentioned.

EP0414304 relates to the use of bacteriophage to kill bacteria, including *P. acnes*. There is no disclosure of a bacteriophage capable of lysing multiple strains of *P. acnes* bacteria and yet which is incapable of lysing a bacterium which is not *P. acnes* and incapable of sustaining lysogeny in a bacterium.

Jong et al (Med. Microbiol. Immunol. 161 (1975) 263-271) describes isolation of *P. acnes* phage. The paper focuses on the classification of the phage and does not disclose a bacteriophage capable of lysing multiple strains of *P. acnes* bacteria and yet which is incapable of lysing a bacterium which is not *P. acnes* and incapable of sustaining lysogeny in a bacterium.

Puhvel & Reisner (Amer. Soc. Microbiol. 72 (1972) V201) is an abstract relating to the generation of lysogenic phage-resistant strains of *P. acnes*.

WO01/51066 relates to the use of bacteriophage to reduce risk of infection or sepsis, particularly in immunocompromised patients. The disclosed methodology aims to achieve the numerical reduction or elimination of various members of the body's natural bacterial flora, in order to reduce the chance of them causing disease in immunocompromised patients. This is specifically risk reduction rather than cure and is concerned in particular with infections which complicate conditions such as certain cancers, AIDS and cystic fibrosis and which complicate the condition of transplant patients. No mention is made of treatment of *P. acnes*.

U.S. Pat. No. 6,121,036 relates to a purified, host specific, non-toxic, wide host range bacteriophage preparation containing at least two phage. The document describes some of the features of an effective phage therapy—that it should be safe, have broad host range and kill a large proportion of bacteria strains—and indicates that such a preparation of appropriate phage could be used to treat *P. acnes* infections. However, no disclosure is made about which phage are suitable for this purpose or that such safe, lytic, broad host range phage exist for *P. acnes*.

WO02/07742 purports to disclose a method for potentiating a wider host range for a phage by cloning tail protein-encoding genes from another phage with different host specificity. The document indicates that wide specificity is desirable from a phage therapy point of view but, rather than selecting from naturally occurring phage variants, describes the synthetic construction of a hybrid bacteriophage with dual tail fibre types, therefore having corresponding dual host specificity. This specificity is hypothetically extended to apply the invention in the engineering of a phage which can infect not only different species strains but different bacteria within a species and even within different genera. However, there is no evidence for this potential beyond results showing that a hybrid phage had been created having the ability to infect two different strains of *Escherichia coli*. The application of a suitably modified phage for gene therapy in humans is also contemplated. Specific phage, modified or unmodified, for the treatment of acne are not disclosed. There is no mention of a *P. acnes* bacteriophage with a single host species specificity but with multiple strain specificity.

US2005/0032036 describes a method for sorting through a phage collection and determining the composition of a phage cocktail in order to optimise broad host range infection and lysis, particularly in reference to *Pseudomonas* and *Staphylococcus* strains. No disclosures are made in relation to the field of acne phage therapy.

WO2005/009451 relates in particular to the use of bacteriophage as a part of a combination therapy with traditional, chemical antibiotics, particularly in the treatment of *Pseudomonas aeruginosa* infections and particularly in the treatment of bacteria within biofilms. It describes the difficulty in finding phage with sufficiently broad host specificity to be of therapeutic value for treatment of any given infection and advocates the use of multiple bacteriophage types for therapy, whether simultaneously, separately or sequentially. It also indicates that greater virulence in a phage can be induced artificially by genetic manipulation methods to produce phage with broader specificity or greater infection potential. There is no mention of *P. acnes*, which is not characterised by biofilm formation.

US2004/0241825 discloses several methods for genetically labelling bacteriophage (with a non-functional stretch of DNA that can be detected by, for example, PCR, enabling identification of the phage), identifying non-cross reacting bacteriophage (a multi-step process to isolate phage against the target host and, from these, isolating bacteriophage which do not infect more than 5% of non-pathogenic, non-target hosts) and, finally, a method for selecting phage that are resistant to genetic modification by host bacteria (which involves infecting bacteria with a sample of bacteriophage, isolating progeny phage and comparing the restriction digest patterns of the original bacteriophage and the progeny to identify any differences that would be indicative of genetic modification). Implicit in this disclosure is the difficulty in identifying suitable candidate bacteriophage for use in a therapy. The application of this methodology to *P. acnes* is not described.

Several conference presentations by the research group of Michael Davis at Central Connecticut State University have outlined plans to identify lytic phage having broad host range specificity (Vieira T. and Davis M. A. (1999) Viruses as Therapeutic Agents for Treating Bacterial Infections. Poster presentation on Apr. 24, 1999 at the 53rd Annual Eastern Colleges Science Conference, Sacred Heart University, Fairfield Conn.; Jedrzkiewicz B. and Davis M. A. (2000) Combating the Antibiotic Resistance Crisis: Therapeutic Use of Bacteriophages (Viruses) for Treating Acne, A Bacterial Disease. Poster presentation on Apr. 1, 2000 at the 54th Annual Eastern Colleges Science Conference, Wagner College, Staten Island N.Y.; Hany C. et al., (2001) The Use of Bacteriophage to Treat Acne, A Bacterial Disease. Poster presentation on Mar. 31, 2001 at the 55th Annual Eastern Colleges Science Conference, Wilkes University, Wilkes-Barre Pa.; Armack S. et al. (2002) Bacteriophage Therapy For The Treatment Of The Bacterial Disease Acne. Poster presentation on Apr. 27, 2002 at the 56th Annual Eastern Colleges Science Conference, Niagara University, Niagara N.Y.; Aminti K. et al. (2003) Bacteriophage Therapy For The Disease Acne: Identification And Purification Of Candidate Bacteriophage. Poster presentation on Apr. 12, 2003 at the 57th Annual Eastern Colleges Science Conference, Ithaca College, Ithaca N.Y.; Geronimo J. et al (2004) Bacteriophage Therapy For the Skin Disease Acne. Poster presentation on Apr. 2, 2004 at the 58th Annual Eastern Colleges Science Conference, Manhattan College, Riverdale N.Y.). No disclosures have been made in relation to the specific properties of such phage or to specific phage isolates.

DESCRIPTION OF THE INVENTION

According to a first aspect of the invention there is provided a bacteriophage capable of lysing a *P. acnes* bacterium and incapable of lysing any bacterium which is not *P. acnes*, and which is incapable of sustaining lysogeny in a bacterium.

Such a phage has the ability to infect a wide range of bacterial strains within a species but with absolute species specificity. This is one of the most important and usually unachievable aims in the development of an effective phage therapy. In addition, a bacteriophage according to the invention is purely lytic, i.e. incapable of entering the lysogenic phase of the bacteriophage life cycle, a quiescent stage which is undesirable in the creation of an effective therapy and is also unacceptable from a regulatory point of view.

Advantageously, such a bacteriophage can be used in the treatment of acne. No side effects have been reported or are expected in the use of phage therapy, whether delivered systemically, orally or topically. The bacteriophage is specific to *P. acnes* and therefore leaves other members of the skin flora unaffected, reducing the opportunity for the overgrowth of potentially harmful flora. The protective nature of the normal resident microflora is therefore maintained. The specificity of a phage therapy approach to treatment of acne also eliminates the possibility of drug resistance emerging in other members of the microflora: other antibacterial treatments offer a broad brush stroke approach to eliminating bacteria and therefore, under the appropriate conditions, provide an opportunity for developing drug resistance not only in *P. acnes* but in other important commensals with pathogenic potential, e.g. *Staphylococcus aureus*. A further advantage of bacteriophage treatment is that it is self regulating: as the population of host *P. acnes* cells reduces, so will the bacteriophage numbers. In addition, such a bacteriophage can be used as a general prophylactic measure; the use of antibiotics in unprescribed cosmetic products (such as face washes, etc) is undesirable for many reasons relating to safety and the issue of antibiotic resistance. In fact there are strong arguments for limiting the use of antibiotics to reduce the incidence of resistance. Specificity of the bacteriophage means that it is suitable for widespread use in these situations and could be employed as part of a general hygiene routine for the prevention of acne. In addition, the use of the bacteriophage may be effective even against bacterial strains which have become resistant to antibiotics.

As mentioned above, the use of a bacteriophage which can lyse *P. acnes* but is incapable of sustaining lysogeny has the advantage that the bacteriophage cannot lie dormant within a bacterium, but must lyse the bacterium and hence kill it.

Preferably, the bacteriophage lacks the ability to express at least one gene necessary for sustaining lysogeny. The term "lacks the ability to express" is intended to indicate that the bacteriophage lacks the ability to produce a fully functional protein product necessary to sustain lysogeny, for example, as the result of one or more point mutations or full or partial deletions of the genome. More preferably, the phage has a genome which lacks all or part of at least one gene necessary for sustaining lysogeny. Alternatively or additionally, the phage may comprise defects (e.g. mutations, insertions or deletions) in the genome in non-coding regions which may, nonetheless, affect the ability of the phage to sustain lysogeny, for example defects in the genome integration site(s) (e.g. the /att/ site) or in the repressor binding site. The phage is preferably naturally occurring and isolated, with the added advantage that artificial mutations need not be introduced into the bacteriophage. Such mutations, whilst not ruled out, could have potentially unknown results which could be harmful to the individual to whom the bacteriophage is administered. If the phage contains artificial mutations, or is otherwise non-naturally occurring, it is still preferred that the phage is obtained in an isolated state.

In a preferred embodiment, the bacteriophage according to this aspect of the invention is capable of lysing a plurality of strains of the *P. acnes* bacterium. For example, the bacteriophage according to this aspect of the invention may be capable of lysing 5 strains of the *P. acnes* bacterium, preferably at least 10 strains, more preferably at least 16 strains, or at least 17 strains, or at least 18 strains, or at least 19 strains, or at least 20 strains. Most preferably, the bacteriophage is capable of lysing at least 21 strains.

Preferably, the bacteriophage according to this aspect of the invention is isolated and selected from those phage characterised hereinafter as: 103609; 103672; and 1894.

The following isolates of bacteriophage have been deposited under the terms of the Budapest Treaty at The National Collection of Industrial, Marine and Food Bacteria (NCIMB), Ferguson Building, Craibstone Estate, Bucksburn, Aberdeen, AB21 9YA, United Kingdom, under the following accession numbers: Accession no. NCIMB 41332 (isolate PA6); Accession no. NCIMB 41334 (isolate 1874); Accession no. NCIMB 41333 (isolate 1878); Accession no. NCIMB 41335 (isolate 1905); Accession no. NCIMB 41349 (isolate 1894); Accession no. NCIMB 41350 (isolate 103609); Accession no. NCIMB 41351 (isolate 103672). The host bacteria, *P. acnes*, AT1 was also deposited as NCIMB 41336.

The bacteriophage may have a genome which comprises the DNA sequence of SEQ ID NO:3, or a genome having sequence identity of at least 87% with the DNA sequence of SEQ ID NO:3, more preferably sequence identity of at least 88% with that sequence, yet more preferably sequence identity of at least 90% with that sequence, most preferably sequence identity of at least 95%, 96%, 97%, 98% or 99% with that sequence. Alternatively or in addition, the bacteriophage may have a genome comprising a functional fragment of the DNA sequence of SEQ ID NO:3. For example, the functional fragment may be selected from within the Open Reading Frames shown in FIG. 2. Alternatively, the functional fragment may comprise a DNA sequence having sequence identity of at least 95% with the DNA sequence of FIG. 6, preferably sequence identity of at least 96%, more preferably sequence identity of at least 97% with that sequence, most preferably sequence identity of at least 98% or 99% with that sequence. In a preferred embodiment, the functional fragment comprises the DNA sequence of FIG. 6.

Alternatively, the bacteriophage may have a genome which comprises the DNA sequence of SEQ ID NO:4, or a genome having sequence identity of at least 88% with the DNA sequence of SEQ ID NO:4, more preferably sequence identity of at least 89% with that sequence, yet more preferably sequence identity of at least 90% with that sequence, most preferably sequence identity of at least 95%, 96%, 97%, 98% or 99% with that sequence. Alternatively or in addition, the bacteriophage may have a genome comprising a functional fragment of the DNA sequence of SEQ ID NO:4. For example, the functional fragment may be selected from within the Open Reading Frames shown in FIG. 3. Alternatively, the functional fragment may comprise a DNA sequence having sequence identity of at least 95% with the DNA sequence of SEQ ID NO:7, preferably sequence identity of at least 96%, more preferably sequence identity of at least 97% with that sequence, most preferably sequence identity of at least 98% or 99% with that sequence. In a preferred embodiment, the functional fragment comprises the DNA sequence of SEQ ID NO:7.

In a further alternative, the bacteriophage may have a genome which comprises the DNA sequence of SEQ ID NO:5, or a genome having sequence identity of at least 88% with the DNA sequence of SEQ ID NO:5, more preferably sequence identity of at least 89% with that sequence, yet more preferably sequence identity of at least 90% with that sequence, most preferably sequence identity of at least 95%, 96%, 97%, 98% or 99% with that sequence. Alternatively or in addition, the bacteriophage may have a genome comprising a functional fragment of the DNA sequence of SEQ ID NO:5. For example, the functional fragment may be selected from within the Open Reading Frames shown in FIG. 4. Alternatively, the functional fragment may comprise a DNA sequence having sequence identity of at least 95% with the DNA sequence of SEQ ID NO:8, preferably sequence identity of at least 9.6%, more preferably sequence identity of at least 97% with that sequence, most preferably sequence identity of at least 98% or 99% with that sequence. In a preferred embodiment, the functional fragment comprises the DNA sequence of SEQ ID NO:8.

Alternatively or additionally, the functional fragment may comprise the DNA sequence of one or more of:
a DNA sequence having sequence identity of at least 63%, 70%, 80%, 90%, 95% or 99% with ORF1 of SEQ ID NO:3, 4 or 5;
a DNA sequence having sequence identity of at least 91%, 95% or 99% with ORF2 of SEQ NO:3, 4 or 5;
a DNA sequence having sequence identity of at least 91%, 95% or 99% with ORF3 of SEQ ID NO:3, 4 or 5;
a DNA sequence having sequence identity of at least 91%, 95% or 99% with ORF4 of SEQ ID NO:3, 4 or 5;
a DNA sequence having sequence identity of at least 89%, 90%, 95% or 99% with ORF5 of SEQ ID NO:3, 4 or 5;
a DNA sequence having sequence identity of at least 92%, 95% or 99% with ORF6 of SEQ ID NO:3, 4 or 5;
a DNA sequence having sequence identity of at least 96%, 97%, 98% or 99% with ORF7 of SEQ ID NO:3, 4 or 5;
a DNA sequence having sequence identity of at least 94%, 95% or 99% with ORF8 of SEQ ID NO:3, 4 or 5;
a DNA sequence having sequence identity of at least 95%, 97%, 98% or 99% with ORF9 of SEQ ID NO:3, 4 or 5;
a DNA sequence having sequence identity of at least 91%, 95% or 99% with ORF10 of SEQ ID NO:3, 4 or 5;
a DNA sequence having sequence identity of at least 93%, 95% or 99% with ORF11 of SEQ ID NO:3, 4 or 5;
a DNA sequence having sequence identity of at least 97%, 98% or 99% with ORF12 of SEQ ID NO:3, 4 or 5;
a DNA sequence having sequence identity of at least 99% with ORF13 of SEQ ID NO:3, 4 or 5;
a DNA sequence having sequence identity of at least 91%, 95% or 99% with ORF14 of SEQ ID NO:3, 4 or 5;
a DNA sequence having sequence identity of at least 93%, 95% or 99% with ORF15 of SEQ ED NO:3, 4 or 5;
a DNA sequence having sequence identity of at least 94%, 95% or 99% with ORF16 of SEQ ID NO:3, 4 or 5;
a DNA sequence having sequence identity of at least 97%, 98% or 99% with ORF17 of SEQ ID NO:3, 4 or 5;
a DNA sequence having sequence identity of at least 67%, 70%, 80%, 90%, 95% or 99% with ORF18 of SEQ ID NO:3, 4 or 5;
a DNA sequence having sequence identity of at least 80%, 90%, 95% or 99% with ORF19 of SEQ ID NO:3, 4 or 5;
a DNA sequence having sequence identity of at least 88%, 90%, 95% or 99% with ORF20 of SEQ ID NO:3, 4 or 5;
a DNA sequence having sequence identity of at least 86%, 90%, 95% or 99% with ORF21 of SEQ ID NO:3, 4 or 5;
a DNA sequence having sequence identity of at least 97%, 98% or 99% with ORF22 of SEQ ID NO:3, 4 or 5;
a DNA sequence having sequence identity of at least 98% or 99% with ORF23 of SEQ ID NO:3, 4 or 5;
a DNA sequence having sequence identity of at least 93%, 95% or 99% with ORF24 of SEQ ID NO:3, 4 or 5;
a DNA sequence having sequence identity of at least 87%, 90%, 95% or 99% with ORF25 of SEQ ID NO:3, 4 or 5;
a DNA sequence having sequence identity of at least 63%, 70%, 80%, 90%, 95% or 99% with ORF26 of SEQ ID NO:3, 4 or 5;
a DNA sequence having sequence identity of at least 80%, 90%, 95% or 99% with ORF27 of SEQ ID NO:3, 4 or 5;
a DNA sequence having sequence identity of at least 78%, 80%, 90%, 95% or 99% with ORF28 of SEQ ID NO:3, 4 or 5;
a DNA sequence having sequence identity of at least 66%, 70%, 80%, 90%, 95% or 99% with ORF29 of SEQ ID NO:3, 4 or 5; and/or
a DNA sequence having sequence identity of at least 87%, 90%, 95% or 99% with ORF30 of SEQ ID NO:3, 4 or 5.

Preferably, the functional fragment comprises a DNA sequence which is conserved between all of SEQ ID NO:3, 4 and 5.

The bacteriophage may have a genome having sequence identity of at least 88% with the genome of the bacteriophage deposited under Accession No. NCIMB 41349, preferably sequence identity of at least 89%, more preferably sequence identity of at least 90%, most preferably sequence identity of at least 95%, 96%, 97%, 98% or 99%.

The bacteriophage may have a genome having sequence identity of at least 87% with the genome of the bacteriophage deposited under Accession No. NCIMB 41350, preferably sequence identity of at least 88%, more preferably sequence identity of at least 90%, most preferably sequence identity of at least 95%, 96%, 97%, 98% or 99%.

The bacteriophage may have a genome having sequence identity of at least 88% with the genome of the bacteriophage deposited under Accession No. NCIMB 41351, preferably sequence identity of at least 89%, more preferably sequence identity of at least 90%, most preferably sequence identity of at least 95%, 96%, 97%, 98% or 99%.

The term "sequence identity", as used throughout this specification, is calculated as the percentage of nucleotides present in the smaller of the two sequences to be compared that may also be found in the larger of the two sequences, the nucleotides preferably being arranged in the same order in both sequences. The skilled person would readily be able to determine the level of sequence identity between sequences, for example by use of the Blast analysis tool at http://www.ncbi.nlm.nih.gov/BLAST/, using the default parameter settings. Preferably, the length of the shorter of the two sequences being compared is at least 60% of the length of the longer of the two sequences, more preferably at least 70% of the length, yet more preferably at least 80% of the length and still more preferably at least 90%, 95%, 96% 97% 98% or 99% of the length. In a most preferred embodiment, the sequences to be compared are identical in length.

The term "functional fragment", as used throughout this specification, indicates a portion of the full length sequence which has substantially identical functionality to the full length sequence itself. For example, when reference is made to a functional fragment of a bacteriophage genome, this indicates that the fragment, when contained in a bacteriophage, results in a bacteriophage according to the invention, i.e. a bacteriophage capable of lysing a *P. acnes* bacterium and incapable of lysing any bacterium which is not *P. acnes*, and which is incapable of sustaining lysogeny in a bacterium. Preferably, the size of the functional fragment is at least 30% of the size of the full length sequence, more preferably at least 40% of the size, yet more preferably at least 50% of the size, yet more preferably at least 60%, 70%, 80%, 85%, 90% or 95% of the size.

In a preferred embodiment, the bacteriophage has a genome which does not comprise one or more of the nucleotide sequences shown in SEQ ID NO:9, SEQ ID NO:10, SEQ ID NO:11, SEQ ID NO:12 and SEQ ID NO:13. Without wishing to be bound by theory, it is considered that the properties of a bacteriophage according to the invention, namely that the bacteriophage is capable of lysing a *P. acnes* bacterium, incapable of lysing any bacterium which is not *P. acnes* and incapable of sustaining lysogeny in a bacterium, may be associated with the absence of one or more of these sequences from the genome of the bacteriophage.

Preferably, the bacteriophage is isolated and is selected from those herein characterised as 103609, 103672 and 1894.

The bacteriophage according to the first aspect of the invention may be modified to comprise a marker molecule. The term "marker molecule", as used throughout this specification, is intended to include, but not be limited to, markers or tags such as biotin, a his-tag or a label recognisable by a binding partner such as an antibody, useable, for example, to isolate the bacteriophage. Markers suitable for use in affinity purification processes include glutathione-5-transferase (GST), protein A, ScFv and lectins. Other modifications of the bacteriophage may be made, e.g. for reducing phage antigenicity, including use of a PEG (polyethylene glycol) conjugate or a polysialic acid conjugate. Modifications may also include the addition of molecules which enhance the lethality of the phage to the bacterial host. Examples are given in Westwater C. et al. (2003) *Antimicrob. Agents Chemotherapeutics* 47: 1301-1307. Other suitable markers and modifications will be well known to the skilled person. The marker molecule may be incorporated at the DNA level or may be attached chemically at the phage surface.

According to a second aspect of the invention, there is provided an isolated polynucleotide having the nucleotide sequence of the genome of a bacteriophage according to the first aspect of the invention. Alternatively or additionally, the polynucleotide may comprise the nucleotide sequence of any one of SEQ ID NO:3, SEQ ID NO:4, SEQ ID NO:5 or the complement thereof, or may comprise a functional fragment of the DNA sequence of any one of SEQ ID NO:3, SEQ ID NO:4 or SEQ ID NO:5; when a bacteriophage comprises a polynucleotide according to the second aspect of the invention, it has the properties of a bacteriophage according to the first aspect of the invention.

Preferably, the polynucleotide has sequence identity of at least 87% with the DNA sequence of SEQ ID NO:3, preferably sequence identity of at least 88%, more preferably sequence identity of at least 90%, most preferably sequence identity of at least 95%, 96%, 97%, 98% or 99% with that sequence.

In an alternative preferred embodiment, the polynucleotide has sequence identity of at least 88% with the DNA sequence of SEQ ID NO:4, preferably sequence identity of at least 89%, more preferably sequence identity of at least 90%, most preferably sequence identity of at least 95%, 96%, 97%, 98% or 99% with that sequence.

In a further alternative preferred embodiment, the polynucleotide has sequence identity of at least 88% with the DNA sequence of SEQ ID NO:5, preferably sequence identity of at least 89%, more preferably sequence identity of at least 90%, most preferably sequence identity of at least 95%, 96%, 97%, 98% or 99% with that sequence.

The functional fragment may be selected from one or more of the Open Reading Frames (ORFs) shown in any of FIG. 2, 3 or 4, i.e. the ORFs within SEQ ID NO:3, 4, or 5 (respectively), the boundaries of which are defined in Table 5 below. Alternatively, the functional fragment may comprise a DNA sequence having sequence identity of at least 95% with any one of the DNA sequences selected from SEQ ID NO:6, SEQ ID NO:7 and SEQ ID NO:8, preferably sequence identity of at least 96%, more preferably sequence identity of at least 97% with any one of those sequences, most preferably sequence identity of at least 98% or 99% with any one of those sequences. In a more preferred embodiment, the functional fragment comprises the DNA sequence of SEQ ID NO:6, SEQ ID NO:7 or SEQ ID NO:8.

Alternatively or additionally, the functional fragment may comprise one or more of:

a DNA sequence having sequence identity of at least 63%, 70%, 80%, 90%, 95% or 99% with ORF1 of SEQ ID NO:3, 4 or 5;

a DNA sequence having sequence identity of at least 91%, 95% or 99% with ORF2 of SEQ ID NO:3, 4 or 5;

a DNA sequence having sequence identity of at least 91%, 95% or 99% with ORF3 of SEQ ID NO:3, 4 or 5;

a DNA sequence having sequence identity of at least 91%, 95% or 99% with ORF4 of SEQ ID NO:3, 4 or 5;

a DNA sequence having sequence identity of at least 89%, 90%, 95% or 99% with ORF5 of SEQ ID NO:3, 4 or 5;

a DNA sequence having sequence identity of at least 92%, 95% or 99% with ORF6 of SEQ ID NO:3, 4 or 5;

a DNA sequence having sequence identity of at least 96%, 97%, 98% or 99% with ORF7 of SEQ ID NO:3, 4 or 5;

a DNA sequence having sequence identity of at least 94%, 95% or 99% with ORF8 of SEQ ID NO:3, 4 or 5;

a DNA sequence having sequence identity of at least 95%, 97%, 98% or 99% with ORF9 of SEQ ID NO:3, 4 or 5;

a DNA sequence having sequence identity of at least 91%, 95% or 99% with ORF10 of SEQ NO:3, 4 or 5;

a DNA sequence having sequence identity of at least 93%, 95% or 99% with ORF11 of SEQ ID NO:3, 4 or 5;

a DNA sequence having sequence identity of at least 97%, 98% or 99% with ORF12 of SEQ ID NO:3, 4 or 5;

a DNA sequence having sequence identity of at least 99% with ORF13 of SEQ ID NO:3, 4 or 5;

a DNA sequence having sequence identity of at least 91%, 95% or 99% with ORF14 of SEQ ID NO:3, 4 or 5;

a DNA sequence having sequence identity of at least 93%, 95% or 99% with ORF15 of SEQ ID NO:3, 4 or 5;

a DNA sequence having sequence identity of at least 94%, 95% or 99% with ORF16 of SEQ ID NO:3, 4 or 5;

a DNA sequence having sequence identity of at least 97%, 98% or 99% with ORF17 of SEQ ID NO:3, 4 or 5;

a DNA sequence having sequence identity of at least 67%, 70%, 80%, 90%, 95% or 99% with ORF18 of SEQ ID NO:3, 4 or 5;

a DNA sequence having sequence identity of at least 80%, 90%, 95% or 99% with ORF19 of SEQ ID NO:3, 4 or 5;

a DNA sequence having sequence identity of at least 88%, 90%, 95% or 99% with ORF20 of SEQ ID NO:3, 4 or 5;

a DNA sequence having sequence identity of at least 86%, 90%, 95% or 99% with ORF21 of SEQ ID NO:3, 4 or 5;

a DNA sequence having sequence identity of at least 97%, 98% or 99% with ORF22 of SEQ ID NO:3, 4 or 5;

a DNA sequence having sequence identity of at least 98% or 99% with ORF23 of SEQ NO:3, 4 or 5;

a DNA sequence having sequence identity of at least 93%, 95% or 99% with ORF24 of SEQ ED NO:3, 4 or 5;

a DNA sequence having sequence identity of at least 87%, 90%, 95% or 99% with ORF25 of SEQ ID NO:3, 4 or 5;

a DNA sequence having sequence identity of at least 63%, 70%, 80%, 90%, 95% or 99% with ORF26 of SEQ ID NO:3, 4 or 5;

a DNA sequence having sequence identity of at least 80%, 90%, 95% or 99% with ORF27 of SEQ ID NO:3, 4 or 5;

a DNA sequence having sequence identity of at least 78%, 80%, 90%, 95% or 99% with ORF28 of SEQ ID NO:3, 4 or 5;

a DNA sequence having sequence identity of at least 66%, 70%, 80%, 90%, 95% or 99% with ORF29 of SEQ ID NO:3, 4 or 5; and/or a DNA sequence having sequence identity of at least 87%, 90%, 95% or 99% with ORF30 of SEQ ID NO:3, 4 or 5.

The polynucleotide may comprise one or more of the Open Reading Frames shown in any of FIG. 2, 3 or 4.

Preferably, the polynucleotide has a nucleic acid sequence which does not comprise one or more of the sequences shown in SEQ ID NO:9, SEQ ID NO:10, SEQ ID NO:11, SEQ ID NO:12 and SEQ ID NO:13. Without wishing to be bound by theory, it is considered that the properties of a bacteriophage containing a polynucleotide according to the second aspect of the invention, namely that the bacteriophage is capable of lysing a *P. acnes* bacterium, incapable of lysing any bacterium which is not *P. acnes* and incapable of sustaining lysogeny in a bacterium, may be associated with the absence of one or more of these sequences from the polynucleotide according to the second aspect of the invention.

The polynucleotide may further comprise a nucleotide sequence encoding a marker molecule.

According to a third aspect of the invention there is provided an isolated polypeptide having an amino acid sequence encoded by the polynucleotide according to the second aspect of the invention.

According to a fourth aspect of the invention, there is provided a composition comprising at least one bacteriophage according to the first aspect of the invention and an adjuvant, carrier or vehicle.

Preferably, the composition is for use in the prevention or treatment of acne, or for use to improve the appearance of a mammal (preferably a human), the bacteriophage being present in an effective amount.

The term "treatment" (and equivalent terms such as "treating", "treat" etc), as used throughout this specification, is intended to indicate the reduction or elimination of the occurrence of the symptoms of acne. For example, symptoms include visible marks on the face such as papules (small raised red spots less than 5 mm in diameter), superficial pustules and deeper lesions (nodules and pustules larger than 5 mm in diameter). The deeper lesions can lead to scarring.

The composition preferably comprises two or more different isolates of bacteriophage. Each of the two or more isolates of bacteriophage may be a bacteriophage according to the first aspect of the invention.

Additionally or alternatively, the composition may comprise an isolated polynucleotide according to the second aspect of the invention or an isolated polypeptide according to the third aspect of the invention. Where the composition is for use in the prevention or treatment of acne, or for use to improve the appearance of a mammal (preferably a human), the isolated polynucleotide and/or isolated polypeptide is present in an effective amount.

The composition may be in a form suitable for oral, intravenous or topical administration. For example, the composition may be in a form suitable for oral administration and be a liquid, powder or tablet. Alternatively, the composition may be in a form suitable for intravenous administration and be a liquid, or a solid dissolvable in a liquid. In a further alternative, the composition may be in a form suitable for topical administration and be in the form of a cream, solution, powder, spray, aerosol, capsule, solid or gel, or may be bonded to a solid surface. The composition may also form part of a face wash, soap, application stick, cosmetic or dressing.

The bacteriophage, polynucleotide or polypeptide according to the invention contained in the composition may be within, or a part of, liposomes, capsules, carrier particles or, indeed, any other method of maintaining the bacteriophage, polynucleotide or polypeptide in a separate microenvironment within the composition. Alternatively, the bacteriophage, polynucleotide or polypeptide may be added directly to the composition, for example a bacteriophage may be added in a freeze-dried form.

The composition according to this aspect of the invention may further comprise at least one further agent selected from antibiotics, anti-comedonals, anti-*P. acnes* agents, anti-inflammatories and anti-seborrhoeics.

The composition may be a pharmaceutical composition or a cosmetic composition.

According to a fifth aspect of the invention, there is provided a method of preventing or treating acne comprising administering an effective amount of at least one bacteriophage according to the first aspect of the invention and/or of an isolated polynucleotide according to the second aspect of the invention and/or of an isolated polypeptide according to the third aspect of the invention and/or of a composition according to the fourth aspect of the invention to an individual in need of such prevention or treatment.

According to a sixth aspect of the invention, there is provided a method of improving the appearance of an individual, the method comprising administering to the individual an effective amount of a bacteriophage according to the first aspect of the invention and/or of an isolated polynucleotide according to the second aspect of the invention and/or of an isolated polypeptide according to the third aspect of the invention and/or of a composition according to the fourth aspect of the invention. Preferably, the individual is a human individual. The method is a non-therapeutic cosmetic method.

According to a seventh aspect of the invention, there is provided a method for isolating a bacteriophage capable of lysing a *P. acnes* bacterium, incapable of lysing any bacterium which is not *P. acnes* and incapable of sustaining lysogeny in a bacterium, comprising:
  a) obtaining a sample of bacteria from a skin surface:
  b) isolating from the sample bacteriophage which lyse *propionibacteria*;
  c) isolating the bacteriophage to determine if it is capable of lysing at least one *P. acnes* strain;
  d) testing the bacteriophage to determine if it is capable of lysing non-*P. acnes* bacterial strains;
  e) testing the bacteriophage to determine whether it is capable of sustaining lysogeny in a *P. acnes* strain;
  f) detecting a bacteriophage which has been shown in steps (c), (d) and (e) to be capable of lysing a *P. acnes* bacterium, incapable of lysing any bacterium which is not *P. acnes*, and incapable of sustaining lysogeny in a bacterium.

According to an eighth aspect of the invention, there is provided a method for identifying a bacteriophage which is capable of lysing a *P. acnes* bacterium, incapable of lysing any bacterium which is not *P. acnes* and incapable of sustaining lysogeny in a bacterium, comprising:
  a) exposing a *P. acnes* bacterium to the bacteriophage and determining that the bacterium is lysed;
  b) exposing at least one species of bacteria which is not *P. acnes* bacteria to the bacteriophage and determining that the bacteria are not lysed;
  c) determining that the bacteriophage is not capable of sustaining lysogeny in a bacteria.

Preferably, in step (b), at least three species of bacteria which are not *P. acnes* are exposed to the bacteriophage, more preferably at least four, at least five, at least 10, at least 20, at least 30, at least 40, or at least 50 different strains of bacteria.

According to a ninth aspect of the invention, there is provided a bacteriophage isolated or identified using the method according to the seventh or eighth aspects of the invention.

According to a tenth aspect of the invention, there is provided a bacteriophage obtainable or identifiable by using a method according to the seventh or eighth aspects of the invention.

Embodiments of the invention will now be described, by way of example only, with reference to the accompanying FIGS. 1-8 in which:

FIG. 7 shows an alignment of a portion of the DNA sequences of bacteriophage strains 103609, 103672, 1894 and PA6; and FIG. 8 shows an alignment of a further portion of the DNA sequences of bacteriophage strains 103609, 103672, 1894 and PA6

EXPERIMENTAL MATERIALS AND METHODS

1. Materials

Figure 1:
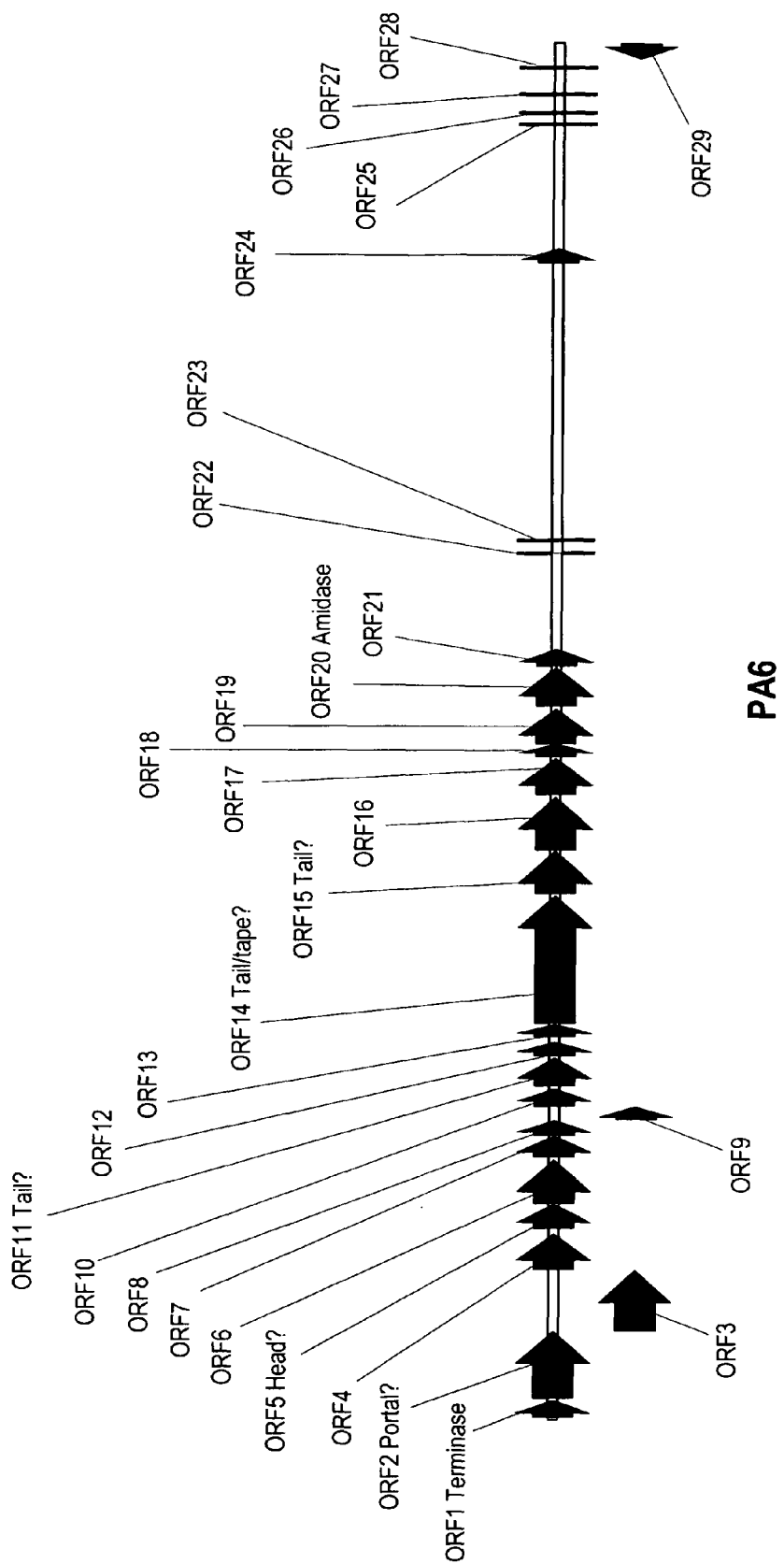
FIG. 1 shows the arrangement of open reading frames (ORFs) in the PA6 genome, with putative functions of various ORFs indicated.

Reinforced Clostridial Agar (RCA; Oxoid CM0151 (Oxoid Ltd., Basingstoke, UK))

TYG broth (1% (w/v) tryptone (Oxoid L42); 0.5% (w/v) yeast extract (Oxoid L21); 0.25% (w/v) glucose)

Top agarose (0.7 g low-melting agarose added to 100 ml $dH_2O$, heated to melt, cooled to 45° C., dispensed into 3 ml volumes and autoclaved.)

SM buffer (2.92 g NaCl; 1 g $MgSO_4.7H_2O$; 25 ml 1M Tris-Cl pH7.5; 0.05 g Gelatin; Dissolved in 500 ml $dH_2O$ and autoclaved.)

2. Bacteriophage and Bacteria Collection 2.1 Sampling Method

The strains of *P. acnes* and phage isolates used in the screening were obtained from patients attending the Dermatology Department at the Leeds General Infirmary (except *P. acnes* NCTC737 and DSM16379). The method is based on that described in Williamson P. & Kligman A. M. (1965) *J. Invest. Dermatol.* 45: 498-503.

a) Place a sterile metal ring onto the surface of the skin and press to ensure a good seal;
b) Pipette 1 ml wash fluid (75 mM phosphate buffer, pH7.9) into the ring;
c) Gently scrub the surface of the skin for 1 min with a sterile Teflon rod;
d) Remove the wash fluid to a sterile bottle and replace with another 1 ml of sterile wash fluid;
e) Repeat scrubbing procedure then remove the fluid and pool with the first sample;
f) Plate serial dilutions (or spiral plate) of the sample onto RCA containing 6 µg $ml^{-1}$ furazolidone (which inhibits growth of *staphylococci* but not of *propionibacteria*) and incubate anaerobically for 7 days at 34° C.;
g) Recover individual bacterial colonies or bacteriophage plaques (using method 2.2 described below) and propagate by restreak (bacteria) or the method described below ('Preparation of phage stocks—lysate') for bacteriophage plaque.

2.2 Preparation of Phage Stocks—Plaque Pick a) Plate out phage-containing bacteria as described above and incubate for 24-48 h;
b) Pick 2-3 plugs of agar from a single plaque into 1 ml SM buffer in a screw-top vial using a glass Pasteur pipette;
c) Store at 4° C.

2.3 Preparation of Phage Stocks—Lysate a) Plate out phage-containing bacteria as described above and incubate for 24-48 h;
b) Overlay plate with 5 ml SM buffer and leave for 1 h at room temperature with occasional swirling;
c) Pipette buffer into a sterile tube (plastic universal or Falcon) then scrape top agarose off the plate into the tube;
d) Centrifuge at >5000 rpm for 10 min at 4° C.;
e) Remove supernatant and filter sterilise (0.2 µm filter);
f) Aliquot and store at 4° C.

3. Host Range Testing 3.1 Plating of *P. Acnes* Bacteriophage a) Melt top agarose in a 70° C. water bath then cool to 44° C.;
b) Centrifuge cultures of *P. acnes* at 5000 rpm for 10 min in a bench-top centrifuge;
c) Resuspend cells to an $OD_{600}$ of 2.5 in SM buffer;
d) Add 100 µl of *P. acnes* to an aliquot of phage (usually 5-10 µl) in a microcentrifuge tube, briefly mix and then incubate at 34° C. for 15 min;
e) Gently pipette the *P. acnes*/phage mixture into 3 ml top agarose and invert to mix;
f) Pour onto a dry RCA plate and swirl to cover surface;
g) Allow to set and incubate anaerobically at 34° C. for 24-48 h.

3.2 *P. Acnes* Bacteriophage Infectivity Assay a) Melt top agarose in a 70° C. water bath then cool to 44° C.;
b) Centrifuge cultures of *P. acnes* at 5000 rpm for 10 min in a bench-top centrifuge;
c) Resuspend cells to an $OD_{600}$ of 2.5 in SM buffer;
d) Add 100 µl of *P. acnes* to 3 ml top agarose and shake to mix;
e) Pour onto a dry RCA plate and swirl to cover surface;
f) Allow agarose to set then dry plate again for 15-20 min;
g) Spot 5 µl of each phage onto the plate;
h) Allow spots to soak in and incubate anaerobically at 34° C. for 48 h.

For high throughput screening of phage a multipoint inoculator can be used to apply phage spots to the surface of the plate.

3.3 Infectivity Assay of Bacteriophage Against Other Non-*P. Acnes* Species

The bacteriophage strains were also tested against other species of bacteria, using the method outlined above but substituting other species for *P. acnes*. The species of bacteria tested were *Propionibacterium granulosum, Propionibacterium avidum, Staphylococcus epidermidis* and *Corynebacterium bovis*.

3.4 Infectivity Assay of Bacteriophage 103672 on *P. Acnes* Immediately after Isolation from Skin of a Volunteer Natural *P. acnes* numbers on the volunteer's back were known to be approximately $10^6$ cfu $cm^{-2}$ ("cfu" denotes "colony forming units"). A scrub wash sample was taken from the back of the volunteer as set out in Method 2.1 above. A small aliquot was taken to determine the starting *P. acnes* count ($10^5$ cfu $cm^{-2}$). The rest of the sample was diluted 1:2 in 2×TYG broth (1× final TYG concentration) in order to grow the *P. acnes*. This was then further diluted in TYG to give 10-fold dilutions ranging from neat to $10^{-3}$. Two samples of each dilution were aliquoted, phage 103672 added to one ($10^6$ pfu $ml^{-1}$ final concentration, "pfu" denoting "plaque forming units") at a ratio of 6:1 phage:cell and SM added to the other as a control. These were then incubated anaerobically at 34° C. for 48 h.

Following incubation, each sample was diluted 10-fold from neat to $10^{-2}$, filtered and treated with 10 mM ferrous ammonium sulphate (FAS), a compound which can inactivate free phage and which, in this context, is used to prevent carry-over of free phage, which could give a false positive result. Filters were plated on RCA+furazolidone plates (RCAF) and incubated anaerobically at 34° C. for 6 days. At the end of this period, the number of colony forming units for $cm^3$ was determined, by counting the number of colonies on the filter and using this figure to calculate the cfu in the original, undiluted, sample.

4. Identification of Non-Lysogenic *P. Acnes* Bacteriophage

Bacteriophage were subjected to lysogeny and super-infection immunity testing as follows. Phage were spotted onto lawns of *P. acnes* AT1 to produce plaques and these were incubated for periods of time sufficient to allow growth of bacteria within plaques, such bacteria having developed resistance to phage infection. Resistance can develop through changes on the surface of the bacterial cell (e.g. receptor) or internally (e.g. restriction enzymes). However, lysogeny confers resistance to related phages in a process called "superinfection immunity". Repressor protein, expressed by the lysogen, prevents the integrated phage from synthesising the proteins necessary for reproduction. Repressor protein fulfils exactly the same function upon any homologous phage DNA coming into the cell, similarly preventing the production of phage. This can only happen if the incoming DNA is related to the lysogen such that the repressor can bind.

The centres of the turbid plaques were picked and streaked out to obtain single colonies of bacteria apparently resistant to infection by the phage, which may or may not have been lysogenic. At this stage, there was no way of knowing which mechanism of resistance, discussed above, had been acquired. Single colonies were picked and grown in tryptone/yeast extract/glucose (TYG) broth before plating as lawns in top agarose on reinforced clostridial agar (RCA) plates. First, spontaneous plaque formation was identified, indicating phage lysogeny as the result of earlier infection with a lysogenic phage. Second, phage were spotted onto the lawns to look for super-infection immunity to the same or other phage, an indication of lysogeny and/or resistance, since a plaque will form unless the bacteria are immune to infection by the particular phage. As outlined above, if they are immune to repeat infection by the same phage isolate, this suggests the presence of that phage in lysogenic phase in the cell. Similarly, if they are immune to infection by another phage isolate, this suggests the presence of the first phage in lysogenic phase in the cell. Phage which do not display such lysogenic qualities are considered to be suitable for use in embodiments of the invention.

Alternative methods of identifying whether a phage can become lysogenic are PCR detection using primers specific to, for example, the phage repressor DNA, where a positive PCR result would indicate the presence of phage repressor DNA and, therefore, that the bacteriophage in question had the ability to become lysogenic. Absence of a repressor gene is one way of avoiding lysogeny, but other deletions which would convert a lysogenic phage into a lytic phage would include any that removes other parts of the integration machinery, i.e. phage-encoded integrase proteins and DNA sequences required for insertion into host DNA (att sites). Any sort of error which inactivates these genes or sites will achieve the desired lytic phage phenotype, such as entire or partial removal of the gene/site and functionally inactivating point mutation(s). Alternatively, a PCR-based method could detect the ligated cos site in cells which have been exposed to a bacteriophage of interest. Another method would be Southern blotting using labelled phage DNA to probe lysogens in the bacterial genome. These and other such methods are easily within the ability of the skilled person, who would clearly understand how to approach such methods in order to reliably identify whether a phage can become lysogenic and whether, therefore, it falls within the scope of the present invention.

5. DNA Sequencing

Bacteriophage DNA was extracted and purified using the following method:
a) Prepare a plate lysate of the phage (10 ml)
b) Add NaCl to 1 M and PEG8000 to 10% (w/v) and dissolve slowly
c) Incubate on ice for 30 min to allow phage to precipitate
d) Harvest phage by centrifuging at 10,000 g for 10 min at 4° C.
e) Resuspend in 1 ml SM buffer
f) Add an equal volume of chloroform and vortex for 30 sec
g) Centrifuge at 3000 g for 15 min at 4° C.
h) Remove the upper layer containing phage to a sterile tube
i) Add proteinase K to 50 µg $ml^{-1}$ and SDS to 0.5% (w/v) and incubate at 56° C. for 1 hour
j) Cool, then extract twice with phenol:chloroform and once with chloroform
k) Precipitate DNA with 2 volumes of ethanol
l) Transfer DNA to 1 ml 70% (v/v) ethanol using a Pasteur pipette
m) Recover DNA by centrifugation at 12,000 g for 2 min, discard supernatant and redissolve the DNA in TE buffer or $dH_2O$ Sequencing was carried out by Lark Technologies Inc. (Houston, Tex.). PA6, 103609, 103672 and 1894 DNA was prepared as above and then used to prepare a shotgun library from which clones were sequenced to derive the full genome sequence for each bacteriophage.

6. ORF Analysis

Open reading frames (ORF) in several bacteriophage isolates were analysed using software available through GeneMark™, a family of gene prediction programs provided by Mark Borodovsky's Bioinformatics Group at the Georgia Institute of Technology, Atlanta, Ga. The ORF analysis tool there uses a heuristic approach to identifying possible genes using a computational method described in: Besemer J. and Borodovsky M. (1999) *Nucl. Acids Res.* 27: 3911-3920. The program can be found on the Internet at: http://opal.biology.gatech.edu/GeneMark/heuristic_hmm2.cgi Gene product functions were determined by database comparison using the Blast analysis tool at http://www.ncbi.nlm.nih.gov/BLAST/.

Results

I. Testing of Bacteriophage Against Stock *P. Acnes* Strains

A collection of 46 independent bacteriophage isolates were tested against a panel of 21 *P. acnes* strains chosen for their diversity in age, origin and drug resistance profiles (listed in Table 1).

TABLE 1

List of strains used in bacteriophage host range screening tests.

| Strain number | Bacterial isolate |
|---|---|
| 1 | P37 |
| 2 | AT1 |
| 3 | NCTC737 |
| 4 | PF276 |
| 5 | PF286 |
| 6 | P506 |
| 7 | CavillA |
| 8 | CavillB |
| 9 | AT4 |
| 10 | AT5 |
| 11 | 101842c |
| 12 | 101845a |
| 13 | 101845b |
| 14 | 101846c |
| 15 | 101847a |
| 16 | 101848 |
| 17 | 101849 |
| 18 | 101850a |
| 19 | 101850b |
| 20 | 101851a |
| 21 | DSM16379 |

The ability of each bacteriophage to lyse each bacterial strain was tested to give an indication of the breadth of host specificity of each phage. The results in Table 2 show that, in general, all phages had broad specificity. Of these, 14 were able to infect all strains tested: PA6, 103609, 103625, 103629, 103664, 103672, 103715, 1869, 1874, 1878, 1894, 1905, 1909 and P37P.

TABLE 2

Summary of results from bacteriophage host range testing.

| Phage Isolate | \multicolumn{21}{c}{P. acnes strain} |
|---|---|

| Phage Isolate | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|
| PA6    | + | + | + | + | + | + | + | + | + | + | + | + | + | + | + | + | + | + | + | + | + |
| 103205 | − | + | + | − | + | + | + | + | + | + | + | + | + | + | − | + | + | + | + | + | + |
| 103600 | − | + | + | − | + | + | + | + | + | + | + | + | + | + | + | + | + | + | + | + | + |
| 103601 | − | + | + | − | + | + | + | + | + | + | + | + | + | + | + | + | + | + | + | + |   |
| 103609 | + | + | + | + | + | + | + | + | + | + | + | + | + | + | + | + | + | + | + | + | + |
| 103611 | + | + | + | + | + | + | + | + | + | + | + | + | + | + | + | + | + | + | + | + |   |
| 103614 | + | + | + | − | + | + | + | + | + | + | + | + | + | + | − | + | + | + | + | + |   |
| 103625 | + | + | + | + | + | + | + | + | + | + | + | + | + | + | + | + | + | + | + | + | + |
| 103629 | + | + | + | + | + | + | + | + | + | + | + | + | + | + | + | + | + | + | + | + | + |
| 103657 | − | + | + | − | + | + | + | + | − | + | + | + | + | + | + | + | + | + | + | + |   |
| 103664 | + | + | + | + | + | + | + | + | + | + | + | + | + | + | + | + | + | + | + | + | + |
| 103666 | + | + | + | + | + | + | + | + | + | + | + | + | + | + | + | + | + | + | + | + | − |
| 103671 | + | + | + | + | + | + | + | + | + | + | + | + | + | + | + | + | + | + | + | + | − |
| 103672 | + | + | + | + | + | + | + | + | + | + | + | + | + | + | + | + | + | + | + | + | + |
| 103683 | + | + | + | + | + | + | + | + | + | + | + | + | + | + | + | + | + | + | + | + |   |
| 103695 | + | + | + | + | + | + | + | + | + | + | + | + | + | + | + | + | + | + | + | + | − |
| 103698 | − | + | + | − | + | + | + | − | + | + | + | + | + | − | + | + | + | + | + | + |   |
| 103704 | + | + | + | + | + | + | + | + | + | + | + | + | + | + | + | + | + | + | + | + | − |
| 103713 | + | + | + | + | + | + | + | + | + | + | + | + | + | + | + | + | + | + | + | + | − |
| 103715 | + | + | + | + | + | + | + | + | + | + | + | + | + | + | + | + | + | + | + | + | + |
| 138    | − | + | + | + | + | + | + | + | + | + | + | + | + | + | + | + | + | + | + | + |   |
| 139    | − | + | + | − | + | + | + | + | + | + | + | + | + | + | − | + | + | + | + | + |   |
| 140    | − | + | + | − | + | + | + | − | + | + | + | + | + | + | − | + | + | + | + | + |   |
| 1869   | + | + | + | + | + | + | + | + | + | + | + | + | + | + | + | + | + | + | + | + | + |
| 1874   | + | + | + | + | + | + | + | + | + | + | + | + | + | + | + | + | + | + | + | + | + |
| 1877   | − | + | + | − | + | + | + | + | + | + | + | + | + | + | − | + | + | + | + | + |   |
| 1878   | + | + | + | + | + | + | + | + | + | + | + | + | + | + | + | + | + | + | + | + | + |
| 1880   | − | + | + | − | + | + | + | + | + | + | + | + | + | + | − | + | + | + | + | + |   |
| 1881   | − | + | + | − | + | + | + | + | − | + | + | + | + | + | − | + | + | + | + | + |   |
| 1883   | − | + | + | + | + | + | + | + | + | + | + | + | + | + | + | + | + | + | + | + |   |
| 1885   | + | + | + | + | + | + | + | + | + | + | + | + | + | + | + | + | + | + | + | + | − |
| 1888   | − | + | + | − | + | + | + | + | + | + | + | + | + | + | − | + | + | + | + | + |   |
| 1894   | + | + | + | + | + | + | + | + | + | + | + | + | + | + | + | + | + | + | + | + | + |
| 1895   | − | + | + | + | + | + | + | + | + | + | + | + | + | + | − | + | + | + | + | + |   |
| 1900   | − | + | + | − | + | + | + | + | + | + | + | + | + | + | + | + | + | + | + | + |   |
| 1901   | − | + | + | + | + | + | + | − | + | + | + | + | + | + | + | + | + | + | + | + |   |
| 1902   | − | + | + | − | + | + | + | + | + | + | + | + | + | + | − | + | + | + | + | + |   |
| 1905   | + | + | + | + | + | + | + | + | + | + | + | + | + | + | + | + | + | + | + | + | + |
| 1909   | + | + | + | + | + | + | + | + | + | + | + | + | + | + | + | + | + | + | + | + | + |
| 1922   | − | + | + | − | + | + | + | + | + | + | + | + | + | + | − | + | + | + | + | + |   |
| 1923   | − | + | + | − | + | + | + | + | + | + | + | + | + | + | + | + | + | + | + | + |   |
| 1925   | + | + | + | + | + | + | + | + | + | + | + | + | + | + | + | + | + | + | + | + | − |
| 1928   | − | + | + | − | + | + | + | + | + | + | + | + | + | + | − | + | + | + | + | + |   |
| 1929   | − | + | + | − | + | + | + | + | + | + | + | + | + | + | − | + | + | + | + | + |   |
| P37P   | + | + | + | + | + | + | + | + | + | + | + | + | + | + | + | + | + | + | + | + | + |

"+" denotes a positive reaction where bacteriophage is able to infect the host after applying neat phage stock to a seeded lawn of host bacteria in agar overlay.
"−" denotes a negative reaction where no infection was evident.

None of these strains showed an ability to infect the *P. granulosum, P. avidum, S. epidermidis* and *C. bovis* species tested.

II. Testing of Bacteriophage PA6, 103609, 103625, 103629, 103664, 103672, 103715, 1869, 1874, 1878, 1894, 1905, 1909 and P37P Against *P. Acnes* Isolated From Volunteers' Skin The 14 strains, shown above to have broad specificity, were further tested against 31 additional *P. acnes* strains, isolated from the skin of volunteers. The bacteriophage all showed lytic activity against these additional strains, as shown in Table 3:

TABLE 3

Summary of results from bacteriophage host range testing.

| Phage isolate | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|
| PA6 | + | + | + | + | + | + | + | + | + | + | + | + | + | + | + | + |
| P37P | + | + | + | + | + | + | + | + | + | + | + | + | + | + | + | + |
| 1869 | + | + | + | + | + | + | + | + | + | + | + | + | + | + | + | + |
| 1874 | + | + | + | + | + | + | + | + | + | + | + | + | + | + | + | + |
| 1878 | + | + | + | + | + | + | + | + | + | + | + | + | + | + | + | + |
| 1894 | + | + | + | + | + | + | + | + | + | + | + | + | + | + | + | + |
| 1905 | + | + | + | + | + | + | + | + | + | + | + | + | + | + | + | + |
| 1909 | + | + | + | + | + | + | + | + | + | + | + | + | + | + | + | + |
| 103609 | + | + | + | + | + | + | + | + | + | + | + | + | + | + | + | + |
| 103625 | + | + | + | + | + | + | + | + | + | + | + | + | + | + | + | + |
| 103629 | + | + | + | + | + | + | + | + | + | + | + | + | + | + | + | + |
| 103664 | + | + | + | + | + | + | + | + | + | + | + | + | + | + | + | + |
| 103672 | + | + | + | + | + | + | + | + | + | + | + | + | + | + | + | + |
| 103715 | + | + | + | + | + | + | + | + | + | + | + | + | + | + | + | + |

| Phage isolate | 38 | 39 | 40 | 41 | 42 | 43 | 44 | 45 | 46 | 47 | 48 | 49 | 50 | 51 | 52 |
|---|---|---|---|---|---|---|---|---|---|---|---|---|---|---|---|
| PA6 | + | + | + | + | + | + | + | + | + | + | + | + | + | + | + |
| P37P | + | + | + | + | + | + | + | + | + | + | + | + | + | + | + |
| 1869 | + | + | + | + | + | + | + | + | + | + | + | + | + | + | + |
| 1874 | + | + | + | + | + | + | + | + | + | + | + | + | + | + | + |
| 1878 | + | + | + | + | + | + | + | + | + | + | + | + | + | + | + |
| 1894 | + | + | + | + | + | + | + | + | + | + | + | + | + | + | + |
| 1905 | + | + | + | + | + | + | + | + | + | + | + | + | + | + | + |
| 1909 | + | + | + | + | + | + | + | + | + | + | + | + | + | + | + |
| 103609 | + | + | + | + | + | + | + | + | + | + | + | + | + | + | + |
| 103625 | + | + | + | + | + | + | + | + | + | + | + | + | + | + | + |
| 103629 | + | + | + | + | + | + | + | + | + | + | + | + | + | + | + |
| 103664 | + | + | + | + | + | + | + | + | + | + | + | + | + | + | + |
| 103672 | + | + | + | + | + | + | + | + | + | + | + | + | + | + | + |
| 103715 | + | + | + | + | + | + | + | + | + | + | + | + | + | + | + |

"+" denotes a positive reaction where bacteriophage is able to infect the host after applying neat phage stock to a seeded lawn of host bacteria in agar overlay.
"−" denotes a negative reaction where no infection was evident.

III. Identification of Non-Lysogenic *P. Acnes* Bacteriophage

Phage were screened for lysogenic activity as outlined in Method 4 above. Three of the broad host range phage listed in Table 3 above showed no evidence of lysogeny or resistance in these experiments, as outlined in Method 4 above, with results shown in Table 4. They were phages 1894, 103609 and 103672.

TABLE 4

Data from repeated attempts to demonstrate lysogenic potential in phage. Phage infections (left column) of P. acnes strain AT1 were incubated for prolonged periods such that growth was visible within plaques. These emergent bacteria were sampled and tested for their susceptibility to infection with homologous or heterologous phage (top row). 'N' indicates resistance and therefore demonstration of lysogenic activity. Three strains 1894, 103609 and 103672 (underlined) failed to demonstrate lysogenic activity.

| Potential Lysogen | PA6 | P37P | 1869 | 1874 | 1878 | 1894 | 1905 | 1909 | 103609 | 103625 | 103629 | 103664 | 103672 | 103715 |
|---|---|---|---|---|---|---|---|---|---|---|---|---|---|---|
| PA6 | N | N | N | N | N | Y | N | Y | Y | N | N | N | Y | N |
| P37P | N | N | N | N | N | Y | N | Y | Y | N | N | N | Y | N |
| 1869 | Y | Y | Y | Y | Y | Y | Y | Y | Y | Y | Y | Y | Y | Y |
| 1874 | Y | Y | N | Y | Y | Y | Y | Y | Y | Y | Y | Y | Y | Y |
| 1878 | N | N | Y | N | N | Y | N | Y | Y | N | N | N | Y | N |
| 1894 | Y | Y | Y | Y | Y | Y | Y | Y | Y | Y | Y | Y | Y | Y |
| 1905 | N | N | N | N | N | Y | N | Y | Y | N | N | N | Y | N |
| 1909 | N | N | N | N | N | Y | N | N | Y | N | N | N | Y | N |

TABLE 4-continued

Data from repeated attempts to demonstrate lysogenic potential in phage. Phage infections (left column) of P. acnes strain AT1 were incubated for prolonged periods such that growth was visible within plaques. These emergent bacteria were sampled and tested for their susceptibility to infection with homologous or heterologous phage (top row). 'N' indicates resistance and therefore demonstration of lysogenic activity. Three strains 1894, 103609 and 103672 (underlined) failed to demonstrate lysogenic activity.

| Potential Lysogen | PA6 | P37P | 1869 | 1874 | 1878 | 1894 | 1905 | 1909 | 103609 | 103625 | 103629 | 103664 | 103672 | 103715 |
|---|---|---|---|---|---|---|---|---|---|---|---|---|---|---|
| 103609 | Y | Y | Y | Y | Y | Y | Y | Y | Y | Y | Y | Y | Y | Y |
| 103625 | N | Y | N | N | Y | Y | Y | Y | Y | Y | Y | Y | Y | N |
| 103629 | N | Y | N | N | N | Y | N | N | Y | N | N | N | Y | N |
| 103664 | N | Y | N | N | N | Y | N | Y | Y | N | N | Y | Y | N |
| 103672 | Y | Y | Y | Y | Y | Y | Y | Y | Y | Y | Y | Y | Y | Y |
| 103715 | N | Y | N | N | N | Y | Y | Y | Y | N | Y | Y | Y | N |

IV. DNA Sequencing

The genome for each of bacteriophages PA6, 103609, 103672 and 1894 was sequenced as outlined in Method 5 above. The sequences for each are shown in SEQ ID NO:1 (PA6), SEQ ID NO:3 (103609), SEQ ID NO:4 (103672) and SEQ ID NO:5 (1894).

V. ORF Analysis of Bacteriophage Genomes

Analysis of open reading frames (ORF) within the PA6 genome and subsequent analysis of predicted protein sequences using the Blast database analysis tool identified various potential genes and highlighted possible functions (summary of analysis shown in FIG. 1). The 5' end of the phage genome appears to host many of the structural genes which comprise the phage coat and tail. Notable among the remaining genes is a potential lysin (ORF 20) which shares homology with other lysins and an amidase protein within the P. acnes genome itself. The DNA sequence of this gene is shown in SEQ ID NO:2 and can be seen at nucleotides 15371-16233 of SEQ ID NO:1.

Figure 2:
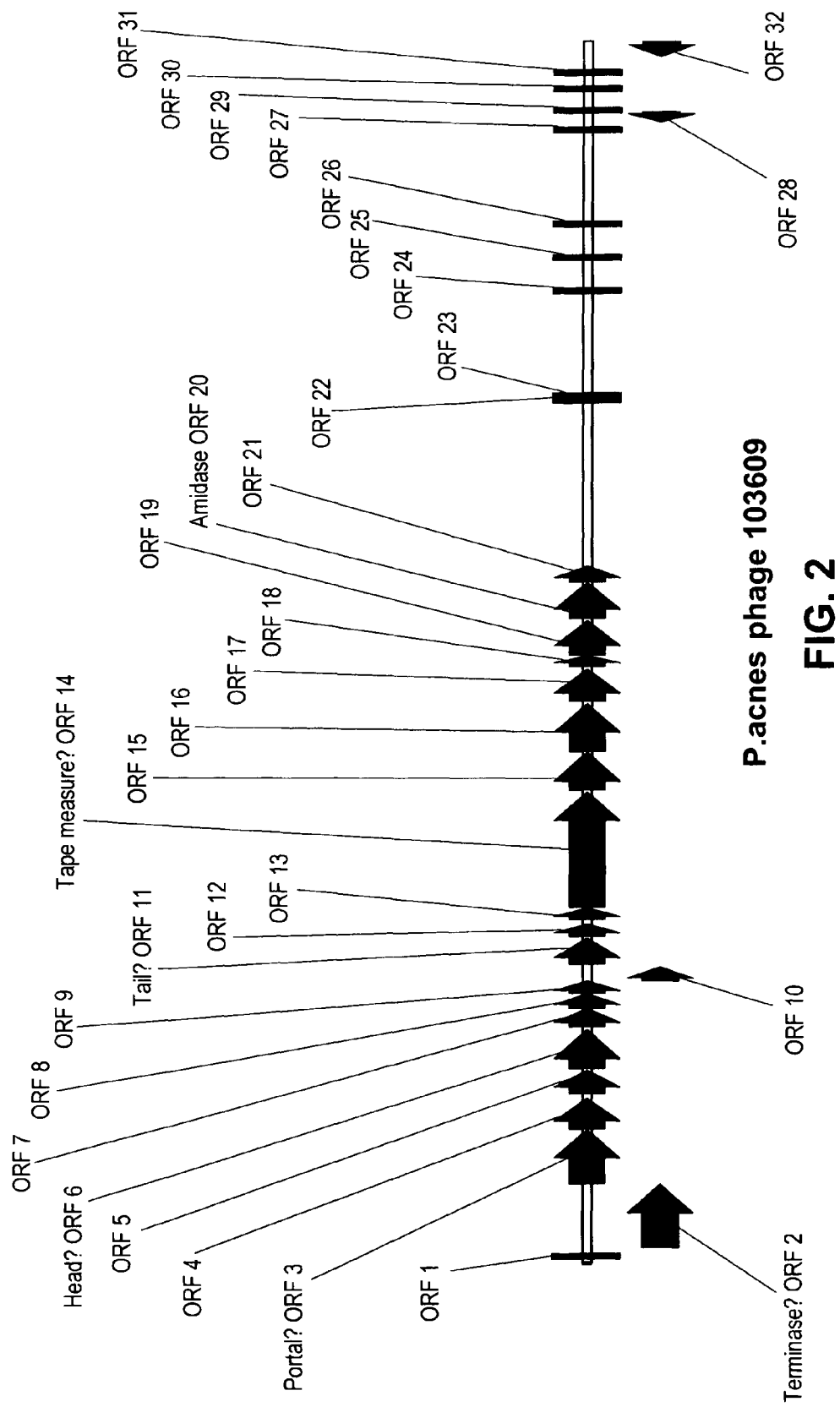
FIG. 2 shows the arrangement of open reading frames (ORFs) in the 103609 genome, with putative functions of various ORFs indicated.
Figure 3:
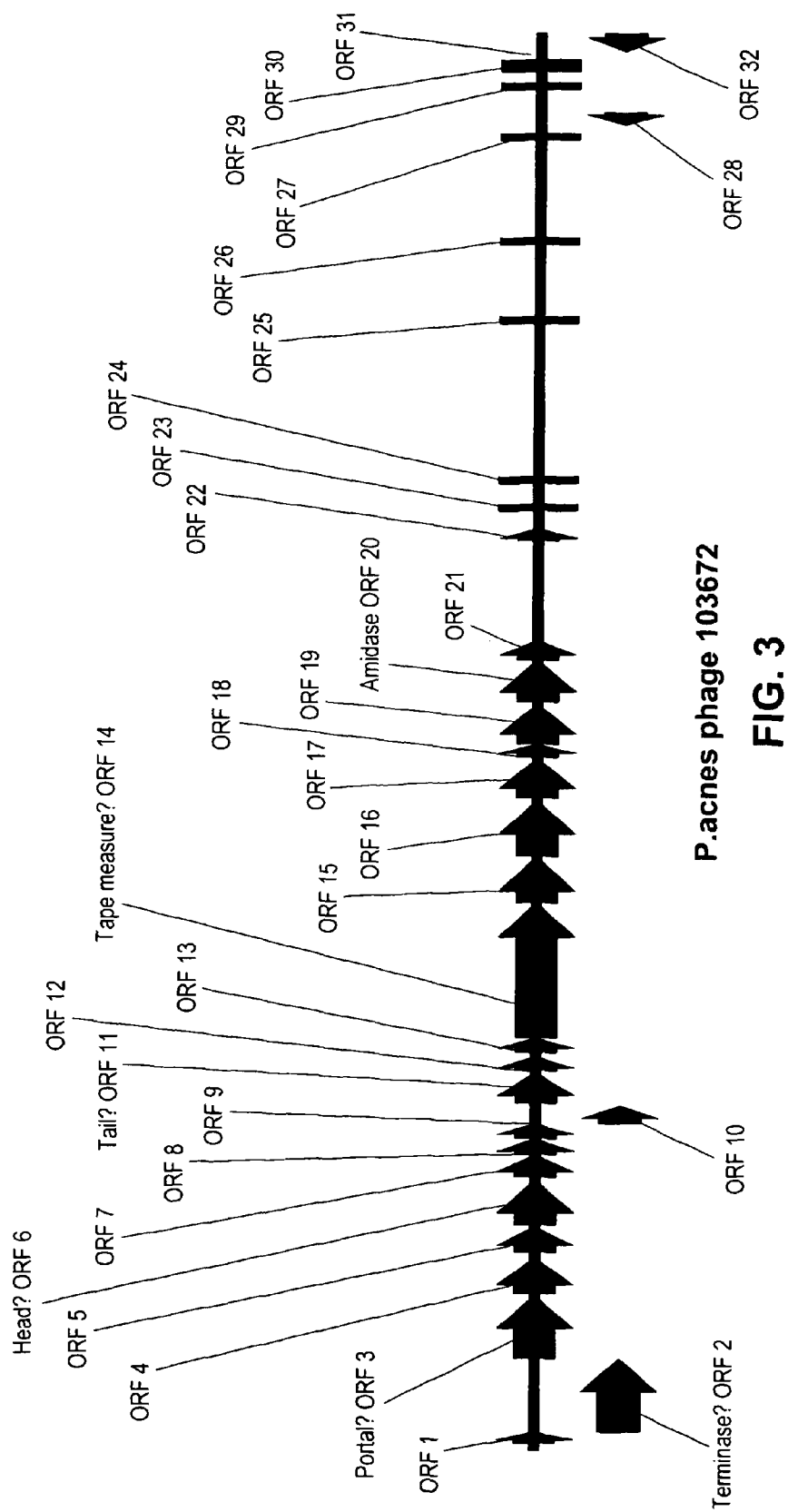
FIG. 3 shows the arrangement of open reading frames (ORFs) in the 103672 genome, with putative functions of various ORFs indicated.
Figure 4:
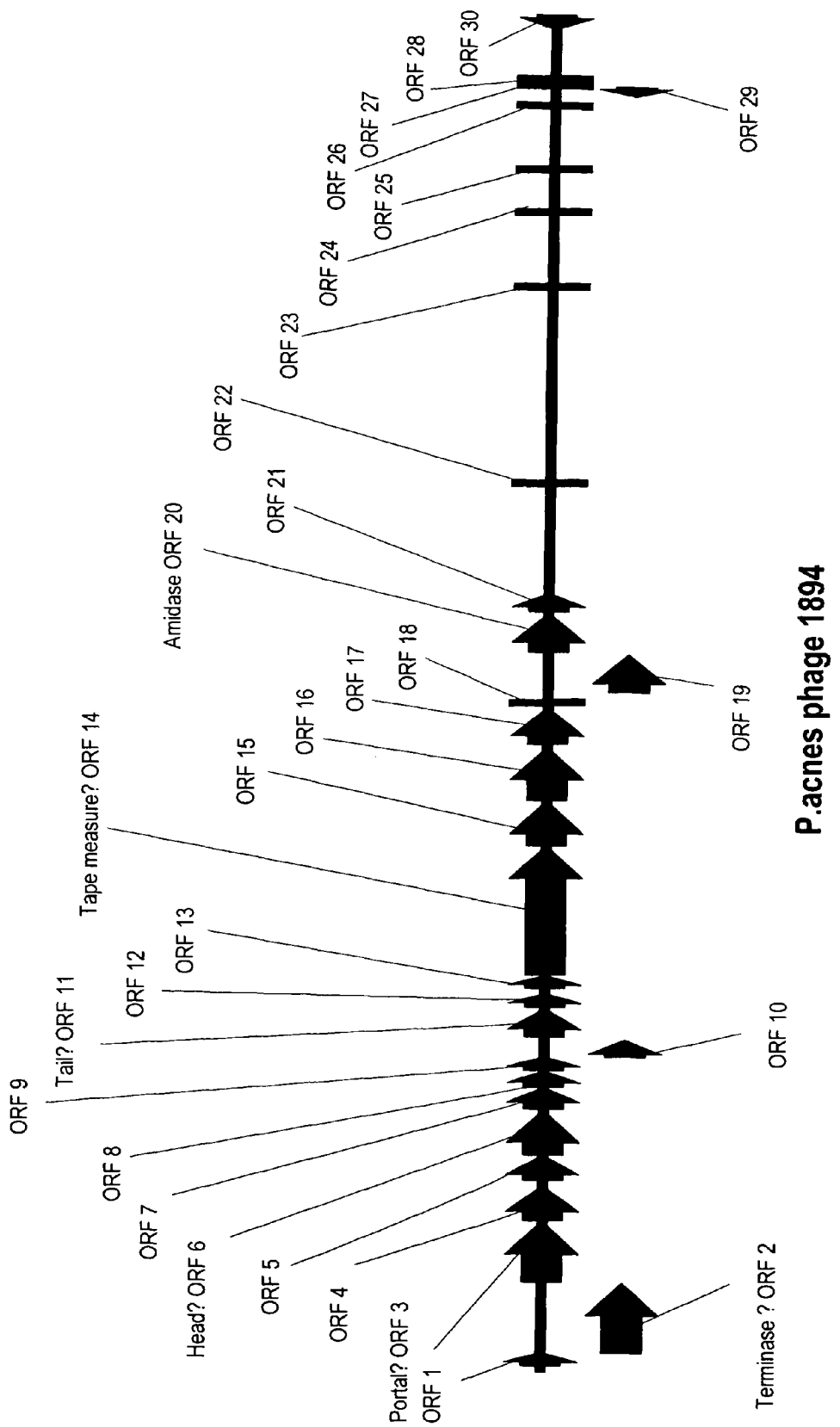
FIG. 4 shows the arrangement of open reading frames (ORFs) in the 1894 genome, with putative functions of various ORFs indicated.

A similar analysis was carried out for the genomes of 103609, 103672 and 1894, with the summary shown in FIG. 2 (103609), FIG. 3 (103672), FIG. 4 (1894) and Table 5. Again, ORF 20 in each case encodes a potential lysin. The DNA sequence for this gene is shown in SEQ ID NO: 6 (phage 103609, nucleotides 15442-16296 of SEQ ID NO: 3), SEQ ID NO:7 (phage 103672, nucleotides 15382-16245 of SEQ ID NO: 4) and SEQ ID NO:8 (phage 1894, nucleotides 15416-16273 of SEQ ID NO: 5). The boundaries for each ORF for each bacteriophage strain are shown in Table 5. No repressor protein is obvious from sequence homology analysis in these phage strains and this is an indication that these are purely lytic phage, unable to sustain lysogeny, as supported by the results shown in Table 4. Therefore, this confirms that these phage strains are ideal in this respect as candidates for phage therapy.

TABLE 5A

ORF boundaries for phage 103609, 103672 and 1894
(−) indicates that the ORF is coded on the reverse DNA strand

| 1894 ORFs (30 total) | 103609 ORFs (32 total) | 103672 ORFs (32 total) |
|---|---|---|
| ORF 1 Start: 53 End: 361 | ORF 1 Start: 145 End: 363 | ORF 1 Start: 113 End: 361 |
| ORF 2 Start: 361 End: 1872 | ORF 2 Start: 363 End: 1874 | ORF 2 Start: 361 End: 1872 |
| ORF 3 Start: 1869 End: 3194 | ORF 3 Start: 1871 End: 3196 | ORF 3 Start: 1869 End: 3194 |
| ORF 4 Start: 3201 End: 3956 | ORF 4 Start: 3203 End: 3958 | ORF 4 Start: 3198 End: 3953 |
| ORF 5 Start: 4067 End: 4621 | ORF 5 Start: 4069 End: 4629 | ORF 5 Start: 4057 End: 4611 |
| ORF 6 Start: 4628 End: 5575 | ORF 6 Start: 4636 End: 5583 | ORF 6 Start: 4618 End: 5565 |
| ORF 7 Start: 5620 End: 6081 | ORF 7 Start: 5627 End: 6088 | ORF 7 Start: 5613 End: 6074 |
| ORF 8 Start: 6083 End: 6430 | ORF 8 Start: 6090 End: 6437 | ORF 8 Start: 6076 End: 6422 |
| ORF 9 Start: 6437 End: 6727 | ORF 9 Start: 6444 End: 6734 | ORF 9 Start: 6430 End: 6720 |
| ORF 10 Start: 6724 End: 7095 | ORF 10 Start: 6731 End: 7102 | ORF 10 Start: 6717 End: 7087 |
| ORF 11 Start: 7147 End: 7776 | ORF 11 Start: 7154 End: 7795 | ORF 11 Start: 7140 End: 7769 |
| ORF 12 Start: 7803 End: 8099 | ORF 12 Start: 7824 End: 8120 | ORF 12 Start: 7797 End: 8093 |
| ORF 13 Start: 8198 End: 8485 | ORF 13 Start: 8219 End: 8506 | ORF 13 Start: 8192 End: 8479 |
| ORF 14 Start: 8493 End: 11258 | ORF 14 Start: 8514 End: 11279 | ORF 14 Start: 8487 End: 11252 |
| ORF 15 Start: 11274 End: 12215 | ORF 15 Start: 11295 End: 12236 | ORF 15 Start: 11270 End: 12211 |
| ORF 16 Start: 12223 End: 13380 | ORF 16 Start: 12244 End: 13401 | ORF 16 Start: 12219 End: 13376 |
| ORF 17 Start: 13430 End: 14218 | ORF 17 Start: 13451 End: 14239 | ORF 17 Start: 13425 End: 14213 |

TABLE 5B

ORF boundaries for phage 103609, 103672 and 1894
(−) indicates that the ORF is coded on the reverse DNA strand

| 1894 ORFs (30 total) | 103609 ORFs (32 total) | 103672 ORFs (32 total) |
|---|---|---|
| ORF 18 Start: 14299 End: 14538 | ORF 18 Start: 14296 End: 14559 | ORF 18 Start: 14259 End: 14522 |
| ORF 19 Start: 14541 End: 15374 | ORF 19 Start: 14563 End: 15387 | ORF 19 Start: 14525 End: 15340 |
| ORF 20 Start: 15416 End: 16273 | ORF 20 Start: 15442 End: 16296 | ORF 20 Start: 15382 End: 16245 |
| ORF 21 Start: 16286 End: 16684 | ORF 21 Start: 16309 End: 16707 | ORF 21 Start: 16258 End: 16656 |
| ORF 22 Start: 19047 End: 19103 | ORF 22 Start: 20662 End: 20766 | ORF 22 Start: 18710 End: 18955 |
| ORF 23 Start: 23248 End: 23391 | ORF 23 Start: 20767 End: 20919 | ORF 23 Start: 19393 End: 19497 |
| ORF 24 Start: 24869 End: 25012 | ORF 24 Start: 23272 End: 23415 | ORF 24 Start: 19946 End: 20044 |
| ORF 25 Start: 25760 End: 25810 | ORF 25 Start: 24093 End: 24293 | ORF 25 Start: 23239 End: 23382 |
| ORF 26 Start: 27128 End: 27172 (−) | ORF 26 Start: 24899 End: 25042 | ORF 26 Start: 24863 End: 25006 |
| ORF 27 Start: 27340 End: 27582 (−) | ORF 27 Start: 27152 End: 27196 (−) | ORF 27 Start: 27006 End: 27164 |
| ORF 28 Start: 27586 End: 27708 (−) | ORF 28 Start: 27326 End: 27583 (−) | ORF 28 Start: 27268 End: 27522 (−) |
| ORF 29 Start: 27721 End: 27888 | ORF 29 Start: 27593 End: 27715 (−) | ORF 29 Start: 28059 End: 28133 (−) |
| ORF 30 Start: 28743 End: 29108 (−) | ORF 30 Start: 28126 End: 28200 (−) | ORF 30 Start: 28424 End: 28465 (−) |
| | ORF 31 Start: 28528 End: 28569 (−) | ORF 31 Start: 28534 End: 28683 (−) |
| | ORF 32 Start: 28891 End: 29274 (−) | ORF 32 Start: 28779 End: 29153 (−) |

The % sequence identity of the DNA sequences in the ORFs between the three bacteriophage is shown in Table 6:

TABLE 6

% sequence identity of each ORF between the three phage 103609, 103672 & 1894;

| ORF | Identity (%) |
|---|---|
| 1 | 62.7* |
| 2 | 90.3 |
| 3 | 90.0 |
| 4 | 90.0 |
| 5 | 88.6 |
| 6 | 91.9 |
| 7 | 95.2 |
| 8 | 93.1 |
| 9 | 94.8 |
| 10 | 90.8 |
| 11 | 92.5 |
| 12 | 96.3 |
| 13 | 98.6 |
| 14 | 90.1 |
| 15 | 92.7 |
| 16 | 93.5 |
| 17 | 96.5 |
| 18 | 66.9 |
| 19 | 79.7 |
| 20 | 87.4 |
| 21 | 85.2 |
| 22 | 96.4 |
| 23 | 97.2 |
| 24 | 92.3 |
| 25 | 86.0 |
| 26 | 62.2 |
| 27 | 79.8 |
| 28 | 77.9 |
| 29 | 65.9 |
| 30 | 86.8 |

TABLE 6-continued

% sequence identity of each ORF between the three phage 103609, 103672 & 1894;

| ORF | Identity (%) |
|---|---|
| 31 | — |
| 32 | — |

*ORF1 for 1894 is over 100 nucleotides longer than for either 103609 or 103672.

Figure 5:
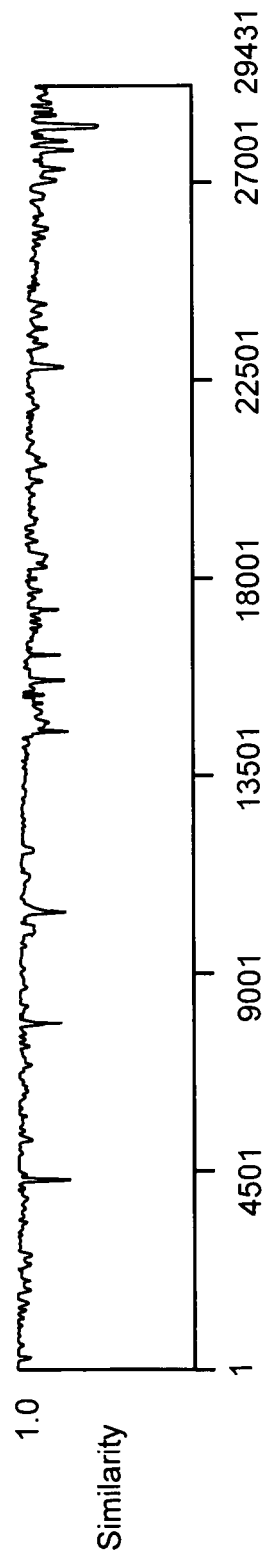
FIG. 5 shows a graphical representation of DNA sequence alignment of phages 103672, 103609 and 1894.

FIG. 5 shows the outcome of a sequence homology analysis between 103609, 103672 and 1894, in which similarity level of 1.0 indicates 100% identity, with similarity falling according to the nature and number of differences between the three sequences. This analysis demonstrates that overall sequence identity between all of these three phage is 86.1%.

Figure 6:
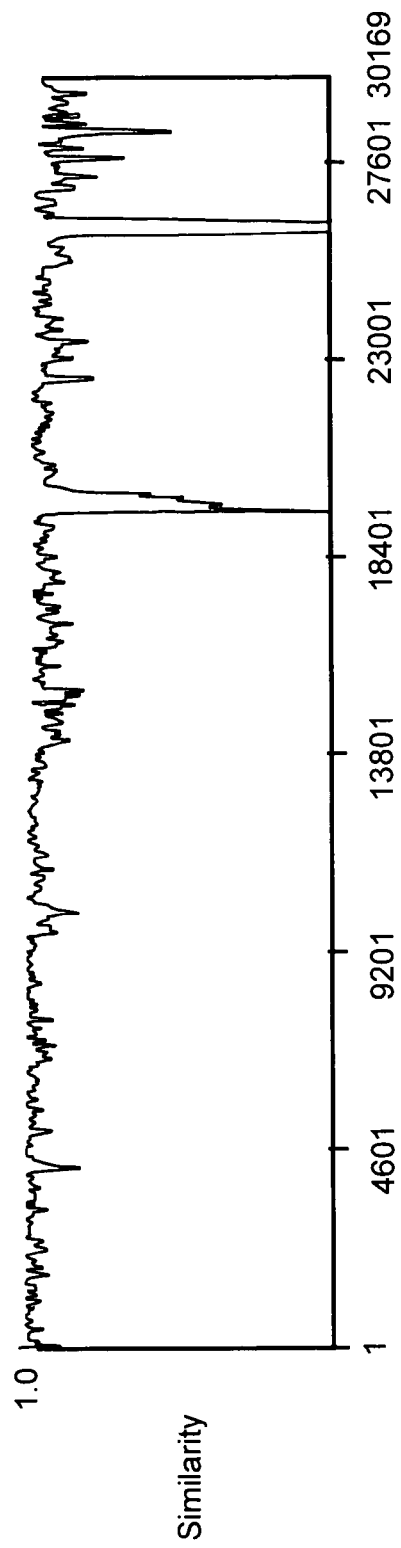
FIG. 6 shows a graphical representation of DNA sequence alignment of PA6 versus 103672, 103609 and 1894.

FIG. 6 shows the results of a similar analysis between these three phage and PA6, a bacteriophage which does not show the desired characteristic of being incapable of sustaining lysogeny in a bacterium (see results Section III above). This analysis demonstrates that overall sequence identity between all of these four phage is 80.1%. Overall sequence identity between 1894 and PA6 is 87.4%, between 103609 and PA6 is 86.8% and between 103672 and PA6 is 87.3%.

Figure 7:
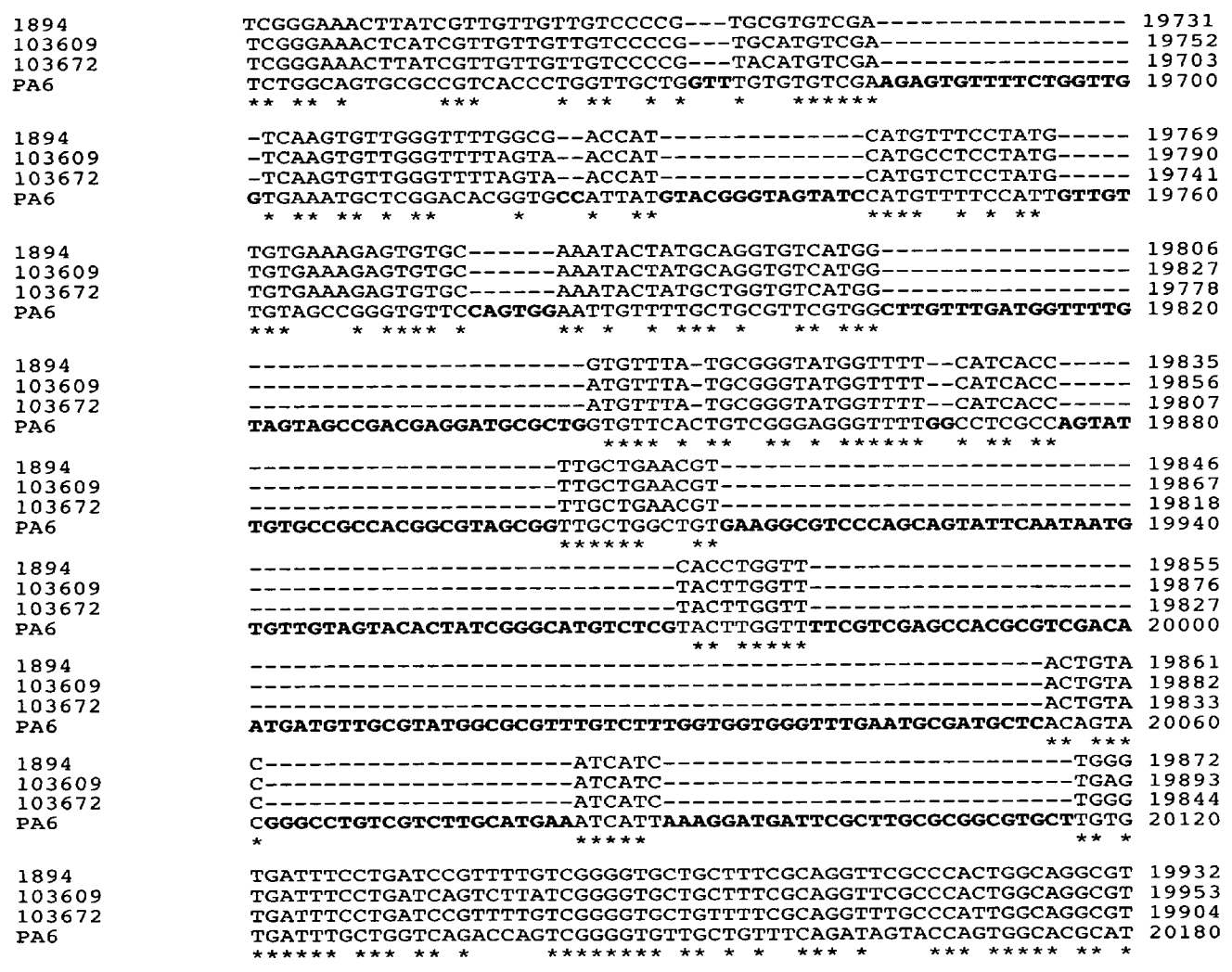

FIG. 6 clearly shows that there are two regions of low or zero % sequence identity when the DNA sequences of the three phage 103609, 103672 and 1894 are compared to that of PA6. FIGS. 7 and 8 show that this is the result of the presence of nucleotide sequences in PA6 which are not present in any of the other three phage.

Referring to nucleotide sequence numbering according to that shown in FIGS. 7 and 8, nucleotides 19804-19843 of PA6 are shown as SEQ ID NO: 9; nucleotides 19876-19901 of PA6 are shown as SEQ ID NO:10; nucleotides 19913-19969 of PA6 are shown as SEQ ID NO:11; nucleotides 19979-20054 of PA6 are shown as SEQ ID NO:12; and nucleotides 26242-26620 of PA6 are shown as SEQ ID NO:13.

Without wishing to be bound by theory, although these DNA inserts are present in PA6 in non-ORF regions of the genome, the presence of such large additional DNA inserts could have an effect on the overall structure of the genome and could affect, for example, the efficacy of expression of the ORF regions.

VI. Utilising Bacteriophage 103672 as an Anti-*P. Acnes* Treatment

Bacteriophage 103672 was tested against *P. acnes* bacteria immediately after isolation of the bacteria from a volunteer's skin, as outlined in Method 3.4 above. The results are as shown in Table 7:

TABLE 7

Results of incubation of *P. acnes* isolated from the skin of a volunteer, in the absence or presence of bacteriophage 103672

| Initial propionibacterial count, cfu ml$^{-1}$ (Phage:cell ratio) | Final count, cfu cm$^{-2}$ (control) | Final count, cfu cm$^{-2}$ (+103672) |
|---|---|---|
| $1.585 \times 10^5$ (6:1) | Too much growth to quantify | 0 |

This clearly shows the efficacy of the bacteriophage against *P. acnes* directly isolated from the skin of the patients and demonstrates the usefulness of such bacteriophage as an anti-*P. acnes* agent, whether directly within a method of treatment of acne or as an ingredient in a medicament for use in such a method.

The invention claimed is:

1. An isolated bacteriophage capable of lysing a *P. acnes* bacterium and incapable of lysing any bacterium which is not *P. acnes*, and which is incapable of sustaining lysogeny in a bacterium, wherein the bacteriophage has a genome which comprises the DNA sequence of SEQ ID NO:4; or wherein the bacteriophage is 103672 (Accession no. NCIMB 41351).

2. The bacteriophage of claim 1, further comprising a marker molecule.

3. A composition comprising at least one bacteriophage of claim 1 and an adjuvant, carrier or vehicle.

4. The composition of claim 3, further comprising at least one different bacteriophage.

5. The composition of claim 3 in a form suitable for oral, intravenous or topical administration.

6. The composition of claim 3, further comprising at least one further agent selected from antibiotics, anti-comedonals, anti-*P. acnes* agents, anti-inflammatories and anti-seborrhoeics.

7. An isolated polynucleotide having the nucleotide sequence of the genome of a bacteriophage of claim 1.

8. The isolated polynucleotide of claim 7, further comprising a sequence encoding a marker molecule.

9. A method of preventing or treating acne comprising administering an effective amount of at least one bacteriophage of claim 1 or the composition of claim 3 to an individual in need of such prevention or treatment.

10. A method of improving the appearance of an individual comprising administering to the individual an effective amount of at least one bacteriophage of claim 1.

11. A method of improving the appearance of an individual comprising administering to the individual an effective amount of the composition of claim 3.

* * * * *

SEQUENCE LISTING

```
<160> NUMBER OF SEQ ID NOS: 13

<210> SEQ ID NO 1
<211> LENGTH: 29739
<212> TYPE: DNA
<213> ORGANISM: Bacteriophage PA6

<400> SEQUENCE: 1
agtgaaatac ctcccttttg tggttttgtc tgtttgtcga cttttgtgt tggtggtgag      60 tgttgtgcag cctgagcttc ctgagtctcg tgagtggtgt ggggagacgc gtcgttggtg     120
gcgtgtgtgg ggtgaggata gtcgcgcgcc gtatgtgtct gatgaggagt ggttgtttct     180
tatggatgct gcggtgattc atgattgtgt gtggcgtgag ggtcgcgcgg atttggtggc     240
ttcgcttcgt gcgcatgtga aggcttttat gggcatgttg gataggtatt cggttgatgt     300
ggcgtctggt ggccgtggtg ggggttctgc tgtggcgatg attgaccggt ataggaagcg     360
taggggggct tgagtaggtg tctggtgttg ttgggtctca ggttcctcgt caccgtgtgg     420
ctgcggcgta ttcggtgtct gctgggggtg atgctgggga gcttggtcgt gcgtatgggt     480
tgacgcctga tccgtggcag cagcaggtgt tggatgattg gctggctgtc ggtagcaatg     540
gcaggcttgc ttctggtgtg tgtggggtgt ttgttccgcg gcagaatggc aagaatgcta     600
ttttggagat tgtggagttg tttaaggcga ctattcaggg tcgccgtatt ttgcatacgg     660
ctcacgagtt gaagtcggct cgtaaggcgt ttatgcggtt gaggtcgttt tttgagaatg     720
agcggcagtt tcctgacttg tatcgtatgg tgaagtcgat tcgtgcgacg aatggtcagg     780
aggctattgt gttgcatcat ccggattgtg ccacttttga gaagaagtgt ggctgcagcg     840 gttgggggttc ggttgagttt gtggctcgta gccggggttc ggctcgcggg tttacggttg     900
atgatttggt gtgtgatgag gctcaggagt tgtcggatga gcagttggag gctttgcttc     960
ctacggtaag tgctgccccg tctggtgatc cgcagcagat tttccttggt acgccgcctg    1020
ggccgttggc tgatggttct gtggtgttgc gtttgcgtgg caggcgcctt ggtggcgta    1080 aaaggtttgc gtggacggag ttttcgattc ctgacgagtc tgatccggat gatgtgtcgc    1140
ggcagtggcg gaagttggcg ggggatacga atccggcgtt ggggcgtcgc ctgaattttg    1200
ggaccgtaag cgatgagcat gagtcgatgt ctgctgccgg ttttgctcgg gagcggcttg    1260
gctggtggga tcgtggccag tctgctgcgt ctgtggttcc tgctgataag tgggctcagt    1320
ctgcggtgga tgaggcgagt ctggttggcg ggaaagtgtt tggtgtctcg tttttctcgtt    1380 ctggggatcg ggttgctttg gcgggtgccg gcaagactga tgctggggtt catgttgagg    1440
```

```
ttattgatgg gctgtcggga acgattgttg atggtgtggg ccggttggct gactggttgg    1500
cggttcgttg gggtgatact gaccggatca tggttgccgg gtctggtgcg gtgttgttgc    1560
agaaggcgtt gacggatcgt ggtattccgg gccgtggcgt ggtggttgct gatactggcg    1620
tttatgtgga ggcttgtcag gcgtttcttg agggtgtcag gtcgggtgtg atcagtcatc    1680
ctcgtgctga ttctcgccgt gacatgttgg atattgctgt gaggtcggct gtgcagaagc    1740
gtaaggggtc tgcgtggggt tggggttcct cgtttaagga tggttctgag gttcctttgg    1800
aggctgtgtc tttggcgttt ttgggggcta aacgtgttcg tcgtggccgt cgggagcgta    1860
gtggtaggaa gcgggtgtct gtggtatgaa ctcggatgag ttggctctga ttgagggcat    1920
gtacgatcgt atccaaaggt tgtcttcgtg gcattgttgt attgagggct actatgaggg    1980
ctctaatcgg gtgcgtgacc ttggtgtggc tattccgccg gagttgcagc gtgtgcagac    2040
tgtggtgtcg tggcctggta tagctgtgga tgctttggag gagcgtctgg attggcttgg    2100
ctggactaat ggtgacggct acggccttga tggtgtgtat gctgcgaatc ggcttgctac    2160
ggcgtcgtgt gatgtgcatt tggatgcgct gattttttggg ttgtcgtttg ttgcgatcat    2220
tcctcatggt gatggtacgg tgtcggttcg tccgcagtca ccaaagaatt gtacgggcaa    2280
gttttcggct gacgggtctc gtttggatgc gggtttggtg gtgcagcaga cgtgtgatcc    2340
tgaggttgtt gaggctgagc ttttgcttcc tgatgtgatt gttcaggtgg agcggcgggg    2400
ttcgcgtgaa tgggttgagg tggatcgtat accgaatgtg ttgggtgcgg ttccgttggt    2460
gcctattgtg aatcgtcgcc gtacttctag gattgatggc cgttcggaga ttacgaggtc    2520
tattagggct tacacggatg aggctgtgcg cacactgttg gggcagtctg tgaatcgtga    2580
tttttatgcg tatcctcagc gttgggtgac tggcgtgagc gcggatgagt tttcgcagcc    2640
tggctgggtc ctgtcgatgg cttctgtgtg ggctgtggat aaggatgatg acggtgacac    2700
tccgaatgtg gggtcgtttc ctgtcaatag tcctacaccg tattcggatc agatgagact    2760
gttggcgcag ttgactgcgg gtgaggcggc tgttccggaa cgctatttcg ggtttatcac    2820
gtctaaccca cctagtgggg aggctttggc tgccgaggaa tctcggcttg tgaagcgtgc    2880
tgagcggcgt caaacgtcgt ttggtcaggg ttggctgtcg gttggttttt tggctgccaa    2940
ggcgttggat tctcgtgttg atgaggccga tttttttggt gatgttggtt tgcgttggcg    3000
tgatgcttcg acgcctaccc gggcggctac ggctgatgct gtgacgaagc ttgttggtgc    3060
cggtattttg cctgctgatt ctcgtacggt gttggagatg ttggggcttg atgatgtgca    3120
ggttgaggct gtgatgcgtc atcgtgctga gtcgtctgac ccgttggcgg tgcttgctgg    3180
ggctatatcg cgtcaaacta acgaggtatg ataggcgatg gcttcggggg ttgaggcgag    3240
gcttgcggcg actgagtatc agcgtgaggc ggtcaggttt gctgggaagt atgcgggcta    3300
ttattctgag cttggtcgtt tgtggcgtgc cggcaggatg agtgacacgc agtatgtgcg    3360
tttgtgtgtg gagttggagc gtgccggcca tgatggttcg gcatcgttgg ctgccaggtt    3420
tgtgtcggat tttcgccggt tgaatggtgt ggatccgggt ttgattgtgt atgacgagtt    3480
tgatgctgcg gcggctttgg ctaggtctat ttcgaccacg aagattcttg agagtgaccc    3540 ggataggggca aatgacacga ttgatgcgat ggcggcgggt tttgatcggg ctgttatgaa    3600
tgctggccgt gacacggttg agtggtctgc gggtgcgcag ggtaggtcgt ggcgtcgggt    3660
gacggatggt gatccgtgtg cttttttgtgc catgttggct acgaggtcgg attatacgac    3720
aaaagagagg gcacttacta ctggacatac tcggcgtcat aagcgtggtg gtaagcgtcc    3780
gtttggttcg aagtatcatg atcattgtgg ttgtacggtg gttgaggttg ttggcccttg    3840
```

```
ggaaccaaat agggctgatg ccgagtatca gaggacgtat gagaaggcct gtgagtgggt    3900
tgatgatcat gggttgcagc aatcgcctgg caatattttg aaggctatgc gtactgttgg    3960
cgacatgaga taatttgatg tggtttccgg ttgtgcgccg ccggttattg gtgcacaggg    4020
ttgtctcccg cacgggggtc aacaatattg tgttgttttc cgcaaggagt gtagggttag    4080
gctatggccg atcagagtgt tgaggaacag aatgttgaca atgatgttgt ggagtccgga    4140
aaggataacg gcattgttga tacagtaaaa gacgatggcg gcaggaggt agccgacaat      4200
cagttgaaga atgaaggcga gggtaaatcg ccggggactg attggaaggc tgaggcccgt    4260
aagtgggagt ctcgtgctaa aagtaatttt gccgagttgg agaagcttcg cgcctcggat    4320
ggtgatgcgg ggtctacgat tgatgagctt cgccgcaaga atgaggaact cgaagaccgg    4380
atcaatgggt tgttcttga gggtgtgaag cgcgaggtgg ctgccgagtg tggcctgtcg      4440
ggtgatgctg tcgctttctt gtcgggtggc gataaggagt cgcttgccga gtctgcgaaa    4500
gctttgaagg gtttgatcga ccatagtagt ggtggcgcgg gtgtgcgccg tcttgcgggg    4560
agtgcccccg ttgatgatgt taaacgacgt gagggtgtcg cgtttgtgga tgctcttgtc    4620
aataattcta ggagatgatt tgtgatggct gacgattttc tttctgcagg gaagcttgag    4680
cttcctggtt ctatgattgg tgcggttcgt gaccgtgcta tcgattctgg tgttttggcg    4740
aagctttcgc cggagcagcc gactattttc gggcctgtga aggtgccgt gtttagtggt      4800
gttcctcgcg ccaagattgt tggtgagggc gaggttaagc cttccgcgtc tgttgatgtt    4860
tcggcgttta ctgcgcagcc tatcaaggtt gtgactcagc agcgtgtctc ggatgagttt    4920
atgtgggctg atgctgatta ccgtctgggt gtgcttcagg atctgatttc cccggctctt    4980
ggtgcttcga ttggtcgcgc cgtggatctg attgctttcc atggtattga tcctgccact    5040
ggtaaagcgg cttccgctgt gcatacttcg ctgaataaga cgaagaatat tgttgatgcc    5100
acggattctg ctacgctga tcttgttaag gctgtcggcc tgattgctgg tgctggtttg      5160
caggttccta acggggttgc tttggatccg gcgttctcgt ttgcgctgtc tactgaggtg    5220
tatccgaagg ggtctccgct tgccggtcag cctatgtatc ctgccgccgg gtttgccggt    5280
ttggataatt ggcgcgggct gaatgttggt gcttcttcga ctgtttctgg cgccccggag    5340
atgtcgcctg cctctggcgt taaggctatt gttggtgatt tctctcgtgt tcattggggt    5400
ttccagcgta acttcccgat cgagcttatc gagtatggtg acccggatca gactgggcgt    5460
gacttgaagg gccataatga ggttatggtt cgtgccgagg ctgtcctgta tgttgcgatt    5520
gagtcgcttg attcgtttgc tgttgtgaag agaaggctg ccccgaagcc taatccgccg      5580
gccgagaact gattcatttg ttgcggtgat gttttctatg tgcagggggt ggtgttgatg    5640
ggtatcattt tgaagcctga ggatattgag cctttcgccg atattcctag agagaagctt    5700
gaggcgatga ttgccgatgt ggaggctgtg gctgtcagtg tcgcccccctg tatcgctaaa    5760
ccggatttca aatacaagga tgccgctaag gctattctgc gcaggccct gttgcgctgg      5820
aatgataccg gggtttcggg tcaggtgcag tacgagtctg cgggcccgtt tgctcagact    5880
acacggtcga atactcccac gaatttgttg tggccttctg agattgccgc gttgaagaag    5940
ttgtgtgagg gtgatggtgg ggctggtaaa gcgttcacta ttacaccgac catgaggagt    6000
agtgtgaatc attctgaggt gtgttccacg gtgtggggtg agggttgctc gtgcggatct    6060
gatattaacg gctatgctgg ccctttgtgg gagatatgat atgaccggtt ttccttacgg    6120
tgaaacggtt gtgatgcttc aaccgactgt tcgtgtcgat gatcttggcg acaaggtgga    6180
```

```
agactggtct aagcctgtcg agactgtgta ccataacgtg gccatctatg cttccgtttc    6240
gcaggaggat gaggctgccg gccgtgactc tgactatgag cattggtcga tgcttttcaa    6300
gcagcctgtt gtgggtgccg gttatcgttg ccggtggcgt attcggggtg tggtttggga    6360
ggcggacggg tctcctatcg tgtggcatca tccgatgtct ggttgggatg ctggtacgca    6420
ggttaatgtg aagcgtaaga agggctgatg ggttgtggct caggatgtga atgtgaagct    6480
gaacttgccg ggtattcgtg aggtgttgaa gtcttctggg gtgcagtcga tgttggctga    6540
gcgtggcgag cgggtgaggc gtgcggcttc ggcgaatgtt ggcggtaatg cttttgatag    6600
ggcccaatac cgtagtggtt tgtcgtcgga ggtgcaggtt caccgtgtgg aggctgtggc    6660
gaggattggc accacctata agggtgggaa gcgtattgag gcgaagcatg gcacgttggc    6720
gaggtcgatt ggggctgcgt cgtgatcgtt tacggtgatc cgcgtgtgtg ggctaaacgt    6780
gtgctcaagg atgatggctg gctgtccgat atacgctgtg tggggacggt gcctgacgat    6840
ttcagcggtg acctgatttg gttggcgttg gatggcggcc cacagttgca tgttcgcgag    6900
caggtgtttt tgcgggtgaa cgtgtttttct gatatgcctg atcgtgccat gtcgctagcc    6960
aggcgggttg aggctgtcct tgtagacggt gtggacggtg acccggtggt gttttgtcga    7020
cggtctactg gccctgattt gctggttgat ggtgcacgtt ttgatgtgta ttcgctgttt    7080
gagctgatat gcaggcctgt cgaatccgag taaacgttt gttttgatat tgttgtttgt    7140 ttttgtttg atattgtttt tggggttat gatggctgga acacgtaaag cgtctaatgt    7200
tcgttccgcg gttacgggtg acgtctatat tggtaaagct catgccggtg acactattga    7260
tggtgtgaag acggttcctg acgggcttac agctttaggg tatctgtctg atgacgggtt    7320
taagattaaa ccggagcgta aaacggatga tttgaaggct tggcagaatg cggatgttgt    7380
tcgcactgtg gctacggaat cgtctatcga gatttctttc cagctgatcg agtctaagaa    7440
ggaggttatc gagctgtttt ggcagtcgaa ggttactgcc ggagccgatt cgggttcgtt    7500
cgatatttct cctggtgcca cgacgggtgt tcatgccctg ttgatggata ttgttgatgg    7560
cgatcaggtt attcgctact atttccctga ggttgagttg atcgatcgtg acgagattaa    7620
gggtaagaat ggcgaggtgt atgggtatgg tgtgacgttg aaggcgtatc ctgcccagat    7680
taataagaag ggtgatgcgg tgtctggtcg ggggtggatg acggctttaa aagctgatac    7740
tcctccgact cctcctccgg ccccgaatcc tccgaagcct gagccggatc cgaatccgcc    7800
gtctaataac tgatacacat agtttgaggg attgttgata gatgagtgac acgggttaca    7860
cgttgaagat tggtgaccgt agctgggtgt tggcggatgc ggaggagacg gctcaggctg    7920
ttcctgcccg cgttttccgt cgtgctgcta agattgccca gtcgggtgag tctgcggatt    7980
tcgcccaggt tgaggtgatg ttttctatgt tggaggctgc cgccccggct gacgcggtgg    8040
aggccctgga ggggcttcct atggttcgtg tggccgagat ttttccgccag tggatggaat    8100 acaagcctga cggtaagggt gcctcgctgg gggaatagtt tggctccacg gcctgattga    8160
tgattatcgt ggggccatcg aatacgattt ccgcaccaag tttggtgttt ctgtttatag    8220
tgttggtggc ccgcagatgt gttggggtga ggctgtccgg ctggctggcg tgttgtgtac    8280
cgatacgtct agccagttgg cggcccacct gaatggttgg aagcgcccgt ttgagtggtg    8340
cgagtgggct gtgttggaca tgctggatca ttacaggtct gctaatagtg aggggcagcc    8400
ggagcctgtg gcgaggccta cggatgagcg tagggcccgg tttacgtctg gcaggtggat    8460
cgatattttg gcgcgtgttc gtgctggtgg cggggtgtct cgcgagatta atattatggg    8520
gtgaatagtg tatgtctggt gagattgctt ccgcatatgt gtcgttgtat acgaagatgc    8580
```

```
ctggtttgaa ggcggatgtt ggtaaacagc tttctggggt gatgcctgct gagggtcagc   8640
gttcgggtag tttgtttgct aagggaatga agttggctct tggtggtgcg gcgatgatgg   8700
gtgccatcaa tgttgctaag aagggcctca agtcgattta tgatgtgact attggtggcg   8760
gtattgctag ggcgatggct attgatgagg ctcaggctaa gttgactggt ttgggtcata   8820
cgtcttctga cacgtcttcg attatgaatt cggctattga ggctgttact ggtacgtcgt   8880
atgcgttggg ggatgcggcg tctacggctg cggcgttgtc tgcttcgggt gtgaagtctg   8940
gcgggcagat gacggatgtg ttgaagactg tcgccgatgt gtcttatatt cgggtaagt    9000 cgtttcagga tacgggcgct attttttacgt ctgtgatggc tcgcggtaag ttgcagggcg   9060
atgacatgtt gcagcttact atggcgggtg ttcctgtcct gtctttgctt gccaggcaga    9120
ctggtaaaac gtctgctgag gtgtcgcaga tggtgtcaaa ggggcagatt gattttaaca    9180
cgtttgcggc tgcgatgaag cttggcatgg gtggtgctgc gcaggcgtct ggtaagacgt    9240
ttgagggcgc tatgaagaat gttaagggcg ccctgggtta tcttggtgct acggctatgg    9300
ccccgtttct taacgggttg cggcagattt tgttgcgtt gaatccggtt atcaagtctg     9360
tcacggattc cgtgaagccg atgtttgctg ccgtcgatgc tggtattcag cgtatgatgc    9420
cgtctatttt ggcgtggatt aaccgtatgc cggctatgat cactcgaatg aatgcacaga    9480
tgcgcgccaa ggtggagcag ttgaagggcg ttttttgcaag gttgcatttg cctgttccta   9540
aggtgaattt gggtgccatg tttgctggcg gcaccgcagt gttcggtatt gttgctgcgg    9600
gtgttgggaa gcttgtcgcg gggttttgccc cgttggcggt gtcgttgaag aatctgttgc    9660
cgtcgtttgg tgctttgagg ggtgccgccg gggggcttgg tggcgtgttt cgcgccttgg    9720
gtggccctgt tggtattgtg atcggcttgt ttgctgccat gtttgctacg aacgcccagt    9780
tccgtgccgc tgttatgcag cttgtggggg tggttggccg ggctttgggg cagattatgg    9840
tcgccttgca gccattgttc gggattgttg ctggcgtggt tgccaggttg gctcccgttt    9900
ttggccagat tattggtatg gttgctggtt tggctgcccg gctggtgcct gttattggta    9960
tgcttattgc ccggctggtt cctgttatca cccagattat tggtatggta acccaggttg    10020
ctgccatgtt gttgcctatg ctgatgccgg ttattcaggc tgttgttgct gtgatacggc    10080
aggttattgg tgtggtcatg cagttgatac ctgttttgat gccggttgtg cagcagatt     10140 tgggtgctgt catgtctgtt ttgccgccga ttgttggttt gatacggtcg ctgataccgg    10200
tgatcatgtc gattatgcgt gtggtggtgc aggttgttgg tgccgtgcta caggtggtgg    10260
cccgtattat tccggttgtt atgccgattt atgtttcggt gattggattc attgccaaga    10320
tttatgctgc ggttatcgtt tttgaggcta aggttattgg cgctattctt cgtactatta    10380 cgtgattgt gaatcattca gtgtctggcg tgaggtctat gggcacggcc atccagaatg    10440
gctggaatca tatcaaatcg tttacgtcgg cgtttattaa cggtttcaag tcgatcattt    10500
ctgccggtgt tgccgcggtt gtggggtttt ttacgcggct tggtttgtcg gttgcctccc    10560
atgtgaggtc tggttttaac gcggcccgtg gtgctgtttc ttctgcgatg aatgctattc    10620
ggagtgttgt gtcttcggtg gcgtctgctg ttggcgggtt tttcgggtcg atggcgtcta    10680
gggttcgtag tggtgctgtg cgcggggttta atggtgcccg gagtgcggct tcttctgcta    10740
tgcatgctat ggggtctgcg gtgtctaacg gtgtgcatgg tgtgctgggg ttttttccgga    10800 atttgcctgg caatattagg ggcgccttgg gtagtatggg gtccctgttg gtgtcggctg    10860
gccgtgatgt ggtgtctggt ttgggtaacg gtatccggaa tgctttgagt ggcctgttgg    10920
```

```
atacggtgcg taacatgggt tcccagattg cgaacgcggc gaagtctgcg ctgggtattc   10980
attccccgtc tcgggtgttt cgtgacgagg ttggccgtca ggttgttgcc ggtttggctg   11040
aggggatcac cgggaatgct ggtttggcgt tggatgcgat gtctggtgtg gctggccgtc   11100
ttccggatgc tgtggatgcc cggtttggtg tgcgatcgtc tgtgggctcg tttaccccgt   11160
acgaccggta tcggcgtgcg aacgagaaga gtgttgtggt gaatgtgaac ggacccacgt   11220
atggggatcc tgccgagttt gcgaagcgga ttgagcgtca gcagcgtgac gctttgaatg   11280
cgttggctta cgtgtgatcg aggggtgtt gtgcatgttt attcctgacc cgtctgatcg   11340
tgccggtttg actgtggatt ggactatgtt tccgttggtg ggtaatgctc cggagcgtgt   11400
gcttcatttg acggattata cggggtcgtc tccggtcatg ttgttgaatg attcgttgcg   11460
cggcctgggt atgcctgagg tggagcagtt ttctcaaacg catgttggtg tgcatggttc   11520
ggagtggcgc gggtttaatg tgaagcctcg cgaggtgact ttgccggtgt tggtgtcggg   11580
tgttgacccg gatccggtgg gcgggtttcg tgacggtttt ttgaaggcgt atgacgcgtt   11640
gtggtctgcg tttcctccgg gcgaggtggg ggagttgtct gtgaagactc ctgccggtcg   11700
tgagcgtgtg ttgaagtgcc ggtttgattc ggctgatgac acgtttacgg ttgatccggt   11760
gaaccgtggc tatgcgcgct atctgttgca tttgacagct tatgatccgt tttggtatgg   11820
ggatgagcaa aagtttcgtt ttagtaacgc gaagttgcag gattggttgg gtggcggccc   11880
tgtcggcaag aagggtaccg cgtttcctgt ggtgttaaca ccgggtgtgg gctcgggctg   11940
ggataacctg tctaataagg gtgatgtgcc tgcgtggcct gtgattcgtg ttgagggtcc   12000
tttggagtcg tggtctgtgc agattgatgg tttgcgtgtg tcttcggact atccggtcga   12060
ggagtttgat tggatcacta ttgatacgga tcctcgccag cagtctgcgt tgttgaacgg   12120
gtttgaggat gtgatggatc gtttgacaga gtgggagttt gcgcctatcc cgcctggcgg   12180
ttctaagagt gtgaatattg agatggttgg tttgggtgct attgttgtgt cggtgcagta   12240
caggtttttg agggcttggt gaatagttga tggctggtct tgttccgcat gtaacattgt   12300
ttacacctga ttatcgccgt gtggcgccta tcaattttt tgagtcgttg aagttgtcgt   12360
tgaagtggaa tggtttgtcg actttggagt tggtggtgtc gggggatcat tcgaggcttg   12420
acgggttgac gaagccgggt gcgcggctgg ttgttgatta tggtggtggc cagattttt   12480
ctgggcctgt gcgtaaagtg catggtgtgg gtccgtggcg ttcttcccgt gtgactataa   12540
cgtgtgagga tgatattcgg ctgttgtggc gtatgttgat gtggcctgtg aattatcgtc   12600
ctggtttggt tggtatggag tggcgtgcgg acagggatta tgcccactat tcgggtgcgg   12660
ctgagtcggt tgctaagcag gtgttggggg ataatgcttg gcgttttccg cctggtttgt   12720
ttatgaacga tgatgagagt cgtggccgct atattaagga ttttcaggtg cggtttcacg   12780
tgtttgccga taagttgttg ccggtgttgt cgtgggctcg gatgactgtc acggtgaacc   12840
agtttgagaa tgcgaagttt gatcagcgtg gtttgttgtt tgattgtgtg cctgctgtga   12900
cccggacgca tgtgttgact gccgagtctg gttcgattgt gtcgtgggag tatgtgcgtg   12960
acgccccgaa ggctacttcg gtggtggttg gtggccgcgg cgagggcaaa gatcggctgt   13020
tttgcgagga tgttgattcg atggccgagg atgactggtt tgatcgtgtc gaggtgttta   13080
aggatgcccg taacacggat tccgagaatg tgcatcttat tgatgaggct gagcgggtgt   13140
tgtccgagtc gggggctacg tcgggttta agatcgagtt ggctgagtcg gatgtgttgc   13200
ggtttgggcc tggccgcctg atgccgggtg atcttatcta tgtggatgtg gctcggggc   13260
ctattgcgga gattgtgcgc cagattgatg tggagtgtga ttcgcctggt gatgggtgga   13320
```

```
cgaaggtgac tccggttgct ggggattatg aggataatcc gtcggcgctg ttggctcgcc    13380
gtgtggctgg tttggctgcg ggtgtgcggg atttgcaaaa attctaattg ttaggggttt    13440
gttgtgggta ttgtgtgtaa agggtttgat ggtgtgttga ccgagtatga ttgggctcaa    13500
atgtctggtc tgatgggtaa tatgccgtcc gtgaaagggc cggatgattt tcgtgtcggc    13560
actacgattc agggttccac ggtgttgtgt gaggtcctgc cggggcaggc ttgggctcac    13620
ggggtgatgt gcacgtcgaa tgctgttgag acggtgacag gtcagcttcc gggcccgggt    13680
gagacccgct acgactatgt tgtcctgtcg cgggattggc aggagaatac ggccaagttg    13740
gagattgttc ctgggggcg tgcggagcgt gcccgtgacg tgttgcgtgc ggagcctggc    13800
gtgtaccatc agcagttgtt ggctactttg gtggtgtcgt ctaacgggtt gcagcagcag    13860
cttgacagga gggctatagc ggccgtgtg gcgtttgggg agtctactgc atgtgatcct    13920 accctgtgg agggtgaccg ggtgatggtg ccttctgggg ctgtgttggc taatcatgct    13980
aacgagtgga tgctgttgtc tccgcggatt gagacgggca ctaagtcgat catgtttggc    14040
gggtctgctg tgtatgctta cacgattccg tttgatcgcc agtttgctag tccgcctgtt    14100
gtggtggcgt ctatggctac ggcggctggg ggcacgaccc agattgatgt gaaagcctac    14160
aatgtgactg cccaaaattt tagtttggcg tttattacga atgatggttc gaagccgaat    14220
ggtgtgcctg cggtggctaa ttggattgct gtcggcgtgt gactgtacag gtgttgtggc    14280
ggatggtgtg atgttggggg gctgtggtgt cgtggtttac tcctgcactg gtggcctcta    14340
tttgtaccgc gttggccacg gttttgggtt ctgttcaggc tgtcacgtct aaatctagga    14400
ggcgtttgcg ccgcctgtcg gcgcaggtgg atgcgatgga agagtatacg tggggtgtgc    14460
ggcgcgaggt gcgaaggttt aacgccgggc ttcctgacga ggtggagcct atgcatctcc    14520
ctgatttgcc cgagttttg aaagatactg ttgatggtgg aggtgagtag ggttgaggga    14580
gttggaggag gagaagcggc agcgccgcaa ttttgagaag gcttcactgg tgttgctgtt    14640
tttgtcgctt gtgttattgg ctgtggttgc tgcgggtgct ttgcgtttcg gggctgtatc    14700
ctctgagcgg gattcggagc aggcgagggc ccagtcgaat ggtacagccg ccaagggttt    14760
agccagcagt gtgcggcagg tgtgtgctca gggtggacgg gagtctgtgc ggcttcacca    14820
gtctggtttg tgtgtggatg ctcagcgtgt tgagcgtagt gtgcagggtg tgccgggtcc    14880
tgccggtgag cgcggcccgc aaggcccggc aggtgtggac ggccgggatg gtgttaatgg    14940
ttcggctggg ctggttggcc ctgtgggtcc gcaggggtcc ccgggtttga atggtgtgaa    15000
aggtcctgac gggttgcctg cgctaacgg ttcggatggc cgtgatggtg tggacggtgt    15060
gaacggcaat gatggcgctg atggtcggga tggttcggcc ggtgagcgcg gtgatgtggg    15120 ccctcaggt cctgccggcc cgcaaggtgc acagggtgaa cggggtgagc gcggccccgc    15180
cggtgcgaat ggcacgaatg gcaaggacgg taaggatggt gccgacggcc gtgatgggcg    15240
ttcggttgtg tctgtgtact gtttcggtgg cctgccaggg tgtgaaacca tcacctgtgg    15300
ttaccgtgtc atcccgtaaa tagaagaaga gggaagggtg ttactagtgt tgattgtggt    15360
ttttggtggt ggtgtgtggt gagatacatt cctgcagcgc atcactctgc cggctctaat    15420
aatccggtga acagggttgt gattcatgca acatgcccgg atgtggggtt ccgtccgcc    15480 tcacgtaagg ggcgggcggt gtctacagca aactatttcg cttccccatc gtctggtggt    15540
tcggcgcatt atgtgtgtga tattggggag acggtgcaat gcttgtcgga gtctacgatt    15600
ggttggcatg ccccgccgaa tccgcattct ttgggtatcg agatttgcgc ggatgggggt    15660
```

```
tcgcatgcct cgttccgtgt gccggggcat gcttacactc gggagcagtg gcttgatccg    15720
caggtgtggc ctgccgttga gagggcggcg gtgctgtgta gacgtttgtg tgacaaatat    15780
aatgttccga aaaggaaact gtcggctgcc gatttgaagg ctggcaggcg gggtgtgtgt    15840
ggccatgtgg atgttacgga tgcgtggcat cagtcggatc atgacgatcc tgggccgtgg    15900
tttccgtggg acaaatttat ggccgtcgtc aacggcggca gtggagatag tggggagtta    15960
actgtggctg atgtgaaagc cttgcatgat cagattaaac aattgtctgc tcagcttact    16020
ggttcggtga ataagctgca ccatgatgtt ggtgtggttc aggttcagaa tggtgatttg    16080
ggtaaacgtg ttgatgcctt gtcgtgggtg aagaatcctg tgacggggaa gctgtggcgc    16140
actaaggatg ccctgtggag tgtctggtat tacgtgttgg agtgtcgtag ccgtcttgac    16200
aggctcgagt ctgctgtcaa cgatttgaaa aagtgatggt ggtttgttgt gggtaaacag    16260
ttttggttag gtttgctaga gcgggcggct aagacttttg tgcaaacgtt tgttgctgtg    16320
ttgggggtga cggcgggtgt cacgtatacg gcggagtcgt ttcgtggttt gccgtgggag    16380
tctgcgttga ttacggctac ggttgctgcg gtcctgtcgg tggctacctc gtttggtagc    16440
ccgtcgtttg tggctggtaa gccgaaaacc acgcctgtgg atgcgggttt ggttccgccg    16500
gatgatcccg gaatagtgga gcctcacatg gtggatgtgt cggatcctgg catgatcgag    16560
cctgcagatg atgtggatct tggtgtaggc tatgtgccga acatgctgc cgagtcggag    16620 gttggcacgg tagagtcgac tgttgcataa gtgaatatag atgtgtgccc cagcggtgct    16680
gccacgattg tgtggtggtt gccgctgggg cactattttt gtatattgcg gtgtggctat    16740
gattcgttgc tgtcgatggt gtcttcgagc atctggtaca ggtggaggca ggtagagata    16800
gtttcgctgg cctggtcgag aacgttccgg ccgataacat ttttgttgtt gtcgcggtgg    16860
cggatgatag accacatgat ctcgtcggct gccgcctgca atagttttgc ctggtatgcg    16920
attccagcga gccagtctag tgcttcctgg cttgcatagg gtgtctggtc ctcgctgttg    16980
cttgtggggt gtcctgcact gtcgcatagc cacaggattt cgctgcactc gtctagcgtg    17040
tcctggtcta tagcgagatc gtcgaggctg acattgttga cggtaaggtt cacgttgtcg    17100
agggagatgg gtacaccgta ctggttttcg acaccgtcaa caatgttttc caattgctgc    17160
atgttggtgg gctgttgttg gacgatacgg tgtatcgctg tgttgagggt ggtgtaggtg    17220
atattgtgtg tgttgttcat cgtgttatgc cattccttcg ttatcgtctg gcctgtagta    17280
tgtgctgttt gcgtactcgg ttaacgtcat cagtgtttgg tctgcccact gtttcacagt    17340
ctgccttgtc actccgagtc gttgggcggc tgtggcgtag gtttggtcat acccgtatac    17400
ttccctgaat gctgccaacc gtgccaaatg ttttcgctgt ttggatggct ggcaggcgag    17460
ggtgtagtcg tcgatggcta gctgtagatc gatcatggtg gcaatgttgt tgccgtggtg    17520
ttgtggcgcg gttggtgggg gtggcattcc tggctccaca ctgggtttcc atgggcctcc    17580
gttccagatc cattgggcgg cttggatgat gtctgcggtg gtgtaggttc ggttcactgg    17640
tcatcccctg aacaggttgt ctgggttgct ggtgcggatt gtgtcgaatc gtccgacgca    17700
gtggcagtag tcgtacatga gtttgataat gtgttggtgg tctcccaaat aggtgtttcc    17760
gctgatgctg taggtggctg tgccgtcttt actaatagtg tatttggcgg tgatggtttc    17820
ggggttttcg gtgtcggtga tgatggctgt ggtggtggtg cctacggttt ggagcacggt    17880
ggtttgggtt ccgtcgtcga tggtggtttt aaccatgagg tgtgttctcc ctttgtgtta    17940
gttgctggtt tggttgtcgg ctagatgaat gatgtcgggt aagggtttcg gctggtctaa    18000
atgttgtgtg gttttgttgg ctagccgttt ggctaccctg tagcacattt tggtgtagtg    18060
```

```
tttgttgtct aggttgtggt attgttcccg caccgcaata tatagcaggg agtcttggta    18120
caggtcgtct gcattgattg cggggtagtg tgcggctgtt ttagtgcatg cccggttgag    18180
tgtgcgtaga tgatggtctg tggcccacac ccacgatgcg gtggtggcta ggtcggcttt    18240
tgttggtcgt cggctcatgg catctctttc atctggctat ctggtagttg tttggtgttt    18300
tgttgttgat agtgtagcac acgagtccgg ggtttccggt ggtgcccgtc ttgtgccggt    18360
accatgtgga ttcgccttcc atggatgggc attggatgaa ggtgcgttgt ccttgttcgg    18420
agatttctag gtggtgcctg tgtccggcca tgaggatgtg ggatgtggtg ccgttgtgga    18480
attcttgtcc gcgccaccaa tcatagtgtt tgccggtgcg ccattggtgg ccgtgggcgt    18540
gtagtatccg tgtgccggct acttcgacgg tggtggtcat ttcgtctcgg ctggggaaat    18600
aaaagtgtag gttggggtat tggttggtga gctggtaggc ttctgcgatg gcgcggcagc    18660
agtctacgtc gaaggagtcg tcgtaggtgg tgactccttt gccgaagcgt acggcttctc    18720
cgtggttgcc ggggatggat gtgatggtca cgttttttgca gtggtcgaac atgtggatga    18780
gttgcatcat ggccatgcgg gtgagcctga tttgttccgt caagggggtt tgtgtgcgcc    18840
aggcgttgtt gcctccttgt gacacgtatc cttcgatcat gtcgccgagg aatgcgatgt    18900
ggactcgttc gggtttgcct gcctgctgcc agtagtgttt agctgatgtg agggagcgca    18960
ggtagtcgtc ggcgaagtgt gatgtttccc cgccggggat gcctttgccg atttggaagt    19020
cgcctgcccc gatgacgaag gccgcagtgc tgtagtcggt gcgggtgtcc tgttcgggtt    19080
ttgggggtgt ccattcggct agtttatcga cgagttcgtc tacagggtag gggtttgttg    19140
cgggttggtg gtcgatgatt ttttgtacgg atctgcctgt ttctccgttg gggagtgtcc    19200
attcggagat gcgtgtgcgg cgtacggtgc cgtttgcgag atcatcgcag atggtgtctg    19260
cttcgctatc gtggttggct agctgggtga gtagccggtc tatgttgtct atcactgggt    19320
atcctcttct tgcggggtgg tgttggcttg tttgcggcgg tagtctttta taacggtggc    19380
ggagatgggg tatcctgcct gggtgagctg ttttgctagc catgaggcgg ggatggtttt    19440
gtcggcgagc acgtcggcag ccttgttgcc gtagcgttgg atgagtgttt cagttttggt    19500
tgccatggtg tcctatcggt tgtgtggtgg gctgccatcc tgtgcggcag tcgccgtcgt    19560
ggcctggttt gcgtgtgcac cacgatacgg ttctgtctgt gtggttgagt gttttgccgc    19620
acatgacgtt ttgtagatgc tctggcagtg cgccgtcacc ctggttgctg gtttgtgtgt    19680
cgaagagtgt tttctggttg gtgaaatgct cggacacggt gccattatgt acgggtagta    19740
tccatgtttt ccattgttgt tgtagccggg tgttccagtg gaattgtttt gctgcgttcg    19800
tggcttgttt gatggtttg tagtagccga cgaggatgcg ctggtgttca ctgtcgggag    19860
ggttttggcc tcgccagtat tgtgccgcca cggcgtagcg gttgctggct gtgaaggcgt    19920
cccagcagta ttcaataatg tgttgtagta cactatcggg catgtctcgt acttggtttt    19980
cgtcgagcca cgcgtcgaca atgatgttgc gtatggcgcg tttgtctttg gtggtgggtt    20040
tgaatgcgat gctcacagta cgggcctgtc gtcttgcatg aaatcattaa aggatgattc    20100
gcttgcgcgg cgtgcttgtg tgatttgctg gtcagaccag tcggggtgtt gctgtttcag    20160
atagtaccag tggcacgcat tgtaggtttc gtcttgtagc cgggtgagat ggttttcggt    20220
gatgatttgt ttccacatag tccatgacac gtcgagccgg tccaatattt ccattgctgg    20280
aatgttgaac tggttcagga agagtatttc gtgggtgtag tattccttct cgtactggtc    20340
ccatccactt cggtgcctgt tgggctggtt tttggggtag gcttcccggc atactttgtg    20400
```

-continued

| | | | | |
|---|---|---|---|---|
| caaatgtttg | gccatgtcgt | cgggtagttt | aatgtcaggg | ttggcgcgga tcatggatcg | 20460 |
| catcccatca | taggtggtgc | cccaggtgtg | catgatgtag | gtggggtctt caccatcagc | 20520 |
| ccatttttct | gcacagatgg | cgaggcggat | gcgtctcctg | gctgattggc tggtgttgcg | 20580 |
| ccggttgggg | atgggcacg | tgtcgagggg | atccatgatg | ttttggtgta cctttcttgg | 20640 |
| tttaggttgc | ttgtgtggtt | ttattgtagc | actgtgtcta | gtgcttgtgt caaccctgtt | 20700 |
| ttgccggcct | gaaggtaggt | gtctgtgaca | tcccccaggg | tgaggggcac atgggtggct | 20760 |
| tgggggagtg | cggcctggag | tgtttgggcc | atctggtggc | ccgccttgtc tgggtctgac | 20820 |
| cagatgtaga | tgtggtcgta | gccttcaaaa | aatttggtcc | aaaaagtttg ccacgaggtt | 20880 |
| gcgccgggta | gggctacggc | tggccatccg | cattgttcga | ggatcatgga gtcgaattcg | 20940 |
| ccttcgcaaa | tgtgcatttc | ggctgccggg | ttggccatgg | cggccatgtt gtagatggag | 21000 |
| cctgtgtctc | ctgccggggt | tagatatttg | gggtggttgt | gggttttgca atcatgttgg | 21060 |
| agtgagcagc | ggaaacgcat | ttttcgtatt | tcggctggcc | cttcccagac ggggtacatg | 21120 |
| tatgggatgg | tgatgcactg | gttgtagttt | tcgtggcctt | ggatgggtc attgtcgatg | 21180 |
| tatccaaggt | ggtggtagcg | ggctgtttct | tcgctgatgc | ctcttgccga gagcaggtcg | 21240 |
| agtatgtttt | cgaggtgggt | ttcgtagcgg | gctgaggctt | tctggattcg gcggcgttcc | 21300 |
| gcaatgttgt | aggggcgtat | gctgtcgtac | attcgggttt | tcttcctcta atcgttgttt | 21360 |
| cagtttgtgg | agtccgcctc | cgataccgca | tgtgtgcag | taccagacgc ccttgtcgag | 21420 |
| gttgatgctc | atggagggct | ggtggtcgtc | gtggaacggg | cagaggatgt gttgctcgtt | 21480 |
| ccgtgacggg | ttgtagcgta | tctggtgggc | gtctaggagg | cggcaggtgt cagaggtgtg | 21540 |
| ggaggagctc | gttgagggtt | gataccacat | aggcttcgct | ccagggtttg ttgcgctgtt | 21600 |
| tcatgatgac | gagtccgatg | gtggattggt | tttcgcggtt | tcggtgtgtt tcgtagttgc | 21660 |
| gtgcctcccg | gctggcttgt | ttcacgaatt | cggctaggtg | tgcctgtcct gctttggctt | 21720 |
| cgatcacata | ggttttgttg | ccggttgtga | ggatgaggtc | gccttcgtct tctttaccgt | 21780 |
| tgaggtggag | gcgttctata | tcatagccgg | tgtcgcgtag | ctggtggagg agtcttgttt | 21840 |
| cccattcggc | gccggctcgg | cggttgcgtg | cctgttgtgt | tgacatgata gtcctttatg | 21900 |
| ttcttgtgtc | atgttccagg | gctgtttttc | tactaggggc | ccgaagaatg tgtattcggg | 21960 |
| gtaggctcgt | agtcgttcgt | attttgttcc | gtctgggctg | gatttgccgg ttctctgttt | 22020 |
| caggacggcg | atgcgtgcct | cggcggggat | ggtgaggccg | ttgccgttgt cttcgccacc | 22080 |
| atacagggag | actcccaata | tgagttgtgg | ttttcggag | aggccgtttt tgatttcccg | 22140 |
| cctagctggg | gggtgttcga | tgtcggtgcc | ggttttgtcg | gttgcgtggt gggtgacgat | 22200 |
| gatggtggag | ccagtatctc | tacctaaggc | tgtgatccat | tgcatggctt cttgctgtgc | 22260 |
| ctgatagtcg | gattcgcagt | cttggatgtc | catcaggttg | tctataacaa taatgggtgg | 22320 |
| gaaggtgttc | cacatttcca | tgtaggcttg | cagttccatg | gtgatgtctg tccatgtgat | 22380 |
| gggtgactgg | aatgagaagg | tgatgtgtcc | gccgtggtgg | atgctgtctc gatagtattc | 22440 |
| tggcccgtag | ttgtcgatgt | tgtgttgtat | ctgttgggtg | gtgtgttggg tgttgagtga | 22500 |
| gatgattcgt | gtggaggcct | cccagggtgt | catgtcccct | gatatgtaga gggctggctg | 22560 |
| gttgagcatc | gcggtgatga | acatggctag | ccctgatttt | tggctgccgg accgccccgc | 22620 |
| gatcatgacc | aaatccccctt | tgtggatgtg | catgtccagg | ttgtcataca agggtgctag | 22680 |
| ttgggggtatg | cggggcagtt | cggcggctgt | ttggaggcc | ctctcgaagg atctttggag | 22740 |
| agagagcatc | gggaccttaa | tctatctgtt | ggttgggtgt | gttttggtgg tcagatggag | 22800 |

```
tcgatgtcga tgtcagcatc ggcggggggct gtggtgtcgt ctagctggcc gttgtcgcgt   22860
ttgtctacat attcggcaac cttatcgtag atggcgtcgt cgaggggttt gaggacgacc   22920
gcgttgaacc cgttttggt gcgcacggtg gcaagtttga aggcttgttc ttcgccgaga   22980
tatgcttcta ggtcgcggat catggagtgt gggcggtcgt tgttgccgcg tgcttttcg   23040
atgatggcgt tggggatggt ttctgggtg ccgttgttga gatcctggag ggtgtggaag   23100
attgtgacat cagcgtagat gcggtctgcg acctgtccac cgtagccttc ggtgttgtgt   23160
tctacgtcgc ggattttgaa ggcgatggcg gtggcgtcct ggtttcggga ggggttgaag   23220
aaggtgctgt tgctgttgtt gtggtagttg gcgagtgcca tgattgtgtt atcctttact   23280
gttgtgtctg tttttgttgt cttatattgg tttatcgggt gaggctgttt cgtttgctgc   23340
ggaaagcctc ggaaacgtca ctgttactgg tgatggtctt cttgtactgt ttgagtaggg   23400
ctgctagctg tgtcttgctg gtggctttgt ttatccggtc gatgatgatg tcgttttcct   23460
gtgatgcgat tttgttgacg tagtctttgg cggctttatc gtatcggtct tgaagcagga   23520
ttgctgcgct agcgatgagg gttgcgagat cccagtcttt ggatacggtt tcgtctttca   23580
atcctcctag cagatcaata atggattgtt tgatgtcttc tgcggtgtct ccgcggatga   23640
ctgtccatgg ggcggcatag tcgccaccgt atttgagtgt gatagttagt tttccgctgt   23700
ctgtggtgtg ctcgtcggtc acgtgttttc cttttcgttg ttttcggctt ctggtggctg   23760
tacggtggtt tctatcgggt atctgtaggc gtctttcccg ttgacggccc agcaggcgtc   23820
cttgacgggg catcctttgc agagtgtggt gacgtgggt acgaagatgc cttggctgat   23880
tcctttcatt gcttgactgt acatggatga tacatgccgg taggtgttgt tgtcaagatc   23940
aatgagttcg gttgctgtgc cctgctcgac tgattgctcg tctcccttgg tggtggcggg   24000
tgtccaaaac atgcctttcg tcacatggat gccgtgttgg gcgagcatgt accggtatgt   24060
gtgcagctgc atactgtctg cgggtaggcg tccggttttg aggtccaaaa tgaaggtttc   24120
gccggtgtcg gtgtcggtga atacccggtc aatatatccg actattttg tgtcatcgtc   24180
gagggtggtt tctaccgggt attcgatgcc tggctggccg tcaataacag cggtggcgta   24240
ttctgggtgg ttgcgcctcc atgttttcca gcggtccaca aagtgggggc cgtacatcat   24300
ccaccaattg tagtctttct tgtgtggccc gcctgactcg cacatgtttt tgcatattct   24360
gccggagggc tttatgtttg tgccttcgga ttcggcgagg gcgatttggg tgtcgaaaat   24420
gtttgtgaag gatgagagtt tgtctggcag tgcagggtat tcggcggggt tgtacaggtg   24480
taggtcgtat tgttcggtga tgtggtgtat ggcgcttccg gcgatggtgg cgtaccaggt   24540
gtggtgttgg gcgtggtagc cgtgtgctag gcgccatttt tcgccgcatt cggcccactg   24600
tgtgagtgaa ctgtaggaga tgtggcctgg atggttgatg gttttcgggt attgtgctag   24660
gggcattact tgtcgccttt gtgggtgttc catgggttgc gggtgtcttt gccggcgtgg   24720
tgttgctggt aggcgaggag tgcgaggcag tgccaggcag cgtgtgccag atgcggcaaa   24780
tgtgattcgt tgtcgaggtt gttgccttgc tgccatgata acaggtgccg gtagagggcg   24840
tcgacactgt ggctccacgg gtatcctccg gtccagttgt tgtcgccgta cttggtggca   24900
ccgtagcctc ccacggagcc tagggcgtgc aaggctgcgg ggtcgatgag ggagagcctg   24960
cagagtttca attcttttcg ggcaccgctg ttggggtcgg tgtacatgct ggtgggctca   25020
tccatggtgt gtgtgctcct taagcgtggg ttactggtta ttgtcgtggg cgagtgctac   25080
ggcgagaata atgatggcga gggtttcagc gatcagtatg ggtgttgtga tcatttagtg   25140
```

```
tctcggggat tattggtgag tgttgatgca cctaggaggg tggcgagggc gcatgcggcg   25200
atggtggcga gggctgcctt gtgtggggtg ccggttgcgt acatccatgt gatgatgccg   25260
ccttggatcc aggctagact ggtgaagaac gtttcgtaac tgtgtagctc aatgttgttg   25320
ttgggtgtgt tcatgcttgc tcctgaagaa tggtgttgat ggttttataa atgttgtaca   25380
ggtcggtttc gatagataac agttggttga tttggtggtc gagatcaatg tctgggttga   25440
gggtgtcgat gcgggcggcg atatcggtgg cggtgcgtag gcttactgct gcaccgtgga   25500
tgatgtggca catgtcggtg aggccgactt tggcgatata gtgtgacatg agaggcataa   25560
taggtgtgct gtcttctctgg tcagcgtgaa gggttgatgg acatatcctc tacctgtggt   25620
ttgtcttcgg tgccggagac ttggcagaag actttcacat gcgtcttgga tgctccggcc   25680
tgtttggcgg tggcaccgta ggcgatagta aaggtgtctt tgtgggcgcc gatgactttg   25740
tgtaggaaga ggtcgatgtc ggggttgccg ttccatttga caccgttttc tgcggctgtc   25800
tgggtggctt tctgattgca ggcgtgtgcg gcggtgatca tggtgagacc cttgctggtt   25860
tcttcacccc ttgcttgggc ttgccggtgg gctttggcct gctcggcttg tagggagcgg   25920
actgctgcgg cctggcgggc cttcttctca gccttgcgct gctggacggt tttgggtgtc   25980
cattcggtgt tggctgtggt tacctgtggt gcggttgtg aggcgagtgg cggattgtcg   26040
tctggggctg gcatgaagga tgctgcggca ataatggcga ctgtggcgcc tgcgatggtg   26100
tagcctgttt tcttgttcat gattttatgt tccccttttcc ggggtgttgt tcgttgctga   26160
catggttaat actttcagcg gctgggccca ctgtcaaggc tgcgctcagt ttgtgtgagc   26220
gtttcttgtg tggctagggg tgatggcttc tttcgcccaa taggatgtgc caccgctggt   26280
ccagtatccg agtttgttgc gctgcatgcc cttggcgtcc atctcgtcga tagtgaggca   26340
cctgcggcga ttggggcctg tcttgacccc gtggtcgcct gtccggtgca tgtcgcctga   26400
ggtggtactc gtgaatgttt catggcagat ggtacagtgc tctggtcgat atccggtgat   26460
tgtgctatcg cacttgtggc atgtccattc catgattgct cctatttccc attataagac   26520
ttcctgtagt gccatttttag cgccttgcgg gtcttggggg tacaactata taggtcaggt   26580
gtttctaggc gattctaggc tcattgtgtg tggctgtggt tttatcgggc acacagggtg   26640
agcaggtggc caacattgat gcgggtcaca ttccagtaga gttgcgtggc ttccccactg   26700
gtgagcggct tccactcgtc atggctgaac acggtgccat cggatgcgat gaacgtgttg   26760
gggcgtagct tgtggagttc ggcttccacg ctctgccggt aggcttcggc gaggccctca   26820
aaatccatgt ggtcgcaggg gaggttttcg aggcgtgtca ggtcgaaggg tgtggggcag   26880
tcgtagctgg cggggggtgta gagctgggtg aagtggttgg cgatcttctg catcatgatt   26940
ccttttctga tgatggtgtg ttgagggttt atcgggtgga tgcgacaagg atggcgtcta   27000
catcgatcat gtcgatgaga tcgtggagtt cctcggcctc gttctcagtg agtggctgcc   27060
aggcgtagtc gccgtatacg gcgccgtcga gggtgacagt ccacggggc cggatgagtc   27120 gtatggcttc ttgtacttta gcgtggtaca tgcggcgcac catatccaga tcgatgtcgt   27180
ctgaatggtt tccggtgagg ctgtggaggc tgagcgggtc gatgtctgtc tgcctgtaga   27240
gggatgtgaa ggatggggtg atgagtgtgc catccatgag tgtgctccctt tcggtggttg   27300 taggggttgt tgtggtttct agagtgtgcg ggctgcgacc ccacagtcaa ggtgtcgctc   27360
aaactcagtg agcgtttcat atgggtgtgt tgggtgtgac agatgtcact taagccttga   27420
tggcctctct cagcgcctca aatcttctag gggtaggatt atgaagggtt ggccctgctg   27480
atcgattcta ggccccatac agggcgtctg aggggtgtgt ctgagtgata gtgggtgtgg   27540
```

```
cagatgatct agcgagtcaa ggtgccgagc tgagacataa gatctatcat ctaggtgtgt   27600
gagatgtatc acatcctccc ggcttggtgt gcaccctcaa ggccaccag tcgatctgac    27660 gtggagggtg tagcccagaa atactgttta aagccttcac acggcgccta ggagcgcctt   27720
acagggtggg ggctaggtat ttataccccc agcacattct gatcgattct agacgcctac   27780
aggagcccga tacacgatca gccatccaga cgcagatcat cagcacctat catggttagc   27840
taagcctcaa ctatgtggac agtgttggtt actgtggggg aagaaggaca cggtaaaaga   27900
aagaggggga gtatcagctt taaagcctta aggtcttagc gcttagcacc gatggtctta   27960
gcagttagca ccgagccccc tcaagggctc ggcatcagcc cgaacaggca cagccatgaa   28020
aggagtacac gccatcaggg aaggctttcg agtacgagga gcctcagcga cgagtactcg   28080
aaagcctgag ggaacaccca tcagcactga tgagcctagc gtattcggaa aggacacaag   28140
agtgaagtgt gacagctgtc cgggagtgaa ccccgttctg actaggggtt tcagccttaa   28200
ccaccctcaa aggttacaag actctaagaa aatttaagga aaagtttagg tttaattttt    28260
ggacctttac taccaaaaac acccgtttac agccctcaaa cccgcctata gagccaaaac   28320
caccagtttg actcatccca ggtggggtat gataggctgg acaggtagcc agctggacgc   28380
aaggccggaa agtgctaacg cactttccaa cctcgcttac catcagtcta ccaaacactt   28440
aaagacctaa gggcttagcg ctaaggtgct gatagcttag caccgagccc cctcaagggc   28500
tcggcatcag tcttaaagcc ttaaatactt aaagtaacta taaaacttta aagcttaac    28560 acttaaggat ataaactta catcagtgtt taagacttaa aaacttaaaa taactattaa    28620
gacttaaagt aactataaaa cattaaagac cttaagtact taaagttaac catcagtctt   28680
aaactttact atgataacct ataagtctta aagcttatag gtataataat ataatataag   28740
tattaaagct tataagttat aaaagtttta gaagagttaa agggttaact tctttacttc   28800
tcttctctct ttggttcttt ctctcttctc ttcttttctt catcgggga gaagaggaac     28860 ctttaacgtc aacgctgatg gacttttcgc cgtgtgtctc gtgtgcttct ggtcgcaagc    28920
tcccatcgca cactccccac actctttcac ctgtgtccct ttcaggctta gcgtgttcag    28980
ctgaaggcgt acagcgtgtc acgcttaaac ccttaacacc aggtaagact taaagtgcat   29040
attataagta gaagacttta aaaccttaag ggtgttcctg cttagcctgt gtcctttaac    29100
gctaggcgct aagccgtgaa acgtgaacac ccatccaccc ctcttctttt taccgtgtcc    29160
ttcttctttt gacaccgctg gggggcgatg tgatcttttt aacatgccag ggggtgcggg   29220
tagaaaacaa ccaccccacc acaaacagaa caccccctca aacgcacaaa acagcccca    29280 ggatcgatga acagggcaag ggcaaggtat tcataccccc agacgattcc aggccgttag   29340
agaggcaaat aagacccgta cagggctagg tgaggaatag acacatcatg gcacgcacca   29400
atcgcacagc tagccaagcc caccgacgct ggcggcaacg actcatcacc caagcccaac   29460
aacaaggcca aaccgaatgc ccactctgcg gagtcaccat cacctgggac acacacgacc   29520
taccaaccag ccccgaagcc gaccacatca cacccgtcag caggggagga ctcaacaccc    29580
tcgacaacgg gcaaatcatc tgcagaacat gcaacagaag caaaggcaat cgcagcgaac   29640
caaacatcaa attccaacaa caaaccacaa aaacattgat tccatggtga caaacccgcc   29700 aaccccacc ggggacaccc cctgcacagg cgtgcaaga                           29739
```

<210> SEQ ID NO 2
<211> LENGTH: 863
<212> TYPE: DNA

<213> ORGANISM: Bacteriophage PA6

<400> SEQUENCE: 2

| | | | | | |
|---|---|---|---|---|---|
| ggtgtgtggt | gagatacatt | cctgcagcgc | atcactctgc | cggctctaat | aatccggtga | 60 |
| acagggttgt | gattcatgca | acatgcccgg | atgtggggtt | tccgtccgcc | tcacgtaagg | 120 |
| ggcgggcggt | gtctacagca | aactatttcg | cttccccatc | gtctggtggt | tcggcgcatt | 180 |
| atgtgtgtga | tattggggag | acggtgcaat | gcttgtcgga | gtctacgatt | ggttggcatg | 240 |
| ccccgccgaa | tccgcattct | ttgggtatcg | agatttgcgc | ggatgggggt | tcgcatgcct | 300 |
| cgttccgtgt | gccggggcat | gcttacactc | gggagcagtg | gcttgatccg | caggtgtggc | 360 |
| ctgccgttga | gagggcggcg | gtgctgtgta | gacgtttgtg | tgacaaatat | aatgttccga | 420 |
| aaaggaaact | gtcggctgcc | gatttgaagg | ctggcaggcg | gggtgtgtgt | ggccatgtgg | 480 |
| atgttacgga | tgcgtggcat | cagtcggatc | atgacgatcc | tgggccgtgg | tttccgtggg | 540 |
| acaaatttat | ggccgtcgtc | aacggcggca | gtggagatag | tggggagtta | actgtggctg | 600 |
| atgtgaaagc | cttgcatgat | cagattaaac | aattgtctgc | tcagcttact | ggttcggtga | 660 |
| ataagctgca | ccatgatgtt | ggtgtggttc | aggttcagaa | tggtgatttg | ggtaaacgtg | 720 |
| ttgatgcctt | gtcgtgggtg | aagaatcctg | tgacggggaa | gctgtggcgc | actaaggatg | 780 |
| ccctgtggag | tgtctggtat | tacgtgttgg | agtgtcgtag | ccgtcttgac | aggctcgagt | 840 |
| ctgctgtcaa | cgatttgaaa | aag | | | | 863 |

<210> SEQ ID NO 3
<211> LENGTH: 29275
<212> TYPE: DNA
<213> ORGANISM: Bacteriophage 103609

<400> SEQUENCE: 3

| | | | | | |
|---|---|---|---|---|---|
| cctcccttt | gtggattgtc | tgtttgtcga | cttttgtgt | tggtggtgag | tgctgtgcag | 60 |
| cctgagcttc | ctgggtctcg | tgagtggtgt | ggggagacgc | gtcgttggtg | gcgtgtgtgg | 120 |
| ggtgaggata | gccgtgcatc | gtacgtgtct | gatgaggagt | ggctgtttct | cttggatgct | 180 |
| gcggtgattc | atgattgtgt | gtggcgtgag | ggtcgcgcgg | atttggtggc | ttcgcttcgt | 240 |
| gctcatgtga | aggcttttat | gggtatgttg | gatcggtatt | cggttgatgt | ggcgtctggt | 300 |
| ggccgtggtg | ggggttctgc | ggtggcgatg | attgaccggt | atcggaagcg | taaaggggcc | 360 |
| taatgtcgag | tgtggttggt | tctcaggtgc | ctcgtcatcg | ggtggctgcg | gcgtattcgg | 420 |
| tgtctgctgg | cggtgatgct | ggggagttgg | gtcgtgcgta | tgggttgacg | cctgatccgt | 480 |
| ggcagcagca | ggtgttggat | gattggctgg | ctgtcggtag | caatggcagg | cttgcttcgg | 540 |
| gtgtgtgtgg | ggtgtttgtg | cctcgccaga | atggcaagaa | tgctattttg | agattgtgg | 600 |
| agttgtttaa | ggcgactatt | cagggtcgcc | gtattttgca | tacggctcac | gagttgaagt | 660 |
| cggctcgtaa | ggcgtttatg | cggttgaggt | cgttttttga | gaatgagcgg | cagtttcctg | 720 |
| acttgtatcg | tatggtgaag | tcgattcggg | cgacgaatgg | tcaggaggct | attgtgttgc | 780 |
| atcatccgga | ttgtgccacg | tttgagaaga | agtgtggctg | cagtggttgg | ggttcggttg | 840 |
| agttgtggc | tcgttctcgg | ggttctgctc | gcgggtttac | ggttgatgat | ttggtgtgtg | 900 |
| atgaggctca | ggagttgtcg | gatgagcagt | tggaggcttt | gcttcctacg | gtgagtgctg | 960 |
| ccccgtctgg | tgatcctcag | cagatttttcc | ttggcacgcc | gcctgggccg | ttggcggatg | 1020 |
| gttctgtggt | gttgcgtctt | cgtgggcagg | ctttgtctgg | tggtaaaagg | tttgcgtgga | 1080 |
| cggagttttc | gattcctgac | gagtctgatc | cggatgatgt | gtcgcggcag | tggcggaagt | 1140 |

```
tggcggggga tacgaatccg gcgttggggc gtcgcctgaa ttttgggacc gtaagcgatg   1200
agcatgagtc gatgtctgct gccggttttg ctcgggagcg gcttggctgg tgggatcgtg   1260
gccagtctgc tacgtctgtg attccggcgg ataagtgggc tcagtctgcg gtggatgagg   1320
cgaagctttc tggcgggaaa gtgtttggtg tctcgttttc tcgttcgggg gatcgtgtcg   1380
cgttggcggg tgccggccgg actgatgctg gtgttcatgt tgaggttatt gatgggctgt   1440
cggggacgat tgttgatggt gtgggccggt tggctgactg gttggcggtt cgttggggtg   1500
atactgaccg gatcatggtt gccgggtctg gtgcggtgtt gttgcagaag gcgttgacgg   1560
atcgtggtgt tccgggccgt ggcgtggtgg ttgccgatac tggtgtgtat gtggaggctt   1620
gtcaggcgtt tcttgagggt gttcgttcgg gtgttgtgtc tcatcctcgt gctgattctc   1680
gccgtgacat gttggatatt gctgtgaggt cggctgtgca gaagcgtaag gggtctgcgt   1740
ggggttgggg ttcctcgttt aaggatggtt ctgaggttcc tttggaggct gtgtcgctgg   1800
cgtatcttgg tgcgaaaaca gttaaagtga agcggcgtga acggtctggt aggaagcggg   1860
tgtctgtggt atgaacgtgg acgagttggc tctgattgag ggcatgtacg atcgtatcca   1920
aaggttgtct tcgtggcatt gccgtattga gggctactat gagggctcga gccgggtgcg   1980
tgatttgggg gtggctattc ctccggagtt gcagcgtgtg cagactgtgg tgtcgtggcc   2040
tggtatagct gtggatgctt tggaggagcg tctggattgg cttggctgga ctaatggtga   2100
cggctacggc ctggatggtg tgtatgctgc gaatcggctt gctacggctt catgcgacgt   2160
ccaccttgat gcactaattt ttgggttgtc gtttgttgcg atcattcctc atggtgatgg   2220
tacggtgtcg gttcgtccgc agtcaccaaa gaattgtacg ggcaagtttt cggctgacgg   2280
gtctcgtttg gatgcgggtt tggtggttca gcagacgtgt gatcctgagg tggttgaggc   2340
tgagcttttg cttcctgatg tgattgttca ggtggagcgg cggggttcgc gtgaatgggt   2400
tgaggtggat cgtataccga atgtgttggg tgctgttccg cttgtgccta ttgtgaatcg   2460
tcgccgtacg tctaggattg atggccgttc ggagattacg aggtctatta gggcttacac   2520
ggatgaggct gttcgcacac tgttggggca gtctgtgaat cgtgattttt atgcgtatcc   2580
tcagcgttgg gtgactggtg tgagcgcgga tgagttttca cagcctggct gggtcctgtc   2640
gatggcttct gtgtgggctg tggataagga tgatgatggt gacactccga atgtgggggtc   2700 gtttcctgtc aattcgccta caccgtattc ggatcagatg agactgttag cgcagttaac   2760
tgcgggtgag gcggctgttc cggaacgcta tttcgggttt atcacgtcta acccacctag   2820
tggggaggct ttggctgccg aggaatctcg gcttgtgaag cgtgctgagc ggcgtcaaac   2880
gtcgtttggt cagggctggc tgtcggttgg tttttggct gccaaggcgt tggattctcg   2940
tgttgatgag gccgattttt ttggtgatgt tggtttgcgt tggcgtgatg cttcgacgcc   3000
tacccgggcg gctacggctg atgctgtgac gaagcttgtt ggtgccggta ttcttccggc   3060
ggattctcgg atggtgttgg agatgttggg tttggatgat gtgcaggttg aggctgtgat   3120
gcgtcatcgt gccgagtctt cggatccgtt ggcggcactg gctgggggcta tttctcgtca   3180 aactaacgag gtatgatagg cgatggcttc gggtgctgtg tcgaggcttg ttgcgactga   3240
gtatcagcgt gaggcggtca ggtttgctgg gaagtatgcg gggtattatt cggagcttgg   3300
tcgtttgtgg cattccggga agatgacaga tgtgcagtat gtgcgtttgt gtgtggagtt   3360
ggagcgtgcc ggccatgatg gttcggcatc gttggctgcc aggtttgtgt cggattttcg   3420
ccggttgaat ggtgtggatc cgggtttgat tgtgtatgac gagtttgatg ctgcggcggc   3480
```

```
tttggctagg tcgttttcga ctatgaagat tcttgagagt gacccggata gggcgaatga    3540
cacgattgat gcgatggctg cgggttttga tcgggctgtt atgaatgctg gccgtgacac    3600
ggttgagtgg tctgcgggtg cgcagggtag gtcgtggcgc agggtgactg atggtgatcc    3660
gtgtgctttt tgtgccatgt tggctacgag gtcggattat acgactaagg aaagggcact    3720
cacttccggt catacgcggc gtcataagcg tggtggtaag cgtccgtttg gttcgaagta    3780
tcatgatcat tgtggttgta cggtggttga ggttgttggc ccttgggaac caaatagggc    3840
tgatgccgag tatcggagga cgtatgagaa ggcccgtgag tgggttgatg atcatgggtt    3900
gcagcagtcg cctggcaata ttttgaaggc tatgcgtact gttggtggca tgagataatt    3960
tgatgtggtt tccggttgtg cgccgccggt tattggtgca cagggttgtc tcccgcacgg    4020
gggtcaacaa tgttgtgttg ttttccgcaa ggagtgtagg gttaggctat ggccgatcag    4080
agtgttgagg aacagaatgt tgacaatgat gctgttgagc ccgaaaggg tggagacatt     4140
gttgatgttg tgaaggatgg gcaggctgcc ggcgatgatc atgccggtga tgtttccgtg    4200
aagggtgagg cttctgggcc gtctgggact gattggaagg cggaggcccg taagtgggag    4260
tctcgtgcta aaagtaattt cgccgagttg gagaagcttc gtacatcgag tgacgattct    4320
ggatctacta ttgatgagct tcgccgcaag aatgaggaac tcgaagacag gatcaacggg    4380
tttgttcttg agggtgtgaa gcgcgaggtg gcttcagagt atggtttgtc cagtgatgcg    4440
atcgctttct tgtcgggtgg cgataaggag tcgcttgccg agtctgcgaa agctttgaag    4500
ggtttgattg accatagtag tggtggcgcg ggtgtgcgcc gtcttgcggg gagtgccccc    4560
gttgatgatg ttaaacgacg tgagggtgtc gcgtttgtgg atgctcttgt caataattct    4620
aggagatgat ttctgatggc tgacgatttt ctttctgcag gtaagcttga gcttcctggt    4680
tctatgattg gtgcggttcg tgaccgtgct atcgattctg gtgttttggc gaagctttcg    4740
ccggagcagc cgactatttt cggcccggtg aagggtgccg tgtttagtgg tgttcctcgc    4800
gccaagattg ttggcgaggg cgaggttaag ccttccgcgt ctgttgatgt ttcggcgttt    4860
actgcgcagc ctatcaaggt tgtgactcag cagcgtgtct cggacgagtt tatgtgggct    4920
gatgctgatt accgtctggg tgttttgcag gatctgattt ccccggctct tggtgcttcg    4980
attggtcgcg ccgtggatct gattgctttc cacggtattg atcctgccac tgggaagcct    5040
gccgcggctg tcaaggtgtc gctggataag acgaagaaga cggttgatgc caccgattcc    5100
gctacggctg atctggtcaa ggctgtcggc cttatcgctg gggctggttt gcaggttcct    5160
aacggtgttg ctttggatcc ggcgttctcg tttgctctgt ctactgaggt gtatccgaag    5220
gggtctccgc ttgccggtca gccgatgtat cctgccgccg gtttgctgg tttggataat     5280
tggcgtgggc tgaatgttgg tgcttcttcg actgtttcgg gtgccccgga gatgtcgcct    5340
gcctctggtg ttaaggctat tgttggtgat ttctctcgtg ttcattgggg gttccagcgt    5400
aacttcccga tcgagctgat cgagtatggt gacccggatc agactggccg tgacttgaag    5460
ggccataatg aggttatggt tcgtgccgag gctgtgctgt atgtggctat cgagtcgctt    5520
gattcgtttg ctgttgtgaa ggagaaggct gccccgaagc ctaatcctcc ggccgagaac    5580
tgatttattg ttgcggtgat gtgtcaatgt gcaggggtg tgttgatgg gtatcattt       5640
gaagcctgag gatattgagc ctttcgccga tattcctaga gagaagcttg aggcgatgat    5700
tgccgatgtg gaggctgtgg ctgtcagtgt cgcccctgt atcgctaaac cggatttcaa     5760
atacaaggat gccgctaagg ctattctgcg cagggctttg ttgcgctgga atgatactgg    5820
cgtttcgggt caggtgcagt atgagtctgc gggtcctttc gctcagacta cacggtctag    5880
```

```
tactcccacg aatttgttgt ggccttctga gattgccgcg ttgaagaagc tgtgtgaggg      5940
tgatggtggg gctggtaaag cgttcactat tacaccgacc atgaggagta gtgtgaatca      6000
ttctgaggtg tgttccacgg tgtggggtga gggttgctcg tgcgggtcga atattgacgg      6060
ctacgctggc cctttgtggg agatatgata tgaccagttt tccttatggt gaaacggttg      6120
tgatgcttca accgactgtt cgtgtcgatg atcttggtga caaggttgag gattgggagc      6180
atcctgtaga aaccgtgtac cataacgtgg ccatctatgc ttccgtttcg caggaggatg      6240
aggccgcggg gcgtgactct gactatgagc attggtcgat gctgttcaag cagcctgttg      6300
tgggcgctga ttatcgttgc aggtggcgta tccggggtgt tgtgtgggag gctgacgggt      6360
ctcctatggt gtggcatcat ccgatgtctg gctgggatgc tggtacgcag gttaatgtga      6420
agcgtaagaa gggctgatgg gtagtggctc aggatgtgaa tgtgaagctg aacttgccgg      6480
gtattcgtga ggtgttgaag tcttctgggg tgcaggctat gttggctgag cgtggcgagc      6540
gtgtcaagcg tgcggcctcg gcgaatgtgg gcggtaacgc tttcgataag gcccaatacc      6600
gtaatggttt gtcgtcggag gtgcaggttc accgtgttga ggctgtcgct cgtataggca      6660
ccacatataa gggtgggaag cgtattgagg cgaagcatgg cacgttggct cgttcgattg      6720
gggctgcgtc gtgatcgtct acgatgaccc caggaagtgg gctaaacgcg tgctcaagga      6780
tgatggctgg ctgtctggga taccgtgtac ggggacggtg cctgaccggt ttgagggtga      6840
ccttatttgg ttggctcttg atggtggccc gcagttgcat gttcgtgagc gagtgttttt      6900
gcgggtgaat gtgttttctg atacgccgga tcgtgctatg tcgttggcgc gtcgtgttga      6960
ggctgttctg gctgacgggg tggacggtga ccctgtggtg tactgtaaac ggtctactgg      7020
tcctgatttg ctggttgatg gtgcacgttt tgatgtgtat tcgctgttcg agctgatatg      7080
taggccggca gagtctgaat aagcttattg tttttgtttt aatgtaattg tttgatattt      7140
aatgggggtt gtgatggctg caacacgtaa agcgtctaat gttcgctctg ctgttactgg      7200
tgacgtgtat attggtgacg cgcacgccgg tgacactatt gatggtgtga agacggttcc      7260
ttctgggctt accgcgttag ggtatctgtc ggatgacggg tttaagatta agcctgagcg      7320
taaaacggat gatttgaagg cttggcagaa tgcggatgtt gttcgcacgg tggctacaga      7380
gtcgtctatc gagatttctt tccagctgat cgaatccaag aaagaagtta ttgaactgtt      7440
ttggcagtcg aaggttactg ccggatccga ttcgggttcg ttcgatattt ctcctggtgc      7500
caccactggc gtgcacgctt tactgatgga tattgtggat ggcgatcagg ttattcgcta      7560
ctatttcccc gaggttgagc tcattgatcg tgacgagatc aagggtaaga atggcgaggt      7620
gtatgggtat ggtgtgacgt tgaaggcgta tcctgcccag attaataaga agggtgatgc      7680
ggtgtctggt cggggggtgga tgacggcttt aaaagctgat actcctccga ctcctcctcc      7740
ggccccggtt cctccgaagc ctgagcctga tccgaatccg ccgtctaata actgatacac      7800
atagtttgag ggattgttga tagatgagtg acacaggtta cacgttgaag attggtgacc      7860
gtagctgggt gttggcggat gcggaggaga cggctcaggc tgttcctgcc cgtgtgtttc      7920
gtcgtgcagc taagattgcc cagtcggggg agtctgcgga tttcgcccag gttgaggtga      7980
tgttttctat gctagaagcg gccgcccgg ctgatgcggg ggaggccctg gaggggcttc      8040
ctatggttcg tgttgccgag attttccgtc agtggatgga atacaagcct gacggtaagg      8100
gtgcctcgct gggggaatag tttggctcca cggcctgatt gatgattatc gtggggccat      8160
cgaatacgat ttccgcacca agtttggtgt ttctgtttat agtgttggtg gcccgcagat      8220
```

```
gtgttggggt gaggctgtcc ggctggctgg cgtgttgtgt accgatacgt ctagccagtt    8280
ggcggcccac ctgaatggtt ggcagcgccc gtttgagtgg tgcgagtggg ctgtgctgga    8340
catgctggat cattacaggt ctgctaatag tgaggggcag ccggagcctg tggcgaggcc    8400
tacgatgag cgtagggccc ggtttacgtc ggggcaggtg gacgatattt tggcgcgtgt     8460
tcgtgctggt ggcggggtgt ctcgcgagat taatattatg gggtgaatag tgtatgtctg    8520
gtgagattgc ttccgcatat gtgtcgttgt atacgaagat gcctggtttg aaggctgatg    8580
ttggtaaaca gttgtcgggt gttatgcctg ctgagggtca gcgttcgggt agtcttttg     8640
ctaagggcat gaagttggcg cttggtggcg cggcgatggt gggtgctatc aatgttgcta    8700
agaagggcct caagtcgatt tatgatgtga ctattggtgg cggtattgct agggcgatgg    8760
ctattgatga ggctcaggct aagttgactg gtttgggtca cacgtcgtct gatacgtctt    8820
cgattatgaa ttcggctatt gaggctgtta ctggtacgtc gtatgcgttg ggggatgcgg    8880
cgtctacggc tgcggcgttg tctgcttcgg gtgtgaagtc tggcgggcag atgacggatg    8940
tgttgaagac tgtcgcggat gtgtcttata tttcgggtaa gtcgtttcag gatacgggcg    9000
ctattttta cgtctgtgatg ccccgcggta agttgcaggg cgatgacatg ttgcagctta    9060
cgatggcggg tgttcctgta ctgtcttttgc ttgccaggca gacgggtaaa acgtcggctg   9120
aggtgtcgca gatggtgtcg aaggggcaga ttgattttgc cacgtttgcg gctgcgatga   9180
agcttggcat gggtggtgct gcgcaggcgt ctggtaagac gtttgagggc gctatgaaga   9240
atgttaaggg cgccctgggt tatcttggtg ctacggctat ggcgccgttt cttaacgggt   9300
tgcggcagat ttttgttgcg ttgaatccgg ttatcaagtc tatcacggat tctgtgaagc   9360
cgatgtttgc tgccgtcgat gctggtattc agcgtatgat gccgtctatt ttggcgtgga   9420
ttaatcgtat gccgggcatg atcacgagaa tgaatgcaca gatgcgcgcc aaggtggagc   9480
agttgaaggg catttttgcg agaatgcatt tgcctgtccc taaagtgaat ttgggtgcca   9540
tgtttgctgg cggcaccgca gtgttcggta ttgtggctgc cggtgtgggg aagcttgtcg   9600
cggggtttgc cccgttggcg gtgtcgttga agaatctgtt gccgtcgttt ggtgctttga   9660
ggggtgccgc cggcgggctt ggcggcgtgt ttcgcgccct gggtggcccc gtcgggattg   9720
tgatcggctt gttttgctgcc atgtttgcca ctaacgccca gttccgtgcc gctgttatgc   9780
agcttgtcgg ggttgttggc caggctttgg gccagattat ggccgctgtg cagccgctgt   9840
ttggttttggt ggctggtttg gtggcacggt tggctcccgt ttttggccag attattggtt   9900
tggttgccgg tttggctgcg cagcttgtgc ctgtgattag tatgctggtt gctcggctgg   9960
ttcctgtgat cacgcagatt attggtgcgg tgacacaggt tgccgcaatg ttgttgccgg   10020
tgttgatgcc ggtgttgcag gctgttgttg ctgtgatacg gcaggttgtt ggcgtgatca   10080
tgcagttggt gcctgttttg atgcctgtga ttcaacagat tttgggtgcg gtcatgtctg   10140
ttctgccgcc tatcatcggt ctgatccggt cgttgatacc agtcatcatg tcgattatgc   10200
gtgtggtggt gcaggttgtt tcggttgtgc tgcaggtggt ggcccgcatt attccggttg   10260
tgatgccgat tgtgacagct gtgatcgggt ttgttgcccg tattgttggt gctgtcgtgt   10320
cggctgttgc ccgtgttatt gctgctgttg cccgtgttat cggtgggtt gtggcccatt   10380
ttgtgtctgg ttttggcgcgt atgggttcgg ttattcaggc tggctggaat catattagag   10440
cgtttacgtc tgcgtttatt aacggtttca agtcggttat ttctgccggt gttgccgcgg   10500
ttgtgggggtt ttttgcccgg cttggttctt cggttgcttc tcatgtgagg tctggttta   10560
acgcggctcg tggtgctgtt tcttctgcga tgaatgctat ccggagtgtt gtgtcttcgg   10620
```

-continued

```
tggcgtctgc tgttggcggg tttttcagtt cgatggcgtc tagggttcgt agtggtgctg    10680
tgcgcggttt taatggtgcc cggagtgcgg cttcttctgc tatgcatgct atgggtccg     10740 ctgtgtctag tggtgtgcat ggtgtgctgg gttttttccg gaatttgcct ggcaatattc    10800
ggcgtgcgct tggtaatatg gggtccttgt tggtgtctgc tggccgtgat gtggtgtctg    10860
gtttgggtaa tggtatccgg aatgctatga gtggcttgtt ggatactgtg cgtaatatgg    10920
gttctcaggt tgctaatgcg gcgaagtcgg tgttgggtat tcattcccg tctcgggtgt     10980 ttcgtgacca ggttggtcgc caggttgttg ccggtttggc tgagggtatt actgggaatg    11040
ctggtttggc gttggatgcg atgtcggtg tggctggtcg gcttccggat gctgtggatg     11100
cccggtttgg tgtgcgatcg tctgtgggct cgtttacccc gtatggcagg tatcagcgtg    11160
ctaagggtga gagtgttgtg gtgaatgtga atggacctac gtatggtgat cctaacgagt    11220
ttgcgaagcg gattgagcgg cagcagcgtg acgctttgaa cgcgttggct tacgtgtgat    11280
tgggggtgtt gttcatgttt cttcctgacc cgtctgatcg ttctggtttg actgtgacgt    11340
ggtttatgga tccgctgttt ggtggggagc gtgtgcttca tttgacggat tatacgggtg    11400
cgtctcctgt catgttgttg aatgattcgt tgcgcggttt gggtgttccc gaggtggagc    11460 attttctca aacacatgtt ggggtgcacg gctcggagtg gcgcgggttt aatgtgaagc     11520
ctcgcgaggt gacgctaccg gtgttggtgt cgggtgttga cccggatccg gatggcgggt    11580
ttcgtgacgg tttttgaaa gcctatgacg agttgtggtc tgcttttcct cctggcgagg     11640 aggggagtt gtcggtgaag accccgtctg tcgtgagcg tgtgctgcgg tgccggtttg      11700
attcggctga tgacacgttt acggtggatc cggtaaatcg tggctatgcg cgctatctgt    11760
tgcatttgac agcttatgac ccgttttggt atggggagga gcaaaagttt cgtttcagta    11820
acgctaagtt gcaggattgg ctgggtggcg gccctgtcgg caaggatggc acggcttttc    11880
ctgtggtgtt gacgcctggt gttggttctg gctgggataa tctgtctaat aagggtgatg    11940
tgcctgcgtg gcctgtgatt cgtgttgagg ggcctttgga gtcgtggtct gtgcagattg    12000
atggtttgcg tgtgtcttcg gattatcctg tcgaggagtt tgattggatc acgattgata    12060
cggatcctcg ccagcagtct gcgttgttga atggggttga ggatgtgatg gatcgtttga    12120
aggagtggga gtttgcgcct atcccgcctg gcggttctaa gagtgtgaat attgagatgg    12180
ttggtttggg tgccattgtt gtgtcggtgc agtacaggtt tttgagggct tggtgaatag    12240
ttgatggctg gtcttgtccc gcatgtaacg ttgtttacgc cggattatcg ccgtgtggcg    12300
cctatcaatt tttatgagtc gttgaagttg tcattgaagt ggaatggttt gtcgacgctg    12360
gagttggtgg tgtcggggga tcattccagg cttgacgggt tgactaggcc gggtgcgcgg    12420
cttgtggtta attatggtgg tggccagatt ttttctgggc ctgtgcgtaa ggttcatggt    12480
gtgggtccgt ggcgttcttc gcgggtgact atcacgtgtg aggatgatat ccggctgttg    12540
tggcgtatgt tgatgtggcc tgtgaattat cgtcctggta tggttggtat ggagtggcgt    12600
gccgacaggg attatgccca ctattcgggt gcggctgagt cggtggctaa gcaggtgttg    12660
ggggataatg cttggcgttt tccgcctggt ttgtttatga ccgatgatga gcgtcgtgga    12720
cgctatatta aggattttca ggtgcggttc cacttgtttg cagacaagtt gttgccggtg    12780
ttgtcgtggg ctcggatgac tgtcacggtg aaccagtttg agaatgcgca gtttgatcag    12840
cggggtttgc tgtttgattg tgtgcctgct gtgacccgga agcatgtgtt gactgccgag    12900
tctggttcga ttgtgtcgtg ggagtatgtg agggatgccc ctaaggctac ttcggtggtg    12960
```

```
gttggtggcc gcggcgaggg taaggatcgg ctgttttgtg aggatgttga ttcgatggcc   13020
gagggggatt ggtttgatcg tgtagaggtg tttaaggatg cccgtaacac ggattctgag   13080
catgtgcatc tcatcgatga ggctgagcag gtgctgtccg agttaggggc cacgtcgggg   13140
tttaagatcg agttggctga gtcggatgtg ttgcggtttg gccaggcaa tctgatgccg    13200 ggtgatctta tctatgtgga tgtgggttct ggccctattg cggagattgt gcggcagatt   13260
gatgtggagt gtgattcgcc tggtgatggt tggacgaagg tgactcctgt tgcggggat    13320 tatgaggata atccgtcggc gttgttggct cgccgtgtgg ctggtttggc tgcgggtgtg   13380
cgggatttgc aaaagttttg acaagtgatt ggggtttgtt gtgggtattg tgtgtaaagg   13440
gtttgatggt gtgttgaccg agtatgattg ggctcaaatg tctggtctga tgggtaatat   13500
gccgtccgtg aaagggccgg acgattttcg tgtcggcacg acaattcagg gtgccacagt   13560
gttgtgtagt gttttgccgg ggcaggcttg ggctcacgga gtgatgtgca cgtcgaatag   13620
tgttgagacg gtgacagggc agctgcctgg cccgggcgag acccgatacg actatgttgt   13680
tctgtctcgg gattgggagc agaacacagc caagttggag attgttcccg gtggccgtgc   13740
ggagcgtgcc aggatgtgt tgcgtgccga gcctggcgtg tttcatcagc aactgttggc    13800
gactttggtg gtgtcgtcta acgggttgca gcagcagctg gataggcgtg ctatagcggc   13860
ccgtgtggcg tttggcgagt ctgcggcttg tgatcctacc cctgtggagg gtgaccgggt   13920
gatggttcct tcggggctg tgtgggctaa tcatgctaac gagtggatgt tgttgtctcc    13980
gaggattgag acgggttcta agtcgatcat gtttggcggg tctgctgtgt atgcttacac   14040
gatcccgttt gagcggccgt ttagtagtgc gcctgttgtg gtggcgtcta tggctacggc   14100
ggctgggggc acgcagcaga ttgatgtgaa agcctacaat gtgactgcca aggattttgg   14160
tttagcgttt atcacgaatg acgggtctaa accgaatggt gtgcctgcgg tagctaactg   14220
gattgctgtc ggcgtgtaat gcgctgcttg tgtgtgcggg atatgttgtg gtggttgtag   14280
tggtaggggg ctgtagtgtc atggcttaca cccacactcg tagcctctat ttgtaccgct   14340
atcgctactg tccttggttc gattcaggcg gttacttaca ggtcgaagaa gaggcttagg   14400
cagttgtctg cacaggttga tgcgatggaa gaatacacat ggaatattcg ccatattgtt   14460
catcgctata acgcgaattt gcctgagaat gttgagcctg taaaaatgcc tgatttgccc   14520 gagttttttga aggatactgt tgatagtggt gggggtgaa ttgtgaggga gttggaggaa    14580
gagaaacggc agcgccgcaa ttttgagaag gtttcattgg tgttgctgtt tttgtcgctt   14640
gtgctactgg tggcgatggc tgggggtgct ttgcggtatg gttctgtggc ttcgcaaagg   14700
gattcggagc aggcgagggc ccagtctaat ggtacagccg ctaaagggtt ggccagccgt   14760
gtgcggcagg tgtgtgcttc ggatgggcag gagtcggtgc ggcttcatca gtctggtttg   14820
tgtgtggatg ctgtgcgtgt tgagcgtagc gtgcagggtg tgccgggccc tgccggtgtg   14880
cgcggcccgc aaggaccggc tggtgttgca ggtgttgacg gccgtgacgg tgtgaatggt   14940 tcggcggtg ttgtggggcc tgtgggtccg cagggttctc cggtttgaa tggtgtggct     15000 ggcccggacg ggttgcctgg cgtgaatgga tcggatggcc atgatggtgt tccaggtcgt   15060
gcaggtgctg acggtgtgaa cggcgttgac ggtcggatg gttcggccgg tgagcgcggt    15120
gatgtgggcc cttcaggtcc tgccggcccg caaggtgcac agggtgaacg gggtcctatt   15180
gggcctcagg gtccgcaggg ttctgccggt gctgacggca cgaatggtaa agacggtaaa   15240
gatgggcgct cggttgtgtc tgtgtactgt tccgagggcc gctggttgt gaaatatagt    15300 gacggtgtgg cttctacaat atcgagctcg gtggcctgcc agggtgtgaa accgtcgcct   15360
```

```
atagtgacta tatcatccca caagtaaaaa agaaaaggga agggtgttac tagtgttgat   15420
tgtggtgtta ggtggtgtgt ggtgagatac attcctgcgg cgcatcattc tgccggctcg   15480
aatagtccgg tgaatagggt tgtgattcat gcgacgtgcc cggatgtggg gtttccgtct   15540
gcctcgcgta aagggcgggc ggtgtctaca gcaaactatt tcgcgtcccc atcgtcgggt   15600
ggttcggcgc attatgtttg cgatattagt gagactgtgc agtgcttgtc ggagtctacg   15660
attgggtggc atgccccgcc gaatccgcat agtttgggta tcgagatttg cgcggatggg   15720
ggttcgcacg cctcgttccg ggtgccgggg catgcttaca ctcgggagca gtggcttgat   15780
cctagggtgt ggcctgcggt ggagaaggct gccatcctgt gtagacgttt gtgtgacaaa   15840
tataatgttc cgaagaggaa gcttagtgca gccgatttga aggctggtag gcggggtgtg   15900
tgcggccatg tggatgtgac ggatgcgtgg catcagtcgg atcatgacga tccggggccg   15960
tggtttccgt gggacaggtt tatggccgtt gtcaacggca aagatgagag tggggagtta   16020
actgtggctg atgtgaaagc cttgcatgat cagattaaac aattgtctgc tcagcttact   16080
ggttcggtga ataagctgca ccatgatgtt ggtgtggttc aggttcagaa tggtgatttg   16140
ggtaagcgtg ttgacgcctt gtcgtgggtg aagaatccgg tgacggggaa gctgtggcgc   16200
acaaaggatg ctttgtggag tgtctggtat tacgtgctgg agtgtcgtag ccgtattgac   16260
aggcttgagt cgactgtcaa cggttttgaaa aagtgatggt ggtttgttgt gggtaaacag   16320
ttttggttgg gcttgtttga gcgtgccctg aaaactttta ttcaaacgtt tgttgctgtg   16380
cttggtgtga ctgcgggtgt cacgtatacg gcggagtcgt ttcgcggttt gccgtgggag   16440
tcggccctga ttacggccgg ggttgctgca atactgtcgg ttgctacctc gtttggtagc   16500
ccgtcgtttg tggccggcaa acctaaaacc acggttgtgg atgctggtct tgttccaccg   16560
gatgatgggg gcatggttga ccgcactcg gtggatgtgt cggatcctgg catgattgag   16620
ccgacagatg atgtggatgg ttttgtcggc tatgtgccga ggcgtgcagc cgagtctgag   16680
gttggcacga tagagccgat cgaatgataa gtgaacatag atgtgtgccc cagcggtgct   16740
gccacgatcg tgtggtggtt gccgctgggg cactatttct gtttatgcgg tgtggctata   16800
attcgttgcg gtcgatggtg tcttcgagca tctgatacag gtggaggcag gtagagatcg   16860
tatcgctggc ctggtctaga acgttccggc cgataacgtt tttgtggttg tcgcggtggc   16920
ggatgatagc ccacatgatc tcgtcggctg ccgcctgcaa tagttttgcc tggtatgcga   16980
ttccggcgag ccagtctagt gcttcctggc ttgcataggg gctctggtcc tcgctgttgt   17040
cacgggtgtt gctgttgttt gtggggcgtc ctgcactgtc gcataaccac aggatttcgc   17100
tgcactcgtc tagcgtgtcc tggtcgatag cgagatcgtc gaggctgact tcgttgacgg   17160
taaggttcac gttgtcgagg gagatgggta caccgtactg gttttcgaca ctgtcaacaa   17220
tgttttccag ctgttgcatg ttggtgggct gttgttggac gatacggtgt atcgctgtgt   17280
tgagggtggt gtaggtgata ttgtgtgtgt tgttcatggt tttatccaat ccctgtgctt   17340
tcgtcgtttt cgtctggata gtatctactg tttgcgtagc ctgttagggt gatcagtgtt   17400
tggtctgccc actgttttcac ggtttgtctt gtcactccga gtcgttgggc ggctgtggcg   17460
taggtttggt cataccgta tacttccctg aaggctgcga gcctggctag ccgttttcgc   17520
tgtttggatg gctggcaggt gagggtgtag tcgtcgatgg ctagctgcaa atcgatcatg   17580
gagacgatgt tgttgccgtg gtgttgtggc gcggttggtg gtggtggcat gcctggttcg   17640
acactcggtt tccatgggcc tccgttccag atccattggg cggcttggat gatgtcggcg   17700
```

```
gtggtgtagg ttcggttcac tggtaatcct taaacaagtc gttcatgttg ctggtgttgg   17760
tggtgtcgaa tcgtccgacg cagtggcagt agtcgtacat gagtttaata atgtgttggt   17820
ggtcgccgag gtaggtgttg ccgctgatac tgtaggtggc tgtgccgtct ttgctgatgg   17880
tgtatttggc ggtgatggtt tcgggtgttt cggtgttggt gatgatggct gtggtggtgg   17940
cgcctacggt ttgtagtctg gtggtttggg tgccgtcgtc gaggatggtg gtgaccatta   18000
tgattctcct tagttgctgg tttggttgtc ggctatggct gtgatttctt gtaccggttt   18060
gggtagatct aaatgctgtg tggttttgtt tgctagtcgt tgggctacac ggtagcccat   18120
ttgggtccac tggttgcctt ccagctggtg gtattggttg cgtacggcta tgtagaggag   18180
tgcgtcttga tagaggtcgt cggggttgat ggccgggtag tggcgcgcaa tgttggtgca   18240
ggctttgtgt agctggtgtt ggtggtgtgg ggttgcccat tcccagttgg cggtggtggc   18300
ttgttctact ttggttggtc gtctgctcat ggcactatta cctggctatc tggtagttgt   18360
tgggtgtttt gttgttgata gtgtagcaca cgagtccggg gtggccggtg gtgcctgtgc   18420
ggtgccggta ccagacggat tctccttcca tggatgggca ttggatgaag gtgcgttgtc   18480
cttgctctga gatttcgagg tggtgccggt gccctgccat gagaatatta gatacggtgc   18540 cgttgtgaa ttcttggccg cgccaccatt cgtagtgttg gttgttgcgc cattggtgtc   18600
cgtgggcgtg caggatagta gccccggcta cgtttacggt ggtggtcatt tcgtccctgt   18660
cagggaagtg gaagtgtagg ttggggtagt ggttggtgag ttggtaggct tctgcgatgg   18720
cgcggcagca gtccacgtcg aaggagtcgt cgtaggtggt gacgcctttg ccgaagcgca   18780
cggcttcacc gtggttgccg gggatggatg tgatggtcac atttttgcag tggtcgaaca   18840
tgtggacgag ttgcatcatg gccatgcggg tgagcctgat tgttccgtc aagggtgttt   18900 gtgtgcgcca ggcgttgttg ccgccttgtg acacgtatcc ttcgatcatg tcgccgagga   18960
atgcgatgtg gactcgttgc ggtttgcctg cttgctgcca gtagtgtttg gcggctgtga   19020
gggagcgtaa atagtcgtcg gcgaagtgtg atgtttcccc gccggggatg cctttgccga   19080
tttgaaagtc tcccgcccct accacgaacg caacattgct gtagtcggtg tgtgtgtctt   19140
ggttgggttt gggggggtgtc cattcggcta gtttatcgac gagttcgtcg accggatagg   19200
ggtcggttgc gggttggtgg tcgatgattt tttgtatgga tcggcctgtt tctccgttgg   19260
ggagtgtcca ttcggagatg cgtgtgcgcc gtacagtacc attggctaga ttgtcgtcga   19320
tggtgtcgat ggcgttgtcg tggttggcta gttgtgtgag gagccggtct atattgtcta   19380
tcatcggata tcctcttcct tttgcggggt ggtgttggct tgtttgcggc ggtagtcttt   19440
tataacggtg gcggagatgg ggtatcctgc ctgggtgagc tgttttgcta gccatgaggc   19500
ggggatggtt ttgtcggcga gcacgtctgc agccttgttg ccgtagcgtt gaataagggt   19560
ttcagttttg gttgccatga tgtcccatcg gttgtgtggt gggctgccat cctgtgcggc   19620
agtcgccgtc gtgtcctggt ttgcgggtgc accacgatac ggttccgtct gtgtggttga   19680
gtgttttgcc gcacatgacg tcacgtaggt gctcgggaaa ctcatcgttg ttgttgtccc   19740
cgtgcatgtc gatcaagtgt tgggttttag taaccatcat gcctcctatg tgtgaaagag   19800
tgtgcaaata ctatgcaggt gtcatggatg tttatgcggg tatggttttc atcaccttgc   19860
tgaacgttac ttggttactg tacatcatct gagtgatttc ctgatcagtc ttatcggggt   19920
gctgctttcg caggtcgcc cactggcagg cgttttcggt ctcctgctgt aaacgtgtca   19980
ggtgctgctc gttgatgatg tgtttccaca ttgtccatga cacgtcgagc ctgcggagca   20040
tgttcatggc tggcacgttg aaggaattga ggaagagtat ttcttcggtg tagtactgtt   20100
```

```
tttcgtattg gtcccatccg cttcggtgcc tgttgggctg gtttttgggg taggcttccc   20160
ggcagatttt gtgtaaccgt ttggccatgt cgtcgggtag tttaatgtcg ggttggcgc    20220 ggatcatgga tcgcatcccg tcataggtgg tgccccaggt gtgcatgata tgcagtgggt   20280
cttcaccgtc tgcccatttt tctgcacaga tggcgaggcg gatacgcctc ctggctgttt   20340
ggctggtgtt gcgccggttg gggatggggc acgtgtcgag gggatccatg atgttttggt   20400
gtacctttct ggtttcgtgt tgttgacgtg ttttactgta gcacagtgtc tagtgcttgt   20460
gtcaaccctg ttttccggc ctgcaggtag gtgtctgtga catcccccag ggtgaggggc    20520
acatgggtgg cttgcggtaa tgcttgggtt agggtttggg ccatctggtc gcctgcgggg   20580
tctgggtctg accagatgta gatgtggtcg tagccttcga aaaatttggt ccaaaagttt   20640
tgccacgagg ttgcgccggg tatggctacg gctggccatc cgcattgttc gaggatcatg   20700
gagtcgaatt cgccttcgca aatgtgcatt tcggctgccg ggttggccat ggcggccatg   20760
ttgtagatgg agcctgtgtc tcctgccggg gttaagtatt tggggtggtt gtgggttttg   20820
cagtcgtgtg ggagtgagca gcggaaacgc attttcgta tttcggctgg ccgcccccaa    20880
actgggtaca tgtatgggat ggtgatgcac tggttgtagt tttcgtggcc tggtatgggg   20940
tcattgttga tgtatccaag gtggtggtag cgggctgttt cttcgctgat gcctcttgcc   21000
gagaggaggt cgagtatgtt ttcgaggtgg gtttcgtagc gggctgaggc tttctggatt   21060
cggcggcgtt ccgcaatgtt gtatgggcgt atgctgtcgt acattcgggt tttctttctc   21120
taattgttgt tgtagcttgg cgagtccgcc tccgataccg catgtgtggc agtaccagac   21180
gcccttgtcg aggttgatgc tcatggaggg ctggtggtcg tcgtggaacg gacagaggat   21240
gtgttgctcg ttttttggatg ggttgtagcg tatctggtgg gtgtcgagga ggcggcgggt   21300
gtcagaggtg tgggaggagc tcgttgaggg ttgataccac ataggcttcg ctccagggtt   21360
tgttgcgttg tttcatgatg acgagtccga tggtggaatt gttttgtttg tttcggtgtg   21420
tttcgtagtt gcgtgcctcc cggctggctt gtttcacgaa ttcggcgagg tgtggctggc   21480
cggctttggc ttcgatcaca taggttttgt tgccggttgt gaggataagg tcgccttcgt   21540
cttcacggcc gttgaggtgg aggcgttcta tatcatggcc ggtgtcgcgt agttggtgga   21600
ggagtcgtgt ttcccattct gcgccggccc tgcggtttct tgattgttgt gtcgacatga   21660
tagtcctttg tgtgttgtgg tcatattcca gggctgtttt tcggcgaggg gcccgaagaa   21720
ggtgtattcg ggataggctc gtagccgctc gtatcgggtg ccgtcggggc tggatttgcc   21780
tgtgcgctgt ttgaggacgg cgatgcgtgc ctctgccggg atcgatagcc cgttgccgtt   21840
atcctcgcca ccatacaacg agactccgag gatgagttgt ggttttcgg agaggccgtt    21900 tttgatttct cgccgggcgg gcgggtgttc gatgtcggag ccggttttgt cggttgcgtg   21960
gtgtgtgaca ataatggtgg agccagtatc gcggccgagg gctgtgatcc attgcatggc   22020
ttcttgctgg gcctgatagt cactctcgca gtcttggatg tccatcaggt tgtcgataac   22080
gatgatgggt gggaaggtgt tccacatttc catgtaggct tgcagttcca tggtgatgtc   22140
tgtccatgtg atgggtgact ggaatgagaa tgtgatgtgt tggccgtggt ggatgctgtc   22200
tcgatagtat tctggcccgt agtcgtcgat gttttgttgt atctgggcgg tggtgtgttg   22260
ggtgttgagt gagatgattc gtgtggaggc ctcccagggt gtcatgtccc ctgatatgta   22320
gagggctggc tggttgagca tcgctgtgat gaacatggct agccctgatt tttgctgcc    22380 ggaccgcccc gcgatcatga cgagatcccc tttgtggatg tgcatatcct ggttgcggta   22440
```

```
gaggggttct agttgtggta tgcggggcag ctcggctgcg gtttgggagg ccctctcgaa    22500
ggatcgttgg agagagagca tcgggacctt atctatctat cggttacgat ttgtatgaat    22560
attggcggtt agatggagtc gatgtctaca tcatcactac cagtggtgtt gggctgactg    22620
tctcgctggt caacgtaggc tgctacaagg tcgtagatgg cgtcgtccaa tggttttgagc   22680 acgaccgcgt tgaagccgtt tttggtgcgc acggtggcga gtttgaaggc ttgctcttcg    22740
ccaaggtagg tttcgaggtc gcggatcatg gagtgtgggc ggtcgttgct gccgcgtact    22800 tttcgatga tggcgttggg gatggtttct ggggtgctgt tgttgaggtc gtctagggtg     22860
tggaagatgg tgacatcagc gtagatgcga tcggcggtct gtccaccgta gccttcagtg    22920
ttgtgctcga cgtcgtggac tttgaaggcg atggcggtgg cgtcctggtt tcgggagggg    22980
ttgaagaagg tgctgttgct gttgtttcgg tagtttgcga gtcccattgt tgtttccttt    23040
actgttttgt tgatttgtgt cggttttat cgggtgaggc tgtttcgttt gctgcggaac     23100
gcctcggata cgtcagtgtt gctggtgatg atcttcttgt actgtttcag aaggtcggct    23160
agctgtgctt tgcttgttgc attgttgatt ttgtcaatga tggtgttgtt tccttcactg    23220
gcaatgttgt ctacgtagtc tttggcggcc tggttgtatc ggtcttggag gatgatggat    23280
gcggaggcga tcagtgttgc caggtcccag ttccttgccg ccgagctgtt tttgagtccg    23340
cctagcaggt cgatgatagt cttctttact tcgtcggcgg tgtctccacg gatgactgtc    23400
catggggcgg cgtagtctcc gccgtatttg agtgtgatgg tgatgcgatc atcagtgctg    23460
ttggtgttat cgttcactgg tgctccttgc tttcttctgt tggggctgtg atggtggttt    23520 ctgtaggta cctgtaggcg tctttcccgt tgacggccca gcaggcgtcc ttgacggggc     23580
atcctttgca gagtgctgtg acgtggggta cgaagatgcc ttgactgatt cctttcattg    23640
cttgactgta catggatgat acatgctggt aggtgttgtt gtcaaggtcg tacagttcgg    23700
tggatgtgcc ttgtgtcggg gacttgtcgt cgttgcggct ggtggctggc gtccaaaaca    23760
tgccttttgt cacatcgttg ccgtgttggg cgagcatgta ccggtatgtg tgcagctgca    23820
tgctgtctgc tggtaggcgt ccggttttga ggtcgaggat gaaggtttcg ccggtgtcgg    23880
tgtcggtgaa aacgcggtcg atgtagccga cgatttgggt gccgtcgggg agggtggttt    23940
cgactgggta ttcgatgccg ggctggccgt ctaggactgc tgtgtggtat tgtggattgt    24000
ttgtgcgcca gttttttccac cggttgacga aggtttggcc gtagagcatc caccagtcgt    24060 agtcttttt gtgtggcccg cccgactcgc acatgttttt gcatattctg ccggagggtt     24120
tgatttctgt gccttcggat tcggcgaggg ctacttgggt gtcgaaaatg tttttgaagg    24180
atgagagttt gtctggcagt gcagggtatt cggcggggtt gtacaggtgt aggtcgtatt    24240
gttcggtgat gtggtgtatg cgcttccgg cgatggtggc gtaccaggtg tgatatgtgg     24300 cttttgtatcc gtgttggagg cgccatttt cgccgcattc ggcccactgt gacagtgatg    24360
agtaggagat gtggcctgga tggttgatgg ttttcgggta ttgtgctaga ggcattactt    24420
gtcgcttttg ttccatgggt tgcgggtgtc ctggccggcg tggtgttgct gataggcgag    24480
gagtgcgagg cagtgccagg cggcgtgtgc caggtggggt agccctgatt catcgtcgag    24540
gttgtgtcct tgctgccagg ctagcaggtg cctatagagg gcgtcgacac tgtggctcca    24600
cgggtatcct ccggtccagt tgttgtcgcc gtatttggtg gcaccgtagc ctgcaacctc    24660
gccgagagcg tgcaaggctg cggggtcgat gagggagagc ctgcagagtt tcaattcttt    24720
tttggcaccg ctgttgggt cggtgtacat gcggttggc ttatccatgg ggtgtgtgct     24780
ccttgggggt gggttactgg ttgttgttgt gggctagggc gacggcgaga ataatgatgg    24840
```

```
cgagggtttc agcgatgagg attggtgttg tgatcatttg ttgttttggg gctggtaggt    24900
gagtgtggag gcacccagga gggtggtgag ggcgcatgcg gcgatgatgg cgagggctgc    24960
cttgtgtggg gtgccggttg cgtacatcca tgtgatgatg gcgccttgga tccatgccag    25020
tgtggtgaag aacgtttcgt agctgtgtag ctcaatgttg ttgggtgtgt tcatgcttgc    25080
tcctggatga tggtgttgat ggttttgtag atgttgtaca ggtcggtttc gatggtttgt    25140
agctgtttga tttggtggtc gagatcaatg tttgggttga gggtgttgat gcggatgcg    25200 atgtcggtgg ctgtgcggag tgtgccgccg gtgtggtgaa tgatgtgtgc cgtgtcggcg    25260
agtccggtgg tgacagcgta gtgggagagg agaggcatag cggtccttgg cgggttagtg    25320
ttgcgggttg atgttgaggt cggtgacgtg gggtgtgttt tctgttccgg tgacgaggca    25380
gtggacggtg acgggtagtt tggatgctcc gggctggcgg acggtggcgc cgtagacgat    25440
agtaaaggtg tctttgtggg cgcctatgac tttgtggagt tggaggtcga tgtcggggtt    25500
gccgttccag ttgacaccgt gtgcggcggc ttgttgttcg gctttgcggt tgcaggtgtg    25560
tgcggcggtg atcatggtga gaccttgtga ggtttcttca ccgcgtgttt gggcttgccg    25620
gtgggctttc tgctgttcgg ctcgcagtga ctgttctgcg gcggcttgcc gggctttctt    25680
ttcggctttg cgctgttgga cggttttggg tgtccattcg gtgttggctg tggtggcctg    25740
tggggctggc tgtgaggcga gtggcggatt gtcgccgggg gctggcatga atgaggcggc    25800
ggcaatgatg gcggctgtga tgccggcgat ggtgtagcct gttttcttgt tcatgttttg    25860
tgtccccttt ccggggtgtt gttcgttgct gacatggtta atactttcag cgactgggcc    25920
cactgtcaag gctacgctca acgattgtga gcgattcgtg tgtggctagg ggttttatcg    25980
gctgtacagg gtgagtagat ggccaacgtt gatgcgggtc acatgccagt agagttgtgt    26040
ggcttcctca ctggtgagtg gcttccactc gttgtggctg aatacggtgc catcagtggc    26100
gataaacgtg ttggggcgta gcttgtggag ttcggcttcc acactctgtc ggtaggcttc    26160
ggcgaggccc tcaaaatcca tgtggtcgca ggagaggttt tcgaggcgtg tcaggtcgaa    26220
gggtgtgggg cagtcgtagc tggcggggt gtagagctgg gtgaagtggt tggcgatctt    26280
ctgcatcatg attcctttc tggtgatggt gtgttgatgg ttttatcggg tggatgcgac    26340
caggatggcg tctacatcga tcatgtcgat catgtcgtgg agttcctcgg cctcattctc    26400
ggataggtgg cgccagtcac agtctccgta tacggcgccg tcgagggtga cagtccacaa    26460
tggccggatg agccgtatgg cttcttgtac tttagcgtgg tacatgcgac gcaccatatc    26520
gagatcgatg tcgtctgaat ggtttccggt gaggctgtgg aggctgaggg ggtcgatttc    26580
tgtctgcctg tagagggatg tgaaggatgg tgtgacgagc gtgccatcca tagggtgtgt    26640 gctccttcg gtggtgtagg ggttgttgtg gtttctagag tgtgcgggct gttaccccac    26700
tgtcaaggct acgctcattt ggattgagcg tttcatgggg gtgtgtcggg tgtgacagat    26760
gtcacttaag cctttattga ctctcccagc gtctcaaatc ttctgggggt aggattatgc    26820
agggttggcc ctggtagtcg attctaggga ccttctaggg cgtctcaggg gtatgtctga    26880
gtgatagcag gtctggtaga tgacccggca gatctacctt gattttcatg gcaggagtcg    26940
aggtgccata tatgggcata gaatctaaac cctcatactg tgtgagatgt atcacactcg    27000
cctagtatgg tgtgcactct cgggatcact ctgccgatct ggcgtggagg gtgtagccaa    27060
gaaatgccgt ttaaagcctt cgcatggcgc ctaggagcgc cttgcggggt gggggctagg    27120
tatttatacc cccagcatat tctgatcgat tctagacgta cccaaaagcc tgatatacga    27180
```

```
tcaaccatct cagcatagac catcagcccc tatcctggtt agctaagcct acactatgtg    27240
gacagtgtgg gataccgtgg gggaagaagg acacggtaaa agaaagaggg gggagcatca    27300
gccttcccac ctgaggtact tcagttcacc ttaaggtctt agcacttagc accgagcccc    27360
tcaaaggctc ggcatcagcc cgaacaggct cagccctgaa aggggtacac gtcatcagag    27420
aaggcttgag agtacgagga gccctagcga cgagtactcg aaagcctgag ggaacaccct    27480
cagcactgat gggcctagcg tgttcggaaa ggacacaaga gtacagtgtg acagctatcc    27540
gggagtgaaa cccgttctga ctaggggttt cagccttaac caccctcaaa ggttacaaga    27600
ctttaagaaa atttaaggaa aagtttaggt ttaattttg gaccttacc accaaaaaca    27660
cccgtttaca cccctcaaac ccgcctatag agccaaatcc accagtttga ctcatcccag    27720
gtggggtatg ataggctgga caggtagcca gctggacgca aggccgaaat ccgctgacgc    27780
ggctttcacc cttacatcca tcagtctacc aaagacttaa agacctaagg gcttagcgct    27840
aaggtgctga tagcttagca ccgagcccct caagggctcg gcatcagtct taaagcctta    27900
aacacttcaa gtacatataa aactttaaga gcttaacact taaggttatc aataaacatt    27960
aaagctttaa agtcttaaag tacatataaa accttaacag ttaaacgtta aaagctttaa    28020
accttaacac ctaagttaag tataaaacct taaggatta gcacttaagg atataaactt    28080
aacatcagtg tttaagactt taaaacttaa aataactatt aagacttaaa gacctataag    28140
ctttaaacac ttaaagtaac tataagactt taaaaacctt aagtacttaa agttaaccat    28200
cagtcttaaa ctttactatt atacctataa gtcttaaagc ttataggtat aataatataa    28260
tataagtatt aaagcttata agttataaaa gttttagaag agctaagggg ttaacttctt    28320
tacttctctt ctctctttgg ttctttctct cttctcttct tttcttcatc aggggagaag    28380
aggaaccttt taccgtcaac gctgatgggc ttttcgccgt gtgtctcgtg taccaccggt    28440
cgcacgctcc cggtttgtac actccccaca ctctgacacc cgtgtccctt tcaggtttgg    28500
cgtgttcggc tgaaggcgta cggcgtgtca cgccaacacc cttaacacca ggtaagactt    28560
aaagtgcata ttatatgtag aagactttaa aaacctgtca ggtgttcctg ctgagcctgt    28620
gtcctacacc gctaggcgcc aagcgctaag ctgtgaaacg cgaacacaca ctcacccect    28680
ttttctttcg tgtccttctc ttttgacaca gctgggggc gatgtgatct ttttcacacc    28740
cgttgggggt agtggagaaa acaaccaccc cggcacaaac agaacacccc ctcaaacgaa    28800
caaaacaggg cctagaatcg atcggcaggg caccggtaga gtattcatac ccccaacggt    28860
tcccaagccg ttacaggagc aatgagaggc tcacagggc cataggagat caggggacgc    28920
gatggcacac accaaccgca cagccagcca agcccaccgg cgctggcggg caagactcat    28980
cacccaagcc cgacagcaag gccaaaccga atgcccactc tgcggagcca ccatcgcctg    29040
ggacacacac gacctgccaa ccagccccga agccgaccac atcacgcccg tcagcagggg    29100
aggactcaac accctcgaca acgggcaaat catctgcaga acatgcaaca gaagcaaagg    29160
caatcgcagc gaaccaaaca tcaaactcca acaacaaacc acaaaaacat tgattccatg    29220
gtgaaaaacc cgccaacccc caccgtggac accccctgca caggcggcaa gacct         29275
```

<210> SEQ ID NO 4
<211> LENGTH: 29153
<212> TYPE: DNA
<213> ORGANISM: Bacteriophage 103672

<400> SEQUENCE: 4

```
tcccttttgt ggattgtctg tttgtcgact ttttgtgttg gtggtgagtg ttgtgcagcc       60
```

```
tgagcttcct gatagtcgtg gatggtgtgg ggagacgcgt cgttggtggc gtgtgtgggg    120
tgaggatccg cgtgccgggt ttgtgtctga tgaggagtgg ctgtttctca tggatgctgc    180
ggtgattcat gattgtgtgt ggcgtgaggg tcgcgcggat ttggtggctt cgcttcgtgc    240
tcatgtgaag gcttttatgg gtatgttgga tcggtattcg gttgatgtgg cgtctggtgg    300
ccgtggtggg ggttctgcgg tggcgatgat tgatcggtat aggaagcgta ggggtgcttg    360
atgtctcggg tggtgggttc tcaggttcct cgtcaccgtg tggctgcggc gtattcggtg    420
tctgctggcg gtgatgctgg ggagttgggt cgtgcgtatg ggttgacgcc tgatccgtgg    480
cagcagcagg tgttggatga ttggctggct gtcggtggta atggcaggct tgcttcgggt    540
gtgtgtgggg tgtttgtgcc tcgccagaat ggcaagaatg ctattttgga gattgtggag    600
ttgtttaagg cgactattca gggtcgccgt attttgcata cggctcacga gttgaagtcg    660
gctcgtaagg cgtttatgcg gttgaggtcg ttttttgaga atgagcggca gtttcctgac    720
ttgtatcgta tggtgaagtc gattcgggcg acgaatggtc aggaggctat tgtgttgcat    780
catccggatt gtgccacgtt tgagaagaag tgtggctgca gcggttgggg ttcggtggag    840
tttgtggccc gttctcgggg ttctgctcgc gggtttacgg ttgatgattt ggtgtgtgat    900
gaggctcagg agttgtcgga tgagcagttg gaggctttgc ttcctacggt gagtgctgcc    960
ccgtctggtg atcctcagca gattttctt ggcacgccgc ctggtccgtt ggctgatggt    1020
tctgtggtgt tgcgtttgcg tgggcaggct ttgtcgggtg gtaaaaggtt tgcgtggacg    1080
gagttttcga ttcctgacga gtctgatccg gatgatgtgt cgcggcagtg gcggaagttg    1140
gctggggaga cgaatccggc gttggggcgg cgtttgaatt ttgggactgt gtcggatgag    1200
catgagtcga tgtctgctgc cgggtttgct cgggagcggc ttggctggtg ggatcgtggc    1260
cagtctgctt cgtctgtgat tcctgcggat aagtgggctc agtctgcggt ggatgaggcg    1320
gctctggttg gcgggaaagt gtttggtgtc tcgttttctc gttctgggga tcgggttgct    1380
ttggcgggtg ccggtaaaac tgatgctggg gttcatgttg aggttattga tgggctgtcg    1440
ggaacgattg ttgatggtgt gggccggttg gctgactggt tggcggttcg ttggggtgat    1500
actgaccgga ttatggttgc cgggtctggt gcggtgttgt tgcagaaggc gttgacggat    1560
cgtggtgttc cgggccgtgg cgtggtggtt gccgatactg gggtgtatgt ggaggcttgt    1620
caggcgtttt tggagggtgt caggtcgggt gtgatcagtc atcctcgtgt tgattctcgc    1680
cgtgacatgt tggagattgc tgtgaggtcg gctgttcaga agcgtaaggg gtctgcgtgg    1740 ggttgggggtt cctcgtttaa ggatggttct gaggttcctt tggaggctgt atcgttggcg    1800
ttttttgggg ctaaacgtgt tcgtcgtggc cgtcgggagc gtagtggtag aagcgggtg    1860 tctgtggtat gaactcggat gagttggctt tgattgaggg tatgtacgat cgtatccaaa    1920
ggttgtcttc gtggcattgt tgcattgagg gctactatga gggctctaat cgggtgcgtg    1980
atttgggggt ggctattcct ccggagttgc agcgtgtgca gactgtggtg tcgtggcctg    2040
ggattgcggt ggatgctttg gaggagcgtc tggattggct tggctggact aatggtgacg    2100
gctacggttt ggatggtgtg tatgctgcga atcggcttgc tacggcgtcg tgtgatgtgc    2160
atttggatgc gctgattttt gggttgtcgt ttgtggctgt tatcccccag ggggatgggt    2220
cggtgttggt tcgtccgcag tcgccgaaga attgtactgg ccggttttcg gctgacgggt    2280
ctcgtttgga tgctggtctt gtggtgcagc agacgtgtga tcctgaggtt gttgaggcgg    2340
agttgttgct gcctgatgtg attgttcagg tggagcggcg tgggtctcgt gagtgggttg    2400
```

```
agacgggccg tatcgtgaat agtcttggtg cggttccgtt ggtgccgatt gtgaatcggc   2460
gtaggacgtc gcgtattgat ggccgttcgg agatcactcg gtctattagg gcttacacgg   2520
atgaggctgt gcgcacactg ttggggcagt ctgtgaatcg tgacttctac gcttatcctc   2580
agcgttgggt gactggtgtg agcgcggatg agttttcgca gcctggctgg gtcttgtcga   2640
tggcttctgt gtgggctgtg gataaggatg atgatggtga taccccgaat gtgggtcgt    2700 ttcctgtcaa ttcgcctaca ccgtattcgg atcagatgag actgttggcg cagttgacgg   2760
cgggtgaggc tgcggttccg gaacgctatt tcgggtttat cacgtctaac ccgcctagtg   2820
ggaggctttt ggctgccgag gagtctcggc ttgtgaagcg tgctgaacgc aggcagacgt   2880
cgtttggtca gggctggctg tcggttggtt tcctggctgc taaggcgttg gattctcgtg   2940
ttgatgaggc cgattttttt ggtgatgtgg gtttgcgttg gcgtgacgct tcaacgccga   3000
ctcgggcggc tacggctgat gctgtgacga agcttgttgg tgccggtatt ttgcctgctg   3060
attctcgtac ggtgttggag atgttggggc ttgatgatgt gcaggttgag gctgtgatgc   3120
gtcatcgtgc cgaatcttcg gatccgttgg cggcgctggc tggggctatt tctcgtcaaa   3180
ctaacgaggt ttgatgaatg gcttcgggtg ctatgtcgag gcttgctgcg actgagtatc   3240
agcgtgaggc ggtcaggttt gctgggaagt atgcgggcta ttattctgag cttggtcgtt   3300
tgtggcattc cgggaagatg acagatgcgc agtatgtgcg tttgtgtgtg gagttggagc   3360
gtgccggcca tgatggttcg gcatcgttgg ctgccaggtt tgtgcaagat tttcgccggt   3420
tgaacggtgt cgatcctggt ttgattgtgt atgacgagtt tgatgctgcg gcggcgttag   3480
ctcggtcgtt ttcgactatg aagattcttg agagtgaccc ggataggtg aatgacacga    3540 ttggtgcgat ggctgcgggt gttaatcggg ctgtcatgaa tgctggccgt gacacggttg   3600
agtggtcggc gggtgcgcag ggtaggtcgt ggcgtcgggt tactgatggt gatccgtgcg   3660
cgttttgtgc catgttggct acgaggtcgg attatacgac tcgggagcgg gcgcttacta   3720
cgggtcatac tcggcgtcat aagcgtgccg gtaagcgtcc gcttggttcg aagtatcatg   3780
atcattgtgg gtgtacggtg gttgaggttg ttggtccttg ggaaccgaat agggctgatg   3840
ccgcatatca gaggacgtat gagaaggctc gtgagtgggt tgatgatcat gggttgcagc   3900
agtcgcctgg caatatttg aaggctatgc gtactgttgg cgacatgaga tgatggtttc    3960
cggttgtgtg ccgccggtta tcggtgcaca gggttgtctc ccgcacgggg gtcaacaatg   4020
ttgtgttgtt ttccgcaagg agtatagggt taggctatgg ccgatcaaaa agttgaagaa   4080
cagaatgttg acaatgatgc tgttgagccc ggaaagggtg gagatgttgt tgatgttgtg   4140
aaggatgggc aggctgccgg cgatgatcat gccggtgatg tttccgtgaa ggaggagtct   4200
tcttctggca cggattggaa ggctgaggcc cgtaagtggg agtctcgtgc taaaagtaat   4260
ttcgccgagt tggagaagct tcgcgcctcg gatggtgatg cggggtctgt gattgatgag   4320
cttcgccgca agaatgagga actcgaagac cggatcaacg ggtttgttct tgagggtgtg   4380
aagcgcgagg tggcttcagg gtatggtttg tccagtgatg cgatcgcttt cttgtcgggt   4440
ggcgataagg agtcgcttgc cgagtctgcg aaagctttga agggtttgat cgaccatagt   4500
agtggtggcg tgggtgtgcg ccgtcttgcg gggagtgccc ccgttgatga tgttaaacga   4560
cgtgagggtg tcgcgtttgt ggatgctctt gtcaataatt ctaggagatg atttgtgatg   4620
gctgacgatt ttcttctgc agggaagctt gagcttcctg gttctatgat tggtgcggtt    4680
cgtgaccgtg ctatcgattc tggtgttttg gcgaagcttt cgccggagca gccgactatt   4740
ttcggtcctg ttaagggtgc cgtgtttagc ggtgttcctc gcgctaagat tgttggtgag   4800
```

```
ggcgaggtta agccttccgc gtctgttgat gtttcggcgt ttactgcgca gcctatcaag    4860
gttgtgactc agcagcgtgt ctcggacgag tttatgtggg ctgacgccga ttaccgcctg    4920
ggtgttttgc aggatctgat ttccccggct cttggtgctt cgattggtcg cgccgtggat    4980
ctgattgctt tccacggtat tgatccggct acgggtaagc ctgctgcggc tgtcaagtct    5040
tcgctggata agacgaagca tattgttgat gcaaccgata gcgctacggc tgatctgatt    5100
aaggctgttg ggctgattgc tggtgccggt ttgcaggttc ctaacggggt tgctttggat    5160
ccggcgttct cgtttgccct gtctactgag gtgtatccga aggggtctcc gcttgccggc    5220
cagcctatgt atcctgccgc cgggttcgcc ggtttggata ttggcgtgg cttgaatgtt    5280 ggtgcttctt cgactgtttc gggtgtcccg agatgtcgc ctgcctctgg tgttaaggct    5340
attgttggtg atttctcgcg tgttcattgg ggtttccagc gtaacttccc gatcgaactg    5400
atcgagtatg gtgacccgga tcagacgggg cgtgacctta agggccataa tgaggttatg    5460
gttcgcgccg aggctgtcct gtatgtggct atcgagtcgc ttgactcgtt tgctattgtg    5520
aaggagaagg ctgccccgaa gcctaatccg ccggccgaga actgatctat tgttgctat    5580 aatgttcatg ctgtgtgcag ggggtggtat tgatgggtat cattttgaag cctgaggata    5640
ttgagccttt cgccgatatt cctagagaga agcttgaggc gatgattgcc gatgtggagg    5700
ctgtggctgt cagtgtcgcc ccctgtatcg ctaaaccgga tttcaaatac aaggatgccg    5760
ctaaggcgat ccttcgtcgg gctttgttgc gctggaatga taccggggtt tctggccagg    5820
tgcagtatga gtctgcgggt cctttcgctc agactacacg gtctaatact cccacgaatt    5880
tgttgtggcc ttctgagatt gccgcgttga agaagttgtg tgagggtgat ggtggggctg    5940
gtaaggcgtt cactattaca ccgaccatga ggagtagtgt gaatcattct gaggtgtgtt    6000
ccacggtgtg gggtgagggt tgctcgtgcg ggtcgaatat taacggctac gctggccctt    6060
tgtgggagat atgatatgac cagttttcct tatggtgaaa cggttgtgat gcttcagccg    6120
actgttcgtg tcgatgatct tggtgacaag gtggaagact ggtctaagcc tgtcgagact    6180
gtgttccata acgtggccat ctatgcttcg ttgtcgcagg aggatgaggc cgcggggcgt    6240
gactcggatt atgagcattg gtcgatgctt ttcaagcagt ctgttgtggg tgccggttat    6300
cgttgtaggt ggcgtattcg gggtgttgtg tgggaggctg acgggtctcc tatcgtgtgg    6360
catcacccca tgtctggctg ggatgcgggc acgcagatca atgtgaagcg taagaagggc    6420
tgatgggtag tggctcagga tgtgaatgtg aagctgaact tgccgggtat tcgtgaggtg    6480
ttgaagtctt ctggggtgca ggctatgttg gctgagcgtg gcgagcgtgt caagcgtgcg    6540
gcctcggcga atgtgggcgg taacgctttc gatagggccc aataccgtaa tggtttgtcg    6600
tcggaggtgc aggttcaccg tgttgaggct gtggcgagga ttggcactac ctataagggt    6660
gggaagcgta ttgaggcgaa gcatggcacg ttggcgaggt cgattggggc tgcgtcgtga    6720
tcgtttacgg tgatccgcgt gtgtgggcta aacgcgtgct caaggatgat ggctggctgt    6780
caggtgtgcc ttgtgtgggg acggtgcccg atgattttac gggtgacctg atttggttgg    6840
cgttggatgg tggcccgcag ttgcatgtgc gtgagcgtgt ttttttgcgc gtgaatgtgt    6900
tttcggatac gccggatcgt gctatgtcgt ggcgcgtcg tgttgaggct gtgctggctg    6960
atggtgtgga tggtgaccct gtggtgtatt gtaaacggtc tactggccct gatttgctgg    7020
ttgatggtgc acgttttgat gtgtattcgc tgttcgagct gatatgtagg cctgtcgaat    7080
ctgaataagc ttattgtttt tgtttaatg taattgtttg atatttaatg ggggttgtga    7140
```

```
tggctgcaac acgtaaagcg tctaatgttc gctctgctgt tacgggtgac gtttatattg   7200
gtgccgcgca cgcgggtgac actattgatg gtgtgaagac ggttcctgac ggtcttaccg   7260
ctttaggta cctgtctgat gacgggttta agattaagcc tgagcgtaaa acggatgatt    7320
tgaaggcttg gcagaatgcg gatgttgttc gcactgtggc tactgagtcg tctatagaga   7380
tttcttttcca gctgatcgag tctaagaagg aggttatcga gctgttttgg cagtcgaagg  7440
ttactgccgg atccgattcg ggttcgttcg atatttctcc gggtgccacg acgggcgtgc   7500
acgctttact gatggatatt gttgatggtg atcaggttat tcgctactat ttccctgagg   7560
ttgagttgat cgatcgtgac gagattaagg gtaagaatgg cgaggtttac gggtatggtg   7620
tgacgttgaa ggcgtatcct gcccagatta ataagaaggg tgatgcggtg tctggtcggg   7680
ggtggatgac ggctttaaaa gctgatactc ctccggttcc gccttctccg aagcctcagc   7740
cggatccgaa tccgccgtct aataactgat acacgagttt aagggattgt tgatagatga   7800
gtgacactgg tttcacgttg aagattggtg accgtagctg ggtgttggcg gatgcggagg   7860
agacggctca ggctgttcct gcccgcgtgt ttcgccgtgc cgccaggatt gcccagtcgg   7920
gggagtctgc ggatttcgcc caggttgagg tgatgttttc tatgctagaa gcggccgcct   7980
cggctgacgc ggtggaggct ttggaggggc ttcctatggt tcgtgttgcc gagattttcc   8040
gtcagtggat ggaatacaag cccgaccaga aagcagcctc cctgggggaa tagtttggct   8100
ccacggcctg attgatgatt atcgtggggc catcgaatac gatttccgca ctaaatttgg   8160
tgtttctgtt tatagtgttg gtggcccgca gatgtgttgg ggtgaggctg tccggctggc   8220
tggcgtgttg tgtaccgata cgtctagcca gttggcggcc cacctgaatg gttggcagcg   8280
cccgtttgag tggtgcgagt gggctgtgtt ggacatgctg gatcattaca ggtctgctaa   8340
tagtgagggg cagccggagc ctgtggcgag gcctacggat gagcgtaggg cccggtttac   8400
gtcggggcag gtggacgata ttttggcgcg tgttcgtgcc ggtggcgggg tgtctcgcga   8460
gattaatatt atggggtgaa tagtgtatgt ctggtgagat tgcttccgca tatgtgtctt   8520
tgtatacgaa gatgccgggt ttgaaagcgg atgttggtaa acagctttcc ggggtgatgc   8580
ctgcggaggg tcagcgttcg ggtagcttgt ttgctaaggg catgaagttg gcgcttggtg   8640
gtgccgcaat ggtgggtgct atcaatgttg ctaagaaggg cctcaagtct atctatgatg   8700
tgactattgg tggcggtata gcgagggcta tggctattga tgaggctcag gctaaactta   8760
ctggtttggg tcacacgtct tctgacacgt cttcgattat gaattcggct attgaggctg   8820
tgactggtac gtcgtatgcg ttgggtgatg cggcttctac tgcggcggcg ttgtctgctt   8880
cgggtgtgaa gtctggcggg cagatgacgg atgtgttgaa gactgtcgcc gatgtgtctt   8940
atatttcggg taagtcgttt caggatacgg gcgctatttt tacgtcggtt atggcgcgcg   9000
gtaagttgca gggcgatgac atgttgcagc ttacgatggc gggtgttcct gtactgtctt   9060
tgcttgccag gcagacgggt aaaacgtcgg ctgaggtgtc gcagatggtg tcgaaggggc   9120
agattgattt tgccacgttt gcggctgcga tgaagcttgg catgggtggt gctgcgcagg   9180
cgtctggtaa gacgtttgag ggtgctatga agaatgttaa gggcgccctg ggttatcttg   9240
gtgctacggc tatggcgccg tttcttaacg gcctgcggca gattttgttt gcgttgaatc   9300
cggttatcaa gtctatcacg gattctgtga agccgatgtt tgctgccgtc gatgctggta   9360
ttcagcgtat gatgccgtct attttggcgt ggattaatcg tatgccgggc atgatcactc   9420
gaatgaatgc acagatgcgc gccaaggtgg agcagttgaa gggcattttt gcgagaatgc   9480
atttgcctgt tccgaaagtg aatttgggtg ccatgtttgc gggtggcacc gcagtgttcg   9540
```

-continued

```
gtattgttgc tgccggtgtg gggaagcttg tcgtagggtt tgccccgttg gcggtgtcgt    9600
tgaagaatct gttgccgtcg tttggtgctt gaagggtgc cgccgggggg cttggcggcg    9660
tgtttcgcgc cttgggtggc cctgtcggta ttgtgatcgg cttgtttgct gccatgtttg    9720
ctacgaacgc ccagttccgt gccgctgtta tgcagcttgt ggctgtggtt ggccaggcgt    9780
tggggcagat tatggccgct attcagccac tgttcgggat tattgctggc gtggttgcca    9840
ggttggcgcc agtgttcggc cagattatcg gtatggttgc tggtttggct gcccaactgg    9900
tgcctgttat tggtatgctt attgcccggc tggttcctgt tattacccag attattggta    9960
tggtaaccca ggttgctgcg atgattttgc ctatgctgat gccggttatt caggctgttg   10020
ttgctgtgat acggcaggtt gttggcgtga tcatgcagtt ggtgcctgtt ttgatgcctg   10080
tgattcagca gattttgggt gctgtcatgt ctgttttgcc gccgattgtt ggtttgatac   10140
ggtcgctgat accagtcatc atgtcgatta tgcgtgtggt ggtgcaggtt gtttcggttg   10200
tgttgcaggt ggtggcccgt attattccgg ttgttatgcc gatttatgtt gcggtgattg   10260
gattcattgg caagatttat gctgcggtta tcggttttga ggctaaggtt attggcgcta   10320
ttcttcgtac tattacgtgg attgtgaatc atttagtgtc tggcgtcagg tctatgggca   10380
cggccatcca gaatggctgg aatcatatca aatcgtttac gtcagcgttt attaacggtt   10440
tcaaatctgt tatttctggc ggcgtgaacg ctgttgtggg gtcttttgcc cggcttggtt   10500
cttcggttgc ctcccatgtg aggtctggtt ttaacgcggc ccggggtgct gtttcttctg   10560
cgatgaattc tatccggggt gttgtgtctt cggtggcgtc tgctgttggt gggttttca    10620
gttcgatggc gtctagggtt cgtagtggtg ctgtgcgcgg gtttaatggt gcccggagtg   10680
cggcttcttc tgctatgcat gctatgggg ccgctgtgtc tagcggggtg catggtgtgc    10740
tgggtttttt ccggaatttg cctggcaata ttcggcatgc tctcggtaat atgggtgtcac   10800
tgttggtgtc tgctggccgt gatgtggtgg ccggtttggg taacggtatt aagaatgcta   10860
tgagtggcct gttggatacg gtgcgtaaca tgggttccca ggttgctaat gcggcgaagt   10920
cggtgttggg tattcattcc ccgtctcggg tgtttcgtga ccaggttggc cggcaggttg   10980
ttgccggttt ggctgagggg atcaccggga atgcgggttt ggcgttggat gcgatgtcgg   11040
gtgtggctgg acggcttccg gatgctgttg atgcccggtt tggtatgcga tcgtctgtgg   11100
gctcgtttac accgtacgac cggtatcggc gtgcgagcga aagagtgtt gtggtgaatg    11160
tgaatgggcc tacttatggg gatcctgccg agtttgcgaa gcggattgag cggcagcagc   11220
gtgacgcttt gaacgcgttg gcttacgtgt gattgagggg gtgttgtgca tgtttattcc   11280
tgacccgtct gatcgttctg gtttgactgt gacgtggttt atggatccgc tgtttggcga   11340
cgagcgtgtg cttcatttga cggattatac gggtgcgtct cctgtcatgt tgttgaatga   11400
ttcgttgcgc ggtttgggtg ttcccgaggt tgagcatttt tctcaaacac atgttgggt    11460
gcacggctcg gagtggcgcg ggtttaatgt gaagcctcgc gaggtgacgc tgccggtttt   11520
ggtgtcgggt gttgacccgg atccggatgg cgggtttcgt gacggttttt tgaaagccta   11580
tgacgagttg tggtcggcgt ttccctcggg cgaggtgggg gagttgtcgg ttaaaacccc   11640
gtctggtcgt gagcgtgtgt tgaagtgccg gtttgattcg gtggatgaca cgtttacagt   11700
tgatccggtg aacagggct atgcgcgcta tctgttgcat ttgacagcgt atgacccgtt    11760
ttggtatggg gaggagcaga agtttcgttt tagtaacgcg aagttgcagg attggttggg   11820
tggcggccct gtcggcaagg atggcacggc gtttcctgtg gtgttgacgt ctggtgttgg   11880
```

```
ttctggctgg gataatctgt ctaataaggg tgatgtgcct gcgtggcctg ttattcgtgt    11940
tgaggggcct ttggagtcgt ggtctgtgca gattgatggt ttgcgtgtgt cttcggatta    12000
tcctgtcgag gagtttgatt ggatcactat tgatacggat cctcgtaaac agtctgcgtt    12060
gttgaacggg tttgaggatg tgatggatcg tttgacagag tgggagtttg ccctatccc    12120 gcctggcggt tcgaagagtg tgaatattga gatggttggt ttgggtgcca ttgttgtgtc    12180
ggtgcagtac aggttttga aggcttggtg aatagttgat gactgatctg gttccgcatg    12240
taacattgtt tacaccggat tatcgccgtg tggcgcctat caatttttt gagtcgttga    12300 agttgtcgtt gaagtggaat ggtttgtcga cgctggagtt ggtggtgtct ggtgatcatt    12360
ctaggcttga cggggttgact aggccgggtg cacggctggt tgttgattat ggtggtggcc    12420
agattttttc tgggcctgtg cgtcgggtgc atggtgtggg tccgtggcgt tcttcgcggg    12480
tgactatcac gtgtgaggat gatatccgcc tgttgtggcg tatgttgatg tggcctgtga    12540
attatcgtcc tggtatggtt ggtatggagt ggcgtgccga cagggattat gcccactatt    12600
cgggtgcggc ggagtcggtt gctaagcagg tgttggggga taatgcttgg cgttttccgc    12660
ctggtttgtt tatgaccgat gatgagagtc gtggccgcta tattaaggat tttcaggtgc    12720
ggtttcacgt gtttgccgat aagttgttgc cggtgttgtc gtgggctcgg atgactgtca    12780
cggtgaacca gtttgagaat gcgaagtttg atcagcgtgg tttggtgttt gattgtgtgc    12840
ctgctgtgac ccggaagcat gtgttgactg ccgagtctgg ttcgattgtg tcgtgggagt    12900
atgtgcgtga cgcccctaag gctacttcgg tggtggttgg tggccgcggc gagggtaagg    12960
atcggctgtt ttgtgaggat gttgattcga tggccgaggg ggattggttt gatcgtgtcg    13020
aggtgtttaa ggatgcccgt aacacggatt ctgaacatgt gcatctcatc gatgaggctg    13080
agcaggtgct gtccgagtcg ggggccacgt cggggtttaa gatcgagttg gctgagtcgg    13140
atgtgttgcg gtttgggccc ggcaatctga tgccgggtga tttgatttat gtggatgtgg    13200
gttctggccc tattgcggag attgttcggc agattgatgt ggagtgtgta tcgcctggtg    13260
acgggtggac gaaggtgact cctgttgctg gggattatga ggataatccg tcggccctgt    13320
tggctcgccg tgttgccggt ttggctgccg gtgtgcggga tttgcaaaag ttctaaaaag    13380
attaggggtt tgttgtgggt attgtgtgta aagggtttga tggtgtgttg accgagtatg    13440
attgggctca aatgtctggt ctgatgggta atatgccgtc tgtgaagggc ccggacgatt    13500
ttcgtgtcgg cacgacgatt cagggtgcca cagtgttgtg tgaggtgttg ccggggcagg    13560
cttgggctca cggggtgatg tgcacgtcga atagtgttga gacggtgacg ggccagcttc    13620
cgggccctgg tgagacccgc tacgactatg tggtgttgtc tcgggattgg gagcagaaca    13680
cggccaagtt ggagattgtt cccgggggc gtgcggagcg tgcccgggat gtgttgcgtg    13740
ccgagcctgg cgtgtttcat cagcagttgt tggctacttt ggtgttgtcg tctaacgggt    13800
tgcagcagca gctggatcgg cgtgctatag cggctagggt tgcgtttggg gagtctgctg    13860
cgtgtgatcc taccctgtg gagggtgacc gggtgatggt tccttcgggg gctgtgtggg    13920
ctaaccattc gggtgagtgg atgttgttgt cacccaggat agagacgggt tctaagtcga    13980
tcatgtttgg cgggtcggct gtgtatgctt acatgatccc gtttgagcgg ccgtttagta    14040
gtgcgcctgt tgtggtggcg tctatggcta cggcggctgg gggtacgcag cagatcgatg    14100
tgaaagccta caatattact aataaggatt ttagtttagc gtttattacg aatgatggtt    14160
ctaagccttc tggtgtgcct gcggtggcta actggattgc tgtgggcgtg tgaccgggct    14220
gttgttgtgg cggatggtgt gatgttgggg gggctgtggt gtcgtggttt actcctgcac    14280
```

```
tggtggcctc tatttgtacc gcgttggcca cgattttggg ttctgttcag gcggtcacat   14340
cccgttctag gcggcgtttg cggcggctgt cggctcaggt ggatgcgatg gaagagtata   14400
cgtggggtgt tcggcgtgag gttcgccggt ttaactcgcg gcttcctgac gaggtggagc   14460
ctatgcgtct tcctgatgtg cccgagtttt tgaaagatac tgttgatggt ggaggtgagt   14520
agggttgagg gagttggagg aggagaagcg gcagcgccgc tcgtttgaga aggcttccct   14580
gatactgttg ttcctgtcgc ttgtactgtt ggcggtggtt gccggggatg ctttacggta   14640
cgggtctgtg gcttcccaaa gggattcaga gcaggctaaa gcccagtcga atggtacagc   14700
cgctaaaggt ttggctgccc gtgtgaagca ggcgtgtgcc tctggcgggc aggagtctgt   14760
gcggcttcac cagtctggct tgtgtgtgga tgctgtgcgt gttgagcgga gtgtgcatgg   14820
tgtgccgggc ccgccggtg agcgcggccc gcaaggccct gcaggtgttg acggccggga   14880
tggtgttaat ggttcggctg ggctggttgg ccctgttggt ccgcagggtt ctcccggttt   14940
gaatggtgtg aagggtccgc agggttctgc cggtgcgaac ggatcggatg ccatgatgg   15000 tgttccaggt cgtgcaggtg ctgacggtgt gaacggcgct gatggtcgag atggtcctgc   15060
cggtaagcgc ggtgatgtgg gcccttcagg tccggccggc ccgcaaggtg cacagggtga   15120
acggggtcct attgggcctc agggtccgca gggttctgcc ggtgcgaacg gatcggatgg   15180
ccatgatggt aaagatgggc gttctgtggt gtctgtgtac tgttccgggg gccgcctggt   15240
tgtgaaatat agtgacggta tggtttctac catatcgggt tctgtggcct gtgagggtgt   15300
gaaaccgtcg cctatagtga ctatatcatc ccacaaatag aaaggagtgg ctgtgatggt   15360
agtgtttggt ggtggtgtgt ggtgaggttt attcctgctg cgcatcattc tgccggctcg   15420
aatagtccgg tgaatagggt tgtgattcat cgacatgcc cggatgtggg gtttccgtcc   15480
gcttcccgta aggggcgggc ggtgtctacg gcgaactatt tcgcgtcccc atcggcgggc   15540
ggttctgccc attatgtgtg cgatatttcg gagacggtgc agtgcttgtc ggagtctacg   15600
attgggtggc atgccccgcc gaatccgcat agtttgggta tcgagatttg cgcggatggg   15660
ggttcgcacg cctcgttccg tgtgccaggg catgcttaca cgagggagca gtggctggat   15720
cctagggtgt ggcctgcgt ggagaaggct gccatcctgt gtagacgttt gtgtgacaaa   15780
tataatgttc cgaaaaggaa gcttagtgca gccgatttga aggctggcag gcggggtgtt   15840
tgcgggcatg tggatgttac ggatgcgtgg catcagtcgg atcatgacga tcctgggccg   15900
tggtttccgt gggacaaatt tatggctgtg gtgaatggcc acggcggcgg ttcaagtagt   15960
gaggagttaa cggtggctga tgtgaaagcg ttacataatc agattaaaca attgtctgct   16020
cagcttactg gttcggtgaa taagctgcat cacgatgttg gtgtggttca ggtgcagaat   16080
ggtgacctgg cgccgcgtgt tgatgccttg tcgtgggtga agaatccggt gacggggaag   16140
ctgtggcgca ctaaggatgc cctgtggagt gtctggtatt acgtgctgga gtgtcgtagc   16200
cgtattgaca ggcttgagtc tgctgttaac ggtttgaaaa agtgatggtg gtttgttgtg   16260
ggtaaacagt tttggttagg tttactggag cgggcggcta agacttttgt gcaaacgttt   16320
gttgctgtgt tgggggtgac ggcgggtgtc acctatacgg cggagtcgtt tcgcggtttg   16380
ccgtgggagt ctgccctgat cacagctacg gtggctgcg tgttgtcggt tgctacatcg   16440
tttggtagcc cgtcgtttgt ggctggcaaa cctaaaacca cgcctgtgga tgcgggtttg   16500
gttccaccgg atgatggggg cttggttgag ccgcacatgg ttgatgtgtc ggatcctggc   16560
atgatcgagc cgattgatga tgcggatgtt gtcggctatg tgccgaggcg tgccgccgag   16620
```

```
tcggaggttg acacggtaga gtctactgtt gcataattga atatgtgtgt gccccagcgg    16680
tgctgccacg atctgtggtg gttgccgctg gggcactatt tttgtgtcta tagtattcta    16740
tgattcgttg ttgttgatgg tttcttcgat cagctggtcc aggtggaggc aggtagagat    16800
cgtttcgttg gcctggtgca gaacatcctg gccgataaca ttttgtggt tgtcgcggtg      16860 gcagatgatt gactgcatga tatcgtcggc ttccgattgt agtagtttgg tttggtatgc    16920
gattcctgcc agccaatcta tggcttcctg gcttgcccgt gtgtcgtctg gaatgccacg    16980
ggtgttgctg ttgtttgggt atcctgcact gtcgcagtcc cacaagattt cgctgcactc    17040
gtctagcgtg tcctggtcga tagcaaggtt gtcgaggctg acttctttga cggtaaggtt    17100
cacgttgtcg agtgagatgg gtacacggta ctggttttcg acaccgtcaa caatgttttg    17160
cagctgttgc atgttggttg gctgttgttg gatgattcgg tgtactactg ttttgagggc    17220
agtgtagggg atattggttg tgttgttcat ggttttatcc catccctgtg ttgtcgtcgt    17280
tgccgtcttg gtagtatcga ctgtttgcgt atcctgtgag ggtgatgagt gtttggtctg    17340
cccactgttt caccgtctgc cgggttactc cgagtcgttg ggctgccacc gaataggttt    17400
ggtcgtaccc gtatacttca cggaatgcgg ccaggcgtgc caaatgtttt cgctgtttgg    17460
atggctggca ggtgagggtg tagtcgtcga tggcagctg taaatcgatc atggtaacga     17520
tgttgttgcc gtggtgttgt ggcgcggttg gtggggtgg catgcctggt tcgacggagg     17580
gtttccatgg gcctccgttc cagatccatt gggcggcttg gatgatgtcg gcggtggtgt    17640
aggttcggtt cactggtcat cccctgaata ggttgtcgag gttgtctggg ttgctggtgt    17700
tggtggtgtc gaatcgtccc acacagtggc agtagtcgta catgagtttg ataatgtgtt    17760
ggtggtcgcc gaggtaggtg tttccgctga tactgtaggt ggctgtgccg tctttactga    17820
tggtgtattt ggcggtgatg gtttcggtg tttctgtgtt ggtgatgatg gcggtggtgg     17880
tggcgcctac tgtttgtagc ctggtggttt gggtgccgtc gtcgaggatg ttgtgacca    17940 tggtgtgtgt tctccttta aatgcttgtt tggttgtcgg ctagatgaat gatatcggat     18000
aaaggtttcg gctggtctag gtgttgtatg gttttgttgg ctagccgttt ggctaccctg    18060
tagcacattt tggtgtagtg tttgttgtct aggttgtggt attgttcccg caccgcaata    18120
tatagtaggg agtcttggta gaggtcgtct gcactgattg cggggtagtg tccggctgtt    18180
ttggtgcatg cccggtggag tgtgcgtaga tgatggtctg tgcccacac ccacgatgcg      18240 gtggtggcta ggtcggcttt tgttggtcgt ctgctcatag catctctttc atctggctat    18300
ctggtagtta tttggtgttt tgttgttgat agtgtagcac acgagtccgg ggtttccggt    18360
ggtgcctgtg cggtgccgga accatgtgga ttcgccttcc atggatgggc attggatgaa    18420
ggtgcgttgt ccttgctcag agatttcgag gtggtgccgg tgcccggcca tgagaatatt    18480
agatacggtg ccgttgtgga attcttggcc gcgccaccat tcgtattgtt tgccggtttt    18540
ccattggtgt ccgtgggcgt gcaggatttg tgtgcctgcc acatcaacgg tggtggtcat    18600
ttcgtctcgg ctggggaagt ggaagtgaag gttggggtat tggttgttga ctggtaggc    18660 ttctgcgatg gcgcggcagc agtccacgtc gaaggagtcg tcgtaggtgg tgacgccttt    18720
gccgaagcgt acggcttctc cgtggttgcc gggatggat gtgatggtga cgttggcgca     18780
gtggtcgaac atgtggacga gttgcatcat ggccatgcgg gtgagcctga tttgttccgt    18840
caagggtgtt tgtgtgcgcc aggcgttgtt ccgccttgt gacacgtatc cttcgatcat     18900
gtcgccgagg aaggcgatgt ggactcgttc gggtttgcct gcctgttgcc agtagtgttt    18960
tgcgactatg agggagtgca aatagtcgtc ggcgaagtgt gctgtttctc cgccggggat    19020
```

```
gcctttgccg atttggaagt ctcctgcccc gatgacgaag gccgcagtgc tgtagtcggt    19080
gtgggtgttg tcggctggtt ttgggggtgt ccatttggct agtttatcga cgagttcgtc    19140
tacagggtag gggttggttg cgggttggtg gtcgatgatt ttttgtatgg atcggccggt    19200
ttctccgttc ggtaaggtcc attcggagat gcgtgtgcgg cgtacagtac cattggctag    19260
attgtcgtcg atggtgtcga tggcgttgtc gtggttggct agctgtgtga gtagccggtc    19320
tatattgtct atcactggtt ttcctcttct gtttgtgggg tggtgttggc ttgtttgcgg    19380
cgatagtctt tgatgacggt ggcggagatg gggtatccgg cttgggtgag ctgttttgct    19440
agccatgagg cggggatggt tttgtcggcg aggacgtctg cggctttgtt gccgtagcgt    19500
tggataaggg tttcagtttt ggttgccatg atgtcctagg ggttgtgtgg tgggctgcca    19560
tcctgtgcgg cagtcgccgt cgtgtcctgg tttgcgtgtg caccatgaga cttcgccggc    19620
attgtggatg atggcacggc cgcatatgac gtcatgtagg tgttcgggaa acttatcgtt    19680
gttgttgtcc ccgtacatgt cgatcaagtg ttgggtttta gtaaccatca tgtctcctat    19740
gtgtgaaaga gtgtgcaaat actatgctgg tgtcatggat gtttatgcgg gtatggtttt    19800
catcaccttg ctgaacgtta cttggttact gtacatcatc tgggtgattt cctgatccgt    19860
tttgtcgggg tgctgttttc gcaggtttgc ccattggcag gcgttgtcgg tttcttgctg    19920
gagccgggtg agattgtttt cggtgatgat ttgtttccac attgtccacg agacgtcgag    19980
tcgtttgagc atgtcgatgg ctggcacgtt gaaggagttg aggaagagta tttcctccgt    20040
gtagtagtct ttttcgtatt ggtcccatcc gcttcggtgt ctgttgggct ggttttttggg   20100 gtaggcttcc cggcatactt tgtgcaaacg tttggccatg tctttgggta gcctaatgtc    20160
ggggttggcg cggatcatgg atcgcatccc atcataggtg gtgccccagg tgtgcatgat    20220
atgtagtggg tcttcaccat cagcccattt ttctgcacag atggcgaggc ggatacgcct    20280
cctagtggcc ttactcgtgt cgcggcggcc ggggatgggg catgtgtcga gggggtccat    20340
gatgcttttt atgcctttct tggagtgatg ttttgtttgt ctggttttat tgtagcactg    20400
tgtctagtgc ttgtgtcaac cctgtttttc cggcctgcag ataggtgtct gtgacatccc    20460
ccagggtgag gggtacgtgt atggcttggg ggagtgccgt ctggatggtt tgtgccatct    20520
ggtcgcctgc tttgtcgggg tcggaccaga tgtagatgcg gtcgtagcct tcaaaaaatt    20580
tggtccaaaa gttttgccac gaggttgcgc cgggtagggc tacggccgac catccgcatt    20640
gttcgaggat catggagtcg aattcgcctt cgcaaatgtg catttcggct gccgggttgg    20700
ccatggcggc catgttgtag atggagcctg tgtcccctgc cggggttaga tatttgggt    20760 ggttgtgggt tttgcaatca tgctggagtg agcagcggaa acgcattttt cgtatttcgg    20820
ctggctcccc ccagacgggg tacatgtagg ggatggtgat gcactggttg tagttttcgt    20880
ggcctgggat ggggtcattg tcgatgtatc caaggtggtg gtagcgggct gtttcttcgc    20940
tgatgcctct tgctgagagg aggtcgagta tgttttcgag gtgggtttcg tagagggctg    21000
aggctttctg gattcggcgg cgttccgcaa tgttgtaggg ttgtaggctg tcgtacatta    21060
gggttttctt tctctagttg ttgtttcagt tgggcgagtc cgcctccgat accgcatgtg    21120
tggcagtacc agacgccctt gtcgaggttg atgctcatgg agggctggtg gtcgtcgtgg    21180
aacgggcaga ggatgtgttg ctcgttcctg gaaggattgt accgtatctg gtgggtgtcg    21240
aggaggcggc gggtgtcaga ggtgtgggag gagctcgttg agggttgata ccacataggc    21300
ttcgctccag ggtttgttgc gctgtttcat gacgacgagt ccgatggtgg aattgttttg    21360
```

```
tttgtttcgg tgtgtttcgt agttgcgtgc ctcccggctg gcttgtttca cgaattcggc   21420
gaggtgtgcc tgtccggctt tcgcctcgat aatgtaggtt ttgttgccgg ttgtgaggat   21480
gaggtcgcct tcgtcttcgc ggccgttgag gtggaggcgt tctatatcat ggccggtgtc   21540
gcgtagctgg tggaggagtc tggtttccca ttcggctccg gctcggcggt tgcgtgcctg   21600
ttgtgtcgac atgatagtcc tttgtggtgt tcggtcatgt tccatggctg ttttctgcg    21660
aggggcccga agaatgtgta ttcggggtag gctcgtagtc gttcgtatcg ggttccgtct   21720
gggctggatt tgcctgtgcg ctgtttcaac actgcgatgc gtgcctctgc cggtatcgtg   21780
agcccgttgc cgttgtcctc gccaccataa agtgagactc cgaggatgag ttgtggtttt   21840
tcggagaggc cgttttttgat ttccctgcgt gctggcgggt gttcgatgtc ggttccggtt   21900
ttgtcggttg cgtggtgtgt gacaataatg gtggagccag tatccctgcc caatgctgtg   21960
atccattgca tggcttcttg ctgtgcctgg tagtcggatt cgcagtcttg gatgtccatc   22020
aggttgtcga tgacgatgat gggtgggaag gtgttccaca tttccatgta ggcttgcaat   22080
tccatggtga tgtctgtcca tgtgatgggt gactggaata agaatgtgat gtgttggccg   22140
tggtggatgc tgtctcgata gtattctggc ccgtagtcgt cgatgttttg ttgtatctgt   22200
gtggtggtgt gttgggtgtt gagtgagatg attcgtgtgg aggcctccca gggtgtcatg   22260
tccctgata tgtagagggc gggctggttg agcatggcgg tgatgaacat ggctagccct    22320
gattttggc tgccggaccg ccccgcaatc atgacgagat ccccttttgtg gatgtgcatg    22380
tccaggttgc ggtagagggg ttctagttgt ggtatgcggg gcagctcggc tgcggtttgg   22440
gaggctctct cgaaggatcg ttgtagagag agcatcggga ccttatctat ctattggttg   22500
gatgtgtatt ggtggtcaga tggagtcgat atcgatgtca gtagaggctg tggtgtcgtc   22560
tagctggccg ttatcgcgct tgtctacgta ttcggccacc ttatcgtaga tggcgtcgtc   22620
taatggtttg agcacaaccg cgttgaagcc gttttttggtg cgtacggtgg cgagtttgaa   22680
ggcctgctcc tcgccaaggt aggtttctag atcgcggatc atggagtggg ggcggtcgtt   22740
gttgccgcgt gctttctcga taatggcgtt ggggatggtt tctggggtgc cgttgttgag   22800
atcgtctagg gtgtggaaga ttgtgacatc agcgtagatg cggtctgcga cctgtccacc   22860
gtagccttcg gtgttgtgtt cgacgtcgtg gactttgaag gcgatggcgg tggcgtcctg   22920
gtttcgggag gggttgaaga aggtgctgtt actgttgttg tttcggtagt ttgcgagtcc   22980
cattgttgtt tcctttactg tttgtgttgt tttgtttgtt ggtttgtgtc ggtttatcgg   23040
gtgaggctgt ttcgtttatt ccggaaagct tcggacacgt cactgttact agtgatgatc   23100
tttttgtact gtttcagaag gtcggctagc tgtgccttgc ttgtggcatt gttaattttg   23160
tctatgacga tgctgttttc gtttgatgcg atattgttta cgtagtcttt ggcggcttgg   23220
ttgtatcggt cttggaggat gatggatgct gtggcgatca gtgttgccag gtcccagttc   23280
cttgccgcgg agctgttttt gagtccgcct aacaggtcga tgatagtctt ctttacctgg   23340
tcggcggtgt ctccgcggat gacggtccat ggggcggcgt agtcgcctcc gtatttgagt   23400
gtgacggtga atcggtcttc gtctgtgttg tcggtcactg gtgctccttg tcttcttttg   23460
ttggggctgt gatggtggtt tctataggt acctgtaggc atctttcccg ttgacagccc    23520
agcaggcgtc ctggacgggg cagcctttgc agagtgctgt gacgtggggt acgaatatgc   23580
cttggctgat tcctttcatt gcttgactgt acatggatga tacatgccgg taggtgttgt   23640
tgtcaagatc gtacagttcg gtggccgttc cctgcttggc ggactgtttg tctgttttgg   23700
ttgatgcggg tgtccaaaac atgccttttg tcacatcgtt gccgtgttgt tctagcatgt   23760
```

```
acctgtatgt gtgcagctgc atactgtcgg cgggtagacg gccggttttg aggtcgagga     23820
tgaaggtttc gccggtgttg gtgtcggtga aaacgcggtc gatgtagcca acgatctggg     23880
tgccgtcctg gagggtggtt tctaccgggt attcgatgcc cggctcgccg tcgataacag     23940
cgatagcata ttctgggtgg ttgctcctcc atgttttcca gcggtccaca aaggtggggc     24000
cgtaaaccat ccaccagtcg tagtctttct tgtgtggccc gcccgactcg cacatgtttt     24060
tgcatattct gccggagggt ttgatttctg tgccttcgga ttcggcgagg gcgacttggg     24120
tgtcgaaaat gttttgaag gatgcaagtt tgtctggcag tgcagggtat tcggcgggat     24180
tgtacaggtg taggtcgtat tgttcggtga tgtggtgtat ggcgcttccg gcgatggtgg     24240
cataccaggt gtggtgttgg gcatggtagc cgtgggatag gcgccatttt tctccgcatt     24300
cggcccactg tgacagtgat gagtaggaga tgtggcctgg atggttgatg gttttcgggt     24360
attgtgctag aggcattact ggtcgccttt gtgggtgttc catgggttgc gggtgtcttg     24420
gccggcattg tgttgctggt atgcgaggag tgcgaggcag tgccaggcag catgtgccag     24480
atgcggcaaa tgtgattcgt ggtcgaggtt gttgccttgc tgccatgata gtaggtgccg     24540
gtagagggcg tcaacgctgt ggctccacgg gtatcctccg gtccagttgt tgtcgccgta     24600
tttggtggca ccgtatccgg ctacttcgcc tagggcgtga agggatgcgg ggtcgatgag     24660
ggagagcctg cagagtttca attcttttcg ggcaccgctg ttggggtcgg tgtacatgcg     24720
ggtgggctca tccatgagat gtgtgctcct taagggtggg ttactggttg ttgtgggcga     24780
gtgctactgc gagaataatg atggcgaggg tttcagcgat cagtatgggt gttgtgatca     24840
tttgctgtct ttgggctggt aggtgagggt tgaggcaccc aggagggtgg cgagggcgca     24900
tgcggcgatg atggcgaggg ctgccttgtg tggggtgctg gttgcgtaca tccatgtgat     24960
gatgccgcct tggatccagg ctaggctggt gaagaacgtt tcgtaactgt gtagctcaat     25020
gttgttgttg ggtgtgttca tgcttgctcc tgaagaatgg tgttgatggt tttataaatg     25080
ttgtacaggt cggtttcgat agataacagt tggttgattt ggtggtcgag gttgatgtct     25140
gggttgaggg tgttgatgcg ggaggcgata tcggtggctg tgcgtagtgt gccgccggtg     25200
tggtgaataa tgtgtgccgt gtcggcgagt ccggtggtga cagcgtagtg ggagaggata     25260
ggcatagcgg gggaatgttc cttggcgggt tactgttgcg ggttgatgtt gaggtcggtg     25320
acgtgcgggt ggtcttctgt tccggtgacg aggcagtgga cggtgacggg tagtttggat     25380
gcgccgggct gtttcatggt ggcgccgtag acgatgctga atgtgtcttt accgatggtt     25440
ttgtggagtt ggaggtcgat gtcggggttg ccgttccagt tgacgccttg tgctgcggcc     25500
tgttgttcgg ctttgcggtt gcaggtgtgt gctgccgtga tcatggtgag tccggttgcg     25560
gtttcttcac cccttgcttg ggcttgcttg tgggttttgg cctgctcggc ttgtagggat     25620
cgggtggcgg ctgcctgccg tgccgctttc tcggctttgc gctgttgggt agtcttgggg     25680
gtccattcgg tgttggctgt ggtggcctgt ggggcgggtt gtgaggcgag tggcggattg     25740
tcgtctgggg ctggcaggaa ggatgcggcg gcaatgatgg cggctgtgat tccggcgatg     25800
gtgtagccgt ttttcttgtt catgactgtt gtcccctttc cggggtgttg ttcgttgctg     25860
acatgattaa tacttccagt gactggacct catgtcaaga ctgcgctcaa atgttgtgag     25920
cgtttcctgt atggttagat gttttatcgg gcacacaggg tgagtagatg gccaacattg     25980
atgcaggtca cgttccagta gagttgtgtg gcttcaccgc cggtgagcgg cttccactcg     26040
ttgtggctga acacggtgcc atcggatgct atgaatgtgt tggggcgtag cttgtgaagc     26100
```

```
tcggcttcca cgctctgccg gtaggcttcg gcgaggccct caaaatccat gtggtcgcag   26160
gagagatttt cgaggcgtgt caggtcgaag ggtgtgggc agtcgtagct ggcggggtg     26220
tagagctggg tgaagtggtc ggcgatcttc tgcatgatta tttcctttc gttgctgata   26280
acgttgttga gggtttatcg ggtggatgcg acaaggatgg cgtctacatc gatcacgtcg  26340
atcatgtcgt ggagttcctc cgcttcgttc tcggcgagtg gctgccagtc gtagtcgccg  26400
tacacggcgc cgtcaagggt gacagtccac agtggccgga tgagtcgtat ggcttcttgt  26460
actttagcgt ggtacatgcg gcgcaccata tcgagatcga tgtcgtctga atggtttccg  26520
gtgaggctgt ggaggctaag cgggtcgatt tctgtctgcc tgtagaggga tgtgaaggat  26580
ggggtgatga gtgtgccatc catgggtgat gttcctttct ggattgtctt ggttgttgtg  26640
gtttctagag tgtgtgggct gcgactcaca gtcaaggctg cgctcaatcc gaatgagcgt  26700
ttcatgctgg agtgtcgggt gtgacagatg tcactgaagc ctttatggcc tctcccagcg  26760
tctcaaatct tctaggggta ggattatgca gggttgacca tactagtcga ttctagggcc  26820
attctagggc gtctgagggg tatatctggg tgatagcagg tgtggcagat gatctagcga  26880
gtcaaggtgc cgagcttaga cataagatct atcatctagg tgtgtgagat gtatcacact  26940
ctcctggctt ggtgtgcact ctcgaggcca ctctgccgat ctggcgtgga gggtgtagcc  27000
cagaaatgcc gtttaaatcc ttcacgcgga gcctaggagc gccttgcagg gtgggggcta  27060
ggtatttata cccccagcat attctgatcg attctatacg cccccagaag cctgatacac  27120
gattcgctat ccaggcgcag atcatcagcc cctatcctgc ttagctaagc ctcaactatg  27180
tggacagtgt tggatgctaa gagggaagaa ggatacggta aaagaaagaa gggggagtat  27240
cagccttcac accggaggta cttaagttca ccttagagac ttagcactga gcattgagca  27300
ctgagcagga tcagcccaga aaggggtaca cgccatcagg ggaggcttga gagtacgagg  27360
agccctagcg acgagtactc gaaagcctga gggaatacc tcagcactga tgggcctagc   27420
gtgttcggaa aggacacagg agtacagtgt gacagtcttt ccgggagcta aactccttcc  27480
ggctagggca aacacccgtc ctaggctagc ccacaccctc atctgttaac cttccgttca  27540
ttaaacgtta aggaaacttt taggtttgat ttttggacct ttactaccaa aaacacccgt  27600
ttacacccct caaacccgcc tatagagcca aacgccggtg ttgagggtat ctctacctag  27660
tgtgataggc tggacaggta gccagctgga cgcaaggccg aaatccgctg acgcggcttt  27720
cacccttaca tccatcagtc taccaaacac tttaaagctt caaggcttag cgctaagccc  27780
ttaaaacctt aacgcttagc accgagccct tgagggctc ggcatcagtc ttaggtactt   27840
taagtaactt taaaaccttc aaggcttagc ccttaaggat ctaagttact cttaaagctt  27900
taaagtctta aaataaatat ataaccttaa tagttaaacg ttaaaagctt taaaccttaa  27960
cacttaagtt aagtataaaa ccttaaaggc ttagcactta aggatataaa ctttacatca  28020
gtgtttaaga ctttaaaaact taaagtaatt attaaaactt aaaggtttat aagctttaag  28080
cacttaaagt aactataaga ctttaaagac cttaagtact taaagttaac catcagtctt  28140
aaactttaat attataccta taagtcttaa agcttatagg tataaaagtt ttagaagagc  28200
taaggggtta acttctttac ttctctactc tctttggttc tttctctctt ctcttctttt  28260
cttcatcagg ggagaagaga aacctttac cgtcaacgct gatgggcttt tcgccgtgtg   28320
actcgtgtgc ttctggtcgc aagctcccat cgcacactcc ccacactctt tcacccgtgt  28380
cccctttcag gcttagcatg ttcggctgaa ggcgtacggc gtgtcacgcc aacacccta    28440
acaccaggta agacttaaag tacatattat atgtagaaga cttaaaacc ttaagggtgt    28500
```

```
tcccgcttgg cccgtgtcct ttaacgctag gcgctaagcc tgaaacgcga acacccatcc    28560 accccattt  tgcttccgtg tccttctctt tttgacaccg ctgggggcg  atgtgatctt    28620 tctcacatgc caggggttag tggagaaaac aaacacccca ccacaaacag aacaccccct    28680
caaacgaaca aaacagggcc tagaatcgaa tagaagggca ccggtagagt attcctaccc    28740
ccaacacgtt ccaggctgtt acaggagcaa tgagaggctc acaggggcca taggagatca    28800
gggggcgtga tggcacacac caaccgcaca gccagccaag cccaccggcg ctggcgggcg    28860
cgactcatca cccaagcacg caagcaaggc caaaccgaat gcccactctg cggagcccag    28920
atagcctggg acacacacga cctgccaacc agccccgaag ccgaccacat cacacccgtc    28980
agccgcggag gactcaacac cctcgacaac gggcaaatca tctgcagaac atgcaacaga    29040
agcaaaggca atcgcagcga accaaacatt agtttccaac aacaaaccac aaaaaccttg    29100
atttcatggt gaaaaaaccc acaaacccca cgggaaccac cccctgcaca ccc           29153

<210> SEQ ID NO 5
<211> LENGTH: 29109
<212> TYPE: DNA
<213> ORGANISM: Bacteriophage 1894

<400> SEQUENCE: 5
tcccttttgt ggattgtctg tttgtcgact ttttgtgttg gtggtgagtg ttgtgcagcc      60
tgagcttcct gggtctcgtg agtggtgtgg ggagacgcgt cagtggtggc gtgtgtgggg     120
tgaggatagt cgcgcgcagt acgtgtctga tgaggagtgg ctgtttctca tggatgctgc     180
ggtgattcat gattgtgtgt ggcgtgaggg tcgcgcggat ttggtggctt cgttgcgtgc     240
tcatgtgaag gcttttatgg gcatgttgga tcgttattcg gttgatgtgg cgtctggtgg     300
ccgtggtggg ggttctgcgg tggcgatgat tgaccggtat aggaagcgta aaggggccta     360
atgtcgagtg ttgttggttc tcaggttcct cgtcaccggg tggctgcggc gtattcggtg     420
tctgctggcg gtgatgctgg ggagttgggt cgtgcgtatg ggttgacgcc tgatccgtgg     480
cagcagcagg tgttggatga ttggctggct gtcggtggta atggcaggct tgcttcgggt     540
gtgtgtgggg tgtttgtgcc tcgccagaat ggcaagaatg cgatccttga ggttgtggag     600
ttgtttaagg cgactattca gggtcgccgt attttgcata cggctcacga gttgaagtcg     660
gctcgtaagg cgtttatgcg gttgaggtcg ttttttgaga atgagcggca gtttcctgac     720
ttgtatcgta tggtgaaaac gatcagggcg acgaatggtc aggaggctat tgtgttgcat     780
catccggatt gtgccacgtt tgagcgtaag tgtggttgtc cggttggggg ttcggttgag     840
tttgtggccc gttctcgggg ttctgctcgc gggtttacgg ttgatgattt ggtgtgtgat     900
gaggctcagg agttgtcgga tgagcagttg gaggctttgc ttcctacggt gtctgcggct     960
ccttcgggtg atccgcagca aatttttttg ggtacgccgc ctgggccgtt ggctgatggt    1020
tctgtggtgt tgcgtttgcg tgggcaggct ttgtcgggtg gtaagaggat tgcgtggacg    1080
gagttttcga ttcctgacga gtctgatccg gatgatgtgt cgcggcagtg gcggaggttg    1140
gcgggtgaca ctaatccggc gttgggtcgc cgcctgaatt ttgggactgt cagcgatgag    1200
catgagtcga tgtctgctgc cgggtttgct cgggagcggc ttggctggtg gatcgtggc     1260 cagtctgctg cgtctgtgat tccggcggat aagtgggctc agtcggctgt ggatgaggcg    1320
agtttgtctg gcggtaaagt gtttggtgtc tcgtttttctc gttctgggga tcggttgct    1380 ttggcgggtg ctggccggac tgatgctggt gttcatgttg aggttattga tgggctgtcg    1440
```

-continued

```
ggaacgattg ttgatggtgt gggccggttg gcggactggt tggcggttcg ttggggtgat    1500
actgaccgga ttatggttgc cgggtctggt gcggtgttgt tgcagaaggc gttgacggat    1560
cgtggtattc cgggccgtgg cgtgattgtg gctgatactg gcacctatgt ggaggcgtgt    1620
caggcgtttt tggagggtgt gcgttcgggt gttgtgtctc atccgcgtgc cgattctcgc    1680
cgtgacatgt tggatattgc ggtgaggtcg gcggttcaga agaagaaagg ctctgcgtgg    1740
ggttgggggtt cctcgtttaa ggatggttct gaggtgcctt tggaggctgt gtcgttggcg    1800
tttttggggg ctaaacgtgt tcgtcgtggc cgtcgggagc gtagtggtag aagcgggtg    1860
tctgtggtat gaactcggat gagttggctt tgattgaggg catgtacgat cgtatccaaa    1920
ggttgtcttc gtggcattgt cgcattgagg gctactatga gggttctagc cgggtgcgtg    1980
atttgggggt tgctattcct ccggagttgc agcgggtgca gacggtggtg tcgtggcctg    2040
gtatagctgt ggatgctttg gaagagcgtc tggattggct tggctggact aatggtgacg    2100
gctacggcct ggatggtgtg tatgctgcga atcggcttgc tacggcgtcg tgtgatgtgc    2160
atttggatgc gctgattttt gggttgtcgt ttgtggctgt tatcccccag gatgatgggt    2220
cggtgttggt tcgtccgcag tcaccaaaga attgcacagg caagttttcg gctgacgggt    2280
ctcgtctgga tgctggcctt gtggtgcagc agacgtgtga tcctgaggtt gttgaggcgg    2340
agttgttgct tcctgatgtg attgttcagg ttgagcggcg gggttcgcgt gaatgggttg    2400
aggtggatcg tataccgaat gtgttgggtg ctgttccgct tgtgcctatt gtgaatcgtc    2460
gccgtacttc taggattgat ggccgttcgg aaattacgag gtctattagg gcttacacgg    2520
atgaggctgt gcgcacactg ttggggcagt ctgtgaatcg tgatttttat gcgtatcctc    2580
agcgttgggt gactggcgtg agtgcggatg agttttcgca gcctggctgg gtcctgtcta    2640
tggcttctgt gtgggctgtg gataaggatg atgatggtga cactccgaat gtggggtcgt    2700
ttcctgtcaa ttcgcctaca ccgtattcgg atcagatgag actgttggcg cagttgactg    2760
cgggtgaggc ggctgttccg gaacgctatt tcgggtttat cacgtctaac ccacctagtg    2820
gggaggcttt ggctgccgag gaatctcggc ttgtgaagcg tgctgagcgg cgtcaaacgt    2880
cgtttggtca gggctggctg tcggttggtt ttttggctgc caaggcgttg gattctcgtg    2940
ttgatgaggc cgattttttt ggtgatgttg gtttgcgttg gcgtgatgct tcgacgccta    3000
cccgggcgga tacggctgat gctgtgacga agcttgtggg tgccggtatt ttgcctgctg    3060
attctcgtac ggtgttggag atgttggggc ttgatgatgt gcaggttgag gctgtgatgc    3120
ggcatcgtgc tgagtcgtct gacccgttgg cggcactggc tggggctata tcgcgtcaaa    3180
ctaacgaggt atgataggcg atggcttcgg gggttgaggc gaggcttgcg gcgactgagt    3240
atcagcgtga ggcggtcagg tttgctggga agtatgcggg ctattattct gagcttggtc    3300
gtttgtggcg tgccggcagg atgagtgaca cgcagtatgt tcgtttgtgt gtggagttgg    3360
agcgtgccgg ccatgatggt tcggcatcgt tggctgccag gtttgtgtcg gattttcgcc    3420
gattgaatgg tgtggatcct ggtttgatcg tgtatgacga gtttgatgct gcggcggctt    3480
tggctaggtc tatttcgacc acgaagattc ttgagagcga cccggatagg gcgaatgaca    3540
caattgatgc gatggcggcg ggttttgatc gggctgttat gaatgctggc cgcgacacgg    3600
ttgagtggtc tgcgggtgcg cagggcaggt cgtggcgtcg ggttactgat ggtgatccgt    3660
gtgcttttgt tgccatgttg gctacgaggt cggattatac gaccaaagaa agggcgctca    3720
ctactggaca tacgcggcgt cataagcgtg gcggtaagcg cccgtttggt tcgaaatatc    3780
atgatcattg cgggtgtacg gtggttgagg ttgttggccc ttgggaacca aatagggctg    3840
```

```
atgccgagta tcagaggacg tatgagaagg cccgtgagtg ggttgatgat cacgggttgc   3900
agcagtcgcc tggcaatatt ttgaaggcta tgcgtactgt tggcggcatg agataatttg   3960
ctgtggtttc cggttgtgcg ccgccggtta ttggtgcaca ttgttgtctc ccgcacgggg   4020
gtcaacaatg ttgtgttgtt ttccgcaagg agtgtagggt taggctatgg ccgatcagag   4080
tgttgaggaa cagaatgttg acaatgatgt tgtggagtcc ggaaaggata acggcattgt   4140
tgatacagta aagatgatg gcgggcagga ggtagccgac aatcagttga agaatgaagg   4200
cgagggtaaa tcgccgggga ctgattggaa ggcggaggcc cgtaagtggg agtctcgtgc   4260
taaaagtaat ttcgccgagt tggagaagct tcgtacatcg agtgaagatt ctggatctac   4320
tattgatgag cttcgccgca agaatgagga actcgaagac aggatcaacg gtttgttct    4380
tgagggtgtg aagcgcgagg tggcttcaga gtatggtttg tccagtgatg cgatcgcttt   4440
cttgtcgggt ggcgataagg agtcgcttgc cgagtctgcg aaagctttga agggtttgat   4500
cgaccatagt agtggtggcg cgggtgtgcg ccgtcttgcg gggagtgccc ccgttgatga   4560
tgttaaacga cgtgagggtg tcgcgtttgt ggatgctctt gtcaataatt ctaggagatg   4620
atttgtgatg gctgacgatt ttcttctgc agggaagctt gagcttcctg gttctatgat   4680
tggtgcggtt cgtgaccgtg ctatcgattc tggtgttttg gcgaagctct cgccggagca   4740
gccgactatt tttggccctg ttaagggtgc cgtgtttagt ggtgttcctc gcgctaagat   4800
tgttggtgag ggcgaggtta agccttccgc ttctgttgat gtttcggcgt ttactgcgca   4860
gcctatcaag gttgtgactc agcagcgtgt ctcggatgag tttatgtggg ctgatgctga   4920
ttaccgtctg ggtgttttgc aggatctgat ttccccggcg cttggtgctt cgattggtcg   4980
cgccgtggat ctgattgctt ccatggtat tgatcctgcc actggtaaag cggctgccgc    5040
tgtgcatact tcgctggata agacgaagca tattgttgat gccacggatt ctgctacgac   5100
cgatctggtc aaggctgtcg gcctgattgc ggggctggt ttgcaggttc ctaacggggt    5160
tgctttggat ccggcgttct cgtttgctct gtctactgag gtgtatccga aggggtctcc   5220
gcttgccggt cagccgatgt atcctgctgc cgggtttgcc ggtttggata attggcgcgg   5280
ccttaatgtt ggtgcttctt cgactgtttc gggtgccccg gagatgtcgc ctacctctgg   5340
tgttaaggct attgttggtg atttctctcg tgttcattgg ggtttccagc gtaacttccc   5400
gatcgagctg atcgagtatg gcgatccgga tcagactggt cgtgaccta aagggccataa   5460
tgaggttatg gttcgcgccg aggctgtcct gtatgtggct atcgagtcgc ttgattcgtt   5520
tgctgttgtg aaggagaagg ctgcaccgaa gccgaatcct ccggccgaga actgattcat   5580
ttgttgcggt gatatgtaca tgtgcagggg gtggtgttga tgggtatcat tttgaggcct   5640
gaggatattg agcctttcgc cgatattcct cgagagaagc ttgaggcgat gattgccgat   5700
gtggaggctg tggctgtcag tgtcgccccc tgtatcgcta aaccggattt caaatacaag   5760
gatgccgcta aggctattct gcgcagggct tgttgcgct ggaatgatac tggcgtgtcg    5820
ggtcaggtgc agtatgagtc tgcgggtcct ttcgctcaga ctacacggtc taatactccc   5880
acgaatttgt tgtggccttc tgagattgcc gcgttgaaga agttgtgtga gggtgatggt   5940
ggggctggta aggcgttcac tattacaccg accatgagga gtagtgtgaa tcattctgag   6000
gtgtgttcca cggtgtgggg tggcggctgt tcgtgcggtt ctgatattaa cggctgcgat   6060
ggtcctttgt gggagatatg atatgactcg ttttccttat ggtgaaacgg ttgtgatgct   6120
tcagccgact gttcgtgtcg atgatcttgg cgacaaggtg gaagactggt ctaagcctgt   6180
```

```
cgagactgtg ttacataacg tggccatcta tgcttccgtt tcgcaggagg atgaggccgc    6240 gggcgtgac tctgactatg agcattggac actgcttttc aagcagcctg ttgaagctgc    6300
cggttatcgt tgccggtggc gtatccgggg tgttgtgtgg gaggctgacg ggtctcctat    6360
ggtgtggcat catccgatgt ctggctggga tgctggtacg caggttaatg tgaagcgcaa    6420
gaagggctga tagattgtgg ctcaggatgt gaatgtgaag ctgaacttgc cgggtattcg    6480
tgaggtgttg aagtcttctg gggtgcaggc tatgttggct gagcgtggcg agcgtgtcaa    6540
gcgtgcggcc tcggcgaatg tgggcggtaa tgctttcgat aaggcccaat accgtaatgg    6600
tttgtcgtcg gaggtgcagg ttcaccgtgt tgaggctgtc gctcgtatag gcaccacata    6660
taagggtggg aagcgtattg aggcgaagca tggtacgttg gctcgttcga ttggggctgc    6720
gtcgtgatcg tctacgatga ccccaggaag tgggctaaac gcgtgctcaa ggatgatggc    6780
tggctgtctg atatacccctg tgtggggacg gtgcccgatg attttacggg tgacctgatt    6840
tggttggcgt tggatggtgg cccgcagttg catgtgcgtg agcgtgtttt tttgcgcgtg    6900
aatgtgtttt ctgatacgcc tgatcgggct atgtctttgg cgcgtcgtgt tgaggctgtt    6960
ctggctgacg gggttgatgg tgatccggtg gtgtactgta aacggtctac tggtcctgat    7020
ttgctggttg atggtgcacg ttttgatgtg tattcgctgt tcgagctgat atgtaggcct    7080
gcggagtctg agtaagctta ttgtttttgt tttaatgtaa ttgtttgata tttaatgggg    7140
gttgtgatgg ctgcaacacg taaagcgtct aatgttcgct ctgctgttac gggtgacgtt    7200
tatattggta aagctcatgc cggtgatact attgatggtg tgaaaacggt tcctgatggg    7260
ctgactgctt taggatattt gtcggatgac gggtttaaga ttaagcctga gcgtaaaacg    7320
gatgatttga aggcttggca gaatgcggat gttgttcgca cggttgctac cgagtcgtct    7380
atcgagattt ctttccagtt gatcgagtct aagaaggagg ttattgagct gttttggcag    7440
tcgaaggtta ctgctggatc cgattcgggt tcgttcgata tttctccggg tgccacgacg    7500
ggtgttcacg ccctgttgat ggatattgtg gatggcgatc aggttattcg ctactatttc    7560
cctgaggttg agttgatcga tcgtgacgag attaagggta agaatggcga agtgtacggg    7620
tatggtgtga cgttgaaggc gtatcctgcc cagattaata ataagggtga tgcggtgtcg    7680 ggtcggggt ggatgacggc tttaaaagct gatactcctc cggttccgcc ttctccgaag    7740
cctcagccgg atcctaatcc tccgtccgag aactgataca cgattttagg gattgttgat    7800
agatgagtga cacaggttac acgttgaaga ttggtgaccg tagctgggtg ttggcggatg    7860
cggaggagac ggctcaagct gtgcctgccc gcgtgtttcg ccgtgcagct aagattgccc    7920
agtcggggga gtctgcggat ttcgcccagg ttgaggtgat gttttctatg ttggaggctg    7980 ccgcccggc tgacgctgtg gaggccctgg aggggcttcc tatggttcgt gttgccgaga    8040
ttttccgtca gtggatggaa tacaagcctg accagaaagc ggcctccttg ggggaatagt    8100
ttggctccac ggcctgattg atgattatcg tggggccatc gaatatgatt ggaggacccg    8160
gttcggttgc tcggtttatg atgttggtgg cccgcagatg tgttggggtg aggctgtccg    8220
gctggctggc gtgttgtgta ccgatacgtc tagccagctg gcggcccacc tgaatggttg    8280
gcagcgtccg tttgagtggt gcgagtgggc ggtgttggac atgctggatc attacaggtc    8340
tgctaatagt gaggggcagc cggagcctgt ggcgaggccg acggatgagc gtagggcccg    8400
gtttacgtct gggcaggtgg acgatatttt ggcgcgtgtt cgtgccggtg gcggggtgtc    8460
tcgcgagatt aatattatgg ggtgaatagt gtatgtctgg tgagattgct tccgcatatg    8520
tgtcgttgta tacgaagatg ccgggtttga aggcggatgt tggtaaacag ctttctgggg    8580
```

```
tgatgcctgc ggagggtcag cgttcgggta gcttgtttgc taagggcatg aagttggcgc   8640
ttggtggtgc cgcaatggtg ggtgccatca atgttgctaa gaagggcctc aagtctatct   8700
atgatgtgac tattggtggc ggtattgctc gcgctatggc tattgatgag gcgcaggcta   8760
aactgactgg tttgggtcat acgtcttctg acacgtcttc gattatgaat tcggctattg   8820
aggctgtgac tggtacgtcg tatgcgttgg gtgatgcggc ttctactgcg gcggcgttgt   8880
ctgcttcggg tgtgaagtct ggcgggcaga tgacggatgt gttgaagact gtcgccgatg   8940
tgtcttatat ttcgggtaag tcgtttcagg atacgggcgc tatttttacg tctgtgatgg   9000
ctcgcggtaa gttgcagggc gatgacatgt tgcagcttac tatggcgggt gttcctgtgc   9060
tgtctttgct tgctaggcag acgggtaaaa cgtctgctga ggtgtcgcag atggtgtcga   9120
aggggcagat tgattttgcc acgtttgcgg ctgcgatgaa gcttggcatg ggtggtgctg   9180
cgcaggcgtc tggtcagacg tttgagggcg ctatgaagaa tgttaagggc gccctgggtt   9240
atcttggtgc tacggctatg gcgccgtttc ttaacgggtt gcggcagatt tttgttgcgt   9300
tgaatccggt tatcaagtcg gtgacggatt ctgtgaagcc gatgtttgct accgtcgatg   9360
ctggtattca gcgtatgatg ccgtctattt tggcgtggat taaccgtatg ccggctatga   9420
tcactcgaat gaatgcacag atgcgcgcca aagtggagca gttgaagggc attttttgcga   9480 gaatgcattt acctgtccct aaagtgaatt tgggtgccat gtttgctggc ggcaccgcag   9540
tgtttggtat tgttgctgcg ggtgtgggga agcttgttgc agggtttgcc ccgttggcgg   9600
tgtcgttgaa gaatctactg ccgtcgtttg gtgctttgaa gggtgccgcc ggcgggcttg   9660
gcggcgtgtt tcgcgccctg ggtggccctg ttggtattgt gatcggcttg tttgctgcca   9720
tgtttgctac gaacgcccag ttccgtgccg ctgttatgca gcttgtggct gtggttggcc   9780
aggcgttggg ccagattatg gccgctattc agccgctgtt tggtttggtt gctgggctgg   9840
tggcccagtt ggcgccagtg tttgcccaga ttatcggtat ggttgccggt ttggctgccc   9900
agttggtgcc tttgattagt atgcttgtcg cccggctagt tcctgtgatc acgcagacta   9960
ttggtgcggt gacgcaggtt gctgccatgt tgttgcctgc gcttatgccg gttattcagg  10020
ctgttgtggc tgtgatacgg caggttgttg gcgtgatcat gcagttggtg cctgttttga  10080
tgcctgtgat tcaacagatt ttgggtgcgg tcatgtctgt gctgccgcct atcatcggcc  10140
tgatccggtc gctgatacca gtcatcatgt cgattatgcg tgtggtgatg caggttgttg  10200
gtgtcgtgct acaggtggtg gcccgcatta ttccggttgt gatgccaatt gtgacagctg  10260 tgatcggggtt tgttgcacgt attcttggcg ctattgtgtc tgctgcagcc cgcattattg  10320
ggactgtcac ccgtgtcatc tcatgggttg tgaatcattt agtgtctggc gtgaggtcta  10380
tgggtacggc catcttgaat ggctggaatc atattagagc gtttacgtct gcgtttatta  10440
acggtttcaa gtcggtgatt tctggcggcg tgaacgctgt tgtggggttt tttgcccggc  10500
tgggttcttc ggttgcttct catgtgaggt ctggttttaa cgcggctcgt ggcgctgttt  10560
cttctgcgat gaatgctatt cggagtgttg tgtcttcggt ggcgtctgct gttggcgggt  10620
ttttcagttc gatggcgtct agggttcgta gtggtgctgt gcgcgggttt aatggtgccc  10680
ggagtgcggc ttcttctgct atgcatgcta tgggttctgc ggtgtctagt ggtgtgcatg  10740
gtgtgctggg ttttttccgg aatttgcctg gcaatattcg gcgtgcgctt ggtaatatgg  10800
ggtccctgtt ggtgtctgct ggccgtgatg tggtgtctgg tttgggtaat ggtatccgga  10860
atgctatgag tggcctgttg gatacggtgc gtaatatggg ttctcaggtt gcgaatgcgg  10920
```

```
cgaagtcggt gttgggtatt cattccccgt cgagggtgtt tcgtgaccag gttggccggc    10980
aggttgttgc cggtttggct gagggtatta ctggtaatgc tggtttggcg ttggatgcga    11040
tgtctgatat ggcgggacgg ctgcctgatg cggttgatgc ccggtttggt gtgcgatcgt    11100
ctgtgggctc gtttaccccg tatggcaggt atcagcgtgc gaatgataag agtgttgtgg    11160
tgaatgtgaa tggacccacg tatggtgatc ctaacgagtt tgcgaagcgg attgagcggc    11220
agcagcgtga cgctttgaat gcgttggctt acgcgtgatt gggggtgttg ttcatgtttc    11280
ttcctgaccc gtctgatcgt tctggtttga ctgtgacgtg gttgatggat ccgctgtttg    11340
gtggggagcg tgtgcttcat ttgacggatt atacgggtgc gtctcctgtc atgttgttga    11400
atgattcgtt gcgcggtttg ggtgttcccg aggtggagca tttttctcaa actcatgttg    11460
gggtgcacgg ctcggagtgg cgcgggttta atgtgaagcc tcgcgaggtg acgctgcctg    11520
tgttggtgtc gggtgttgac ccggatccgg atggcgggtt tcgtgacggt ttttgaaag    11580
cctatgacga gttgtggtct gcgtttcccc cggggggagga gggcgagttg tcggtgaaga    11640
ctcctgccgg ccgtgagcgt gtgctaaaat gcaggtttga ttcggtggat gacacgttta    11700
ctgttgatcc ggtgaatcgc ggctatgccc gctatgtgat tcatttgaca gcttatgacc    11760
cgttttggta tggggatgag caaaagtttc gttttagtaa cgcgaagttg caggattggt    11820
tgggtggcgg ccctgtcggc aaggatggta ccgcgtttcc tgtggtgttg acgcctggtg    11880
ttggttcggg ttgggataat ctgtctaata agggtgatgt gcctgcgtgg cctgtgattc    11940
gtgttgaggg cccgttagag tcgtggtctg tgcagattga tggtttgcgt gtgtcttcgg    12000
attatcctgt cgaggagtat gattggatca ctattgatac ggatcctcgt aaacagtctg    12060
cgttgttgaa tgggtttgag gatgtgatgg atcgtttgaa ggagtgggag tttgcgccta    12120
tcccgcctgg cggttctaag agtgtgaata ttgagatggt gggtttgggt gccattgttg    12180
tgtcggtgca gtacaggttt ttgagggctt ggtgaatagt tgatggctgg tcttgttccg    12240
catgtaacat tgtttacgcc ggattatcgt cgtgtggcgc ctatcaattt ttttgagtcg    12300
ttgaagttgt cgttgaagtg aatggtttg tctacgctgg agttggtggt gtcggggat     12360
cattcaaggc ttgacgggtt gactaagccg gtgcacggc tggttgttga ttatggtggt     12420
ggccagattt tttctgggcc tgtgcgtaag gttcatggtg tgggtccttg gcgttcttcg    12480
cgggtgacta tcacgtgtga ggatgatatt cgcctgttgt ggcgtatgct gatgtggcct    12540
gtgaattatc gtcctggttt ggtcggtatg gagtggcgtg ccgacaggga ttatgcccac    12600
tattcgggtg cggcggagtc ggttgctaag caggtgttgg gggataatgc ttggcgtttt    12660
ccgcctggtt tgtttatgac cgatgatgag agtcgtggcc gctatattaa ggatttttcag   12720
gtgcggtttc acgtgtttgc cgataaattg ttgccggtgt tgtcgtgggc tcggatgact    12780
gtcacggtga accagtttga gaatgcgaag tttgatcagc gtggtttagt gtttgattgc    12840
gtgcctgctg tgacgcgtag tcacgtgttg actgccgagt ctggttcgat tgtgtcgtgg    12900
gagtatgtgc gtgacgcccc gaaggcgaca tctgtggtgg ttggtggccg cggcgagggc    12960
aaggatcggc tgttttgcga ggatgttgat tcgatggccg aggggattg gtttgatcgt    13020
gtcgaggtgt ttaaggatgc ccgtaacacg gattctgagc atgtgcatct cattgatgag    13080
gctgagcagg tgctgtccga gttaggggct acttcggggt ttaagatcga gttggctgag    13140
tcggatgtgt tgcggtttgg gccaggcaat ctgatgccgg gtgatttgat ctatgtggat    13200
gtgggttctg ggcctattgc ggaaattgtt cggcagattg atgtgagtg tgtatcgcct    13260
ggtgatggtt ggacaaaggt gacaccggtt gcgggtgatt atgaggataa tccgtcggcc    13320
```

```
ctgttggctc gccgtgttgc cggtttggct gcgggtgtgc gggatttgca aaagttttag   13380
taagtgattg gggtttgttg tgggtattgt gtgtaaaggg tttgatggtg tgttgaccga   13440
gtatgattgg gctcaaatgt ctggtctgat gggtaatatg ccgtctgtga aagggcagga   13500
cgattttcgt gtcggcacta cggttcaggg tgccacagtg ttgtgtgagg tgttgcctgg   13560
gcaggcttgg gctcacgggg tgatgtgcac gtcgaatagt gttgagacgg tgacggggca   13620
gctgcctggt tctggcgaga cccgctacga ctatgtggtg ttgtctcggg attgggagca   13680
gaacacagcc aggttggaga ttgttcctgg ggggcgtgcg gagcgtgccc gtgacgtgtt   13740
aagggctgag cctggcgtgt ttcatcagca gttgttggct actttggtgg tgtcgtctaa   13800
cgggttgcag cagcagttgg ataggcgtgc tatagcggcc cgtgtggcgt ttggggagtc   13860
tgctgcgtgt gatcctaccc ctgtggaggg tgaccgggtg atggttcctt ctggtgctgt   13920
gtgggctaat catgcgggcg agtggatgtt gttgtctccg cgtatcgaga cgggttctaa   13980
gtcgatcatg tttggcggat ctgctgtgta tgcttacacg attccgtttg atcgccagtt   14040
tagtagtccg cctgttgtgg tggcgtctat ggctacggcg gctgggggta cgcagcagat   14100
cgatgtgaaa gcctacaata ttactaataa ggattttat ttagcgttta ttacgaatga   14160
tagttcgaag ccttctggtg tgcctgcggt ggctaactgg attgctgtcg gcgtgtaatg   14220
tgcggcctgc aggtatgtga cgtgttgtgg tggtttgtagt ggtaggggc tgtagtgtca   14280
tggtttacac ctgcactggt ggcctctatc tgtaccgcgt tggccacggt tttgggttct   14340
gttcaggcgg tcacgtctaa atctcggagg cgtttgcggc ggctgtcggc tcaggtggat   14400
gcgatggaag agtatacgtg gggtgtgcgg cgcgaggtgc gaaggtttaa cgccgggctt   14460
cctgatgatg tggagcctat gcatctccct gatgtgcccg agttttgaa agatactgtt   14520
gatggtggag gtgagtaggg ttgagggagt tggaggagga gaagcggcag cgccgcaatt   14580
ttgagaaggc ttcactggtg ttgttgtttt tgtcgcttgt gttgttggcg gtggttgctg   14640
cgggtgcttt gcgtttcggt gctgtatcct ctgagcggga ttcggagcag gctagggccc   14700
agtcgaatgg tacagcggct cggggttag ccagccgtgt gaagtgggtg tgtgcttcgg   14760
gtggggtgga gtctgcgcgg cttcaccgtt ctggtttgtg tgtggatgct gtgcgtgttg   14820
agcagcgtgt tcagggtgtg ccgggcccgg ctggtgagcg cggcccgcaa ggccctgcag   14880
gtgctgacgg ccgggatggt gttaatggtt cggctgggct ggtgggccct gttggtccgc   14940
agggctctcc cggtttgaat ggtgtgaaag gtcctgacgg gttgcctggc gcgaatggat   15000
cggatggcca tgatggtgtt ccaggtcgtg caggtgctga cggtgtgaac ggggttgacg   15060
gcgctgatgg tcgggatggt gttaatggtt cggctggtga gcgcggtgat gtgggccctt   15120
caggtcctgc cggccctcaa ggtgcacagg gtgaacgggg tcctgctggc cctgttggtc   15180
cgcagggttc tgccggtgcc gatggcacga atggtaaaga cggtaaggat gggcgctcgg   15240
tggtgtctgt gtactgttcc gggggtcgcc tggttgtgaa atatggtgac ggtgtggctt   15300
ctaccatatc gggttcggta gcctgcgaga gtgtgaaacc gtcacctata gtgactatat   15360
catcccacaa atagaaagga gtggctgtga tggtagtgtt tggtggtgac atgttgtgag   15420
gtttattcct gctgcgcatc actcggccgg ttcgaatagt ccggtgaacc gggttgtgat   15480
tcatgcaaca tgcccggatg tgggggtttcc gtccgcttcg cgtaaaggac gggcggtgtc   15540
tacagcgaac tatttcgcgt ccccatcgtc gggcggttcg gcgcattacg tttgcgatat   15600
tggggagacg gtgcagtgcc tgtcagaggg gactattggg tggcatgccc cgccgaatcc   15660
```

```
gcatagtttg ggtatagaga tttgcgcgga tgggggttcg cacgcctcgt tccgtgtgcc    15720 gggcatgct tacacgaggg agcagtggct tgatcctcgc gtgtggcctg cggtggagcg    15780
tgccgccatc ctgtgtagac gtttgtgtga caaatataat gttccaaaga ggaagcttag    15840
tgcagccgat ttgaaggctg gcaggcgggg tgtgtgtggc catgtggatg ttacggatgc    15900
atggcaccag tcggatcacg atgatccggg gccgtggttt ccgtgggaca ggtttatggc    15960
cgtcgtgaac ggcggcagtg gagagagtga ggagttaacg gtggctgatg tacaagcgtt    16020
acataatcag attaaacaat tgtctgccca gcttactggt tcggtgaata agctgcacca    16080
tgatgttggt gtggtgcagg tgcagaatgg tgatttgggt aaacgtgtgg atgccctgtc    16140
gtgggtgaag aacccggtga cggggaagct gtggcgtact aaggatgctt tgtggagtgt    16200
ctggtattac gtgctggagt gtcgcagccg aatagacagg ctcgagtcta ctgttaacgg    16260
tttgaaaaag tgatggtggt ttgttgtggg taaacagttt tggttgggcc tgctggagcg    16320
tgccctgaaa acttttattc aaacgtttgt tgctgtgttg ggtgtgacgg cgggtgtcac    16380
gtatactgcg gagtcgtttc gcggtttgcc gtgggagtct gccctgataa cagccacggt    16440
tgctgcaata ctgtcgattg ctacatcgtt tggtaatccg tcgtttgtgg ccggcaagtc    16500
gaaggtgacg cctgttgatg ctgggcttgt tccacccgcc gatacgggca tggttgagcc    16560
gcacatggtt gatgtgttgg atcctggcat gatcgagccg atggatgatg ctgatcttgg    16620
tggctatgtg ccgaggcgtg ccgccgagtc ggaggttggc acggtagagt ctactgttgc    16680
ataattgaat atgtgtgtgc cccagcggtg ctgccacgat cgtgtggtgg ttgccgctgg    16740
ggcacaattt ttgtgttcta cagtattcta tgattcgttg ttgtctatag tttcttcgag    16800
catctgatac aggtggaggc aggcggagat agtatcgttg gcctggtcta gaacgttctg    16860
gccgataaca ttttttgtggt tgtcgcggtg gcagatgata daccgcatga tatcgtcggc    16920
cgccgattgc agtagtttgg tttggtatgc gattccggcg agccaatcta tggcttcctg    16980
gcttgcccgt gtgtcgtctg gcatgccacg ggtgttgctg ttgtttgtgg ggtatcctgc    17040
actgtcgcag taccacaaga tttcgctgca ctcgtctagc gtgtcctggt cgatagccag    17100
atcgtcgagg ctgacttctt tgacggtaag gttcacgttg tcgagtgaga ttggtacacg    17160
gtactggttt tcgacaccgc caacaatgtt ttctagctgt tgcatgttgg tgggctgttg    17220
ttggatgatt cggtgtaccg ctgttttgag ggcagtgtag ggggtatttt tgtgtgttgtt   17280 catggtttta tcccatccct gtgctgtcgt cgttgccgtc tggatagtat ctactgtttg    17340
cgtagcctgt tagggtgatg agtgtttggt ctgcccactg tttcactgtt tgtcttgtca    17400
ccccgagtcg ttgggctgcc accgaatagg tttgatcata cccgtatact tccctgaatg    17460
cggcaagccg tgctagccgt tttcgctgtt tggatggctg gcaggtgagg gtgtagtcgt    17520
cgatggccag ttgtagatcg atcatggaga cgatgttgtt gccgtggtgt tgtggcgcgg    17580 ttggtgggg tggcatgccc ggctctacac tcggtttcca tggtccgccg ttccagatcc    17640
attgggcggc ttggatgatg tcggcggtgg tgtaggtttg gttcactggt cacccccttga   17700 acaggttgtc gaggttgtct gggttgctgg tgttagtggt gtcgaatcgt ccgacgcagt    17760
ggcagtagtc gtacatgagt ttgataatgt gttggtggtc tcccaaatag gtgttgccgc    17820
tgatgctgta ggtggctgtg ccgtctttac taataatgta ttttgcggtg atggtttcgg    17880
gtgtttcggt gttggtgatg atggctgtgg tggtggcgcc tacggtttgt agcctggtgg    17940
tttgggttcc gtcgtcgagg atggtagtaa ccatgagggt tgtcctttag atgctggttt    18000
ggttgtcggc tagatgaata atatcggata aaggtttcgg ctggtctagg tgttgtatgg    18060
```

```
ttttgttggc tagccgtttg gctaccctgt aacacatttt ggtatagtgt ttgttgtcta   18120
ggttgtggta ttgttcccgc accgcaatat atagtaggga gtcttggtac aggtcgtctg   18180
cactgattgc ggggtagtgt ccggctgttt tggtgcatgc ccggttgagt gtgcggagat   18240
gatggcctgt ggcccatccc cacgatgcgg tggcggccag gtcggctttt gttggtcgtc   18300
tactcatggc actatttcat ctcgctatct ggtagttgtt tggtgttttg ttgttgatag   18360
tgtagcacac gagtccgggg tggccggtgg tgcctgtgcg gtgccggaac catgtggatt   18420
cgccttccat ggatgggcat tggatgaagg tgcgttgtcc ttgctcggag atttcgaggt   18480
ggtgccggtg cccggccatc agaatattag atacggtgcc gttgtggaat tcttggccgc   18540
gccaccattc gtagtgttgg ttgttgcgcc attggtgtcc gtgggcgtgc aggatttgtg   18600
tgccggccac attgacggtg gtggtcattt cgtccctgtc agggaagtgg aagtgtaggt   18660
tggggtagtt gttggtgagc tggtaggctt ctgcgatggc gcggcagcag tccacgtcga   18720
aggagtcgtc gtaggtggtg acgcctttac cgaatcttac ggcttcgccg tggttgccgg   18780
ggatggatgt gactgtcaca ttttggcagt ggtcgaatat gtggactaac tggagcatgg   18840
ccatgcgggt gagcctgatt tgttccgtca agggtgtttg ggtgcgccag gcgttgttgc   18900
cgccttgtga cacgtatcct tcgatcatgt cgccaaggaa tgcgatgtgg actcgttgcg   18960
gctgtcctgc ttgccaccag tagtgtttgg cggatgtgag ggagtgcaaa tagtcgtcgg   19020
cgaagtgtgc tgtttctcct ccggggatgc ctttgccgat ttggaagtct cctgccccga   19080
tgacgaaggc tgcagtgctg tagtcggtgt gggtgtcttg ttcgggtttt ggtggctgcc   19140
attcggctag tttatcgacg agttcgtcta cagggtaggg gtcggttgta ggctggtggt   19200
cgatgatttt ttgtatggat cggccggttt ctccgttcgg taaggtccat tcggagatgc   19260
gtgtgcggcg cacggtgccg ttggctatgt tgtcgtcgat ggtgtcgatg gcgttgtcgt   19320
ggttggctag ctgggtgagg agccggtcta tgttgtctat catcgggtat cctcctcttg   19380
ttgctgggtg gtgttggctt gtttgcggcg atagtctttg atgacggtgg cggagatggg   19440
gtatcctgcc tgggtgagtt gttttgctag ccatgaggcg gggatggttt tgtcggcgag   19500
gacatctgcg gctttgttgc cgtagcgttg aatgagtgtt tcagttttgg ttgccatgat   19560
gtcctagggg ttgtgtggtg ggctgccatc ctgtgcggca gtcgccgtcg tgtcctggtt   19620
tgcgtgtgca ccacgatacg gttccgtctg tgtggttgag tgttttgccg cacatgatgt   19680
cacgtaggtg ctcgggaaac ttatcgttgt tgttgtcccc gtgcgtgtcg atcaagtgtt   19740
gggttttggc gaccatcatg tttcctatgt gtgaaagagt gtgcaaatac tatgcaggtc   19800
tcatgggtgt ttatgcgggt atggttttca tcaccttgct gaacgtcacc tggttactgt   19860
acatcatctg ggtgatttcc tgatccgttt tgtcggggtg ctgctttcgc aggttcgccc   19920
actggcaggc gttgtcggtt tcctgctgta aacgtgtcag gtgctgctct gcgatgatgt   19980
gtttccacat ggtccatgat atgtcgagcc gtttgagcat gtcgatggct ggcacgttga   20040
acgagttgag gaagagtatt tcttcggtgt agtactgttt ttcgtattgg tcccatccgc   20100
ttcggtgcct gttgggctgg ttttggggt aggcttcccg gcagattttg tgtaaccgtt   20160
tggccatgtc gtcgggtagc ttgatgtcgg ggttggcgcg gatcatggat cgcatcccgt   20220
cgtaggtggt gccccaggtg tgcatgatgt ggagtgggtc ttcaccatca gcccattttt   20280
ctgcacagat ggcgaggcgg atgcgcctcc tggcggcctt agaggtgtcg ctgcggccgg   20340
ggatggggca ggtgtcgagg ggatccatga tgctttagtg tacctttctt ggtttcgtgt   20400
```

```
tgttgtctgg ttttattgta gcactgtgtt gagtgcttgt gtcaaccctg ttttgccggt    20460
tttcaggtag gtgtctgtga catccccgac agtgaggggc acgtgggtgg cttggggggag   20520
tgctacctgg agggtttggg ccatctggtc tcccgctttg tctgggtcgg accagatgta    20580
gatgtggtcg tagccttcga agaatttggt ccagaaggtt tgccacgagg tggcgccggg    20640
tagtgctacg gccgaccatc cgcattgttc gaggatcatg gagtcgaatt cgccttcgca    20700
aatgtgcatt tcggctgccg ggtttgctag ggcggccatg ttgtagatgg agcctgtgtc    20760
tcctgccggg gttaggtatt tggggtggtt gtgggttttg cagtcgtgcg ggagtgagca    20820
gcggaaacgc attttcgta tttctgctgg cccttcccat gtgggtaca tgtaggggat      20880
ggtgatgcac tggttgtagt tttcgtggcc gggtatgggg tcattgtcga tgtatccaag    20940
gtggtggtag cgggctgttt cttcgctgat gcctcttgct gagagcaggt cgagtatgtt    21000
ttcgaggtgg gtttcgtaga gggctgaggc tttctggatt cggcggcgtt ccgcaatgtt    21060
gtatgggcgt atgctgtcgt acattcgggt tttctttctc taatcgttgt tgtagcttgg    21120
cgagtccgcc tccgacaccg catgtgtggc agtaccagac gcccttgtcg aggttgatgc    21180
tcatggaggg ctggtggtcg tcgtggaacg ggcagaggat gtgttgctcg ttcctggacg    21240
ggttgtaccg tatccggtag gtgtcgagga ggcggcaggt atcagaggtg tgggaggagc    21300
tcgttgaggg ttgataccac ataggcttcg ctccatggct tgttgcgctg tttcatcact    21360
acgagtccga tagtggactg gctttctcgg ttgcggtgtg tttcgtagtt gcgtgcctcc    21420
cggctggctt gtttcacgaa ttgggctagg tgtggctggc cagctttcgc ctcgatcacg    21480
tatgtgtggt ttttggtttt gaggatgagg tcgccttcgt cttcgcggcc gttgaggtgg    21540
aggcgttcta tatcatgacc ggtgtcgcgt agctggtgga ggagtcgtgt ttcccattct    21600
gcgcctgccc tgcggttgcg tgcctgttgt gttggcatga tagtcctttg tgtgttgggg    21660
tcatgttcca tggctgtttt tcggcgaggg gtccgaagaa tgtgtattcg gggtaggctc    21720
gtagccgttc gtattgggtg ccgtcggggc tggatttgcc tgtgcgctgt ttcaacactg    21780
cgatgcgtgc ctctgccggg atcgataggc cgttgccgtt atcctcgcca ccatacaggg    21840
agactccgag gatgagttgt ggttttcgg agaggccgtt tttgatttct cgccgggcgg    21900
gcgggtgttc gatgtcggag ccggttttgt cggttgcgtg gtgtgtgaca ataatggtgg    21960
agtccgtgtc cctgcccaat gctgtgatcc attgcatggc ttcttgctgg gcctggtagt    22020
cactctcgca gtcttgtatg tccatcaggt tgtcgataac aatgagtggt ggaaaggtgt    22080
tccacatttc catgtaggct tgcagttcca tggtgatgtc tgtccatgtg atgggtgact    22140
ggaatgagaa tgtgatgtgc gcgccgtggt ggatgctgtc tcgatagtat tctggcccgt    22200
agtcgtcgat gttttgttgt atctgtgcgg tggtgtgttg ggtgttgagt gagatgattc    22260
gtgtggaggc ctcccagggt gtcatgtccc ctgatatgta gagggcgggc tggttgagca    22320
tcgctgtgat gaacatggct agcccggatt tttggctgcc ggagcgcccc gcaatcatga    22380
cgagatcccc tttgtggatg tgcatgtcca ggttgcggta gaggggttct agttgtggta    22440
tgcggggcag ctcggctgcg gtttgggagg ctctctcgaa ggatcgttgt agagagagca    22500
tcggagcctt aatctatctg tttgttggat gtgtattggt ggtcagatgg agtcgatgtc    22560
tacatcatca ctaccagtgg tgttgggctg gctgtctcgc cggtcaacgt aggctgctac    22620
gaggtcgtag atggcgtcgt cgagggggttt gagcacgacc gcgttgaagc cgttttttggt  22680
gcgcacggtg gctagtttga aggcctgctc ctcgccaagg tatgcttcta ggtcgcggat    22740
catggagtgt gggcggtcgt tgttgccgcg tgctttctca ataatagcgt tggggatggt    22800
```

```
ttctggggtg ccgttgttga gatcgtctag ggtgtggaag atggtgacat cagcgtagat   22860
gcgatcggcg gtctgtccgc cgtagccttc ggtgttgtgc tggacgtcgt ggactttgaa   22920
ggcgatggcg gtggcgtcct ggtttcggga ggggttgaag aaggtgctgt tgctgttgtt   22980
gcggtagttg gcgagtccca ttgttgtttc ctttactgtt tgtgttgttt tgtttgtcgg   23040
ttttatcggg tgaggctgtt tcgtttcgtg cggaaggctt cggatacgtc actgttactg   23100
gtgatggtct ttttgtactg tttgagaagg tcggctagct gtgctttgct tgtggcattg   23160
ttgattttgt cgatgatggt gttgtttcct tctgatgcga tgttgtctac gtagtctttg   23220
gcggcctggt tgtatcggtc ttggaggatg atggatgctg tggcgatcag tgttgccagg   23280
tcccagttcc ttgccgccga actgtttttg agtccgccta acaggtcgat gatagtcttc   23340
ttcacctggt cggcggtgtc tcccctaatg acggtccatg gggcggcgta gtctccgccg   23400
tatttgaggg tgacggtgaa tcggtcgtcg tctgtgttgt cggtcactgg tgctccttgc   23460
cttcttctgt tggggctgtg atggtggttt ctatagggta cctgtaggcg tctttcccgt   23520
ctacagccca acaggcgtcc ttgacggggc atcctttaca gagtgctgtg acgtgggta   23580
cgaagatgcc ttcgctgatt cctttcattg cttgactata catggatgat acatgccggt   23640
aggtgttgtt gtcaaggtcg tacagttcgg tggatgtgcc ttgtcgggg acttgtcgt    23700
cgttgcggct ggtggctggc gtccaaaaca tgcctttcgt gacatggatg tcgtgttggt   23760
tgagcatgta ccggtaggtg tgcagctgca tgctgtcggc gggtaggcgt ccggttttga   23820
ggtcgaggat gaaggtttcg ccggtgtcgg tgttggtgaa gattcggtcg atgtagccga   23880
cgatctgggc gccgtcgggg agggtggttt ctaccgggta ttcgatgcct ggctggccgt   23940
ccagaattgc ggtgatgtat tctggtggt tgcgcctcca gttttccac cggtccacaa     24000
aggtggggcc gtaaaccatc caccaattgt agtcttttt gtgtggcccg cctgactcgc    24060
acatgttttt gcatattctg ccggagggtt tgatttctgt gccttcggat tcggcgaggg   24120
cgatttgggt gtcgaaaatg ttttttgaagg atgagagttt gtcgggcagt gcagggtatt   24180
cggcgggatt gtacaggtgt aggtcgtatt gttcggtgat gtggtgtatg gcgcttccgg   24240
cgatggtggc ataccaggtg tggtgttggg catggtagcc gtgttggagg cgccattttt   24300
ctccgcattc ggcccactgg gtgagtgaac tgtaggagat gtggcctgga tggttgatgg   24360
ttttcgggta ttgtgctagg ggcattactt gtcgcttttg ttccatgggt tgcgggtgtc   24420
ttggccggcg tggtgttgct ggtatgcgag gagtgcgagg cagtgccagg cggcgtgtgc   24480
cagatgcggc aaatgtgatt cgtggtcgag gttgttgcct tgctgccatg atagtaggtg   24540
cctgtagagg gcgtcgacac tgtggctcca cgggtatcct ccggtccagt tgttgtcgcc   24600
gtatttggtg gcgccgtagc ctgctacttc gcctagggcg tgaagggatg ctgggtcgat   24660
gagggatagc ctgcattgtt tgagttcttt tcgggcaccg ctgttcgggt cggtgtacat   24720
gcgggtgggc tcatccatgg ggtgtgtgct ccttaagggt gggttactgg ttgttatcgt   24780
gggctagggc gacggcgaga ataatgatgg cgagggtttc tgcgatcagt atgggtgttg   24840
tgatcattta gtgtctcggg gattgttggt gagggttgag gcgcctagga gggtggcgag   24900
ggcgcatgcg gcgatgatgg cgagggctgc cttgtgtggg gtgccggtgg cgtacatcca   24960
tgtgatgatg ccgccttgga tccaggctag gctggtgaag aacgtttcgt aactgtgcag   25020
ctcaatgttg ttgttgggtg tgttcatgct tgctcctgaa gaatggtgtt gatggtttta   25080
taaatgttgt acaggtcggt ttcgatagat aacagttggt tgatttggtg gtcgagatca   25140
```

```
atgtctgggt tgagggtgtt gatgcgggag gcgatatcgg tggctgtgcg tagtgtgccg   25200
ccggtgtggt gaatgatgtg tgccgtgtcg gctagtccgg tggtgacggc gtagtgggag   25260
aggagaggca tagcagggat gctccttgac gggttactgt tgcgggttga tgttgaggtc   25320
ggtgacgtgc gggtggtctt ctgttccggt gacgaggcag tggacggtga ctgggagttt   25380
ggatgcgccg ggctgtttca tggttgcacc gtagacgatg gagaaggtgt ctttaccgat   25440
ggttttgtgg agttggaggt cgatgtcggg gttgccgttc cagttgacac cgtgtgcggc   25500
ggcctgttgt tcggctttgc ggttgcaggt gtgtgccgcg gtgatcatgg tgagtccggt   25560
ggcggtttct tcaccccgtg tttgggcttg cttgtgggtt ttggtctgct cggcttgtag   25620
ggagcgggtg gcggctgcct gacgtgccgc tttctcggct ttgcgctgtt ggacggtttt   25680
gggggtccat tcggtgttgg ctgttgtggc ctgtggggct ggctgtgagg cgagtggcgg   25740
attgtcgtct ggggctggca tgaaggaggc tgcggcgatg atggcggctg tgatgcctgc   25800
gatggtgtag cctttcttct tgttcatggc tgttgtcccc tttccggggt gttgttcgtt   25860
gctgacatga tcaatacttc cagtgactgg accgcgtgtc aaggctgcgc tcaacgattg   25920
tgagcgatcc ttgtgtggct aggggtttta tcgggcacac agggtgagta gatggccaac   25980
attgatgcgc ctcacattcc agtagagttg tgtggcttca ccgccggtga gcggcttcca   26040
ctcgtcgtgg ctgaacacgg tgccatcggt ggcgatgaat gtgtttgggc gtagtttgtg   26100
aagttcggct tccacgctct gccggtaggc ttcggcgagg ccttcaaaat ccatgtggtc   26160
gcagtggagg ttttcgaggc gtgtcaggtc gaagggtgtg gggcagtcgt agctggtggg   26220
ggtgtagagc tgggtgaagt ggttggcgat cttttgcatc atgattcctt ttctggtgat   26280
ggtgtgttga ggatttatcg ggtggatgcg acaaggatgg cgtctatgtc gatcatgtcg   26340
atgagatcgt ggagttcctc ggcttcattc tcggtgagcg gctgccagtc gtagtccccg   26400
tatagggcgc cgtcgagggt gacagtccac agtggccgga tgagtcgtat ggcttcttgt   26460
actttagcgt ggtacatgcg gcgcaccata tcgagatcga tgtcgtctga atggtttccg   26520
gtgaggctgt ggaggctgag cgggtctatt tctgtctgcc tgtagaggga tgtgaaggat   26580
ggggtgatga gtgtgccatc catgggtgat gttcctttct ggattgtctt ggttggttgt   26640
tgtggttttt atggtgtgag ggttgtgatc catagtcaag gctgcgctca ttcggtttga   26700
gcgtttcata tgggtgtggc atggggtgtg gcgtatctca cttaagccct tatggcctct   26760
ctcggcgtct caaatcttct aggggtagga ttatataggg ttgaccctgc tgatcgattc   26820
tagggccctt ctagggcgtc tcagaggtat gtctgagtga tagcaggtcc ggtagatgac   26880
ccggcagatc tgccttggct ttcatcgcgg gggtcgaggt gccagatctg gcatggaat   26940
ctacaccctc ataccgtgtg agataggcca cactcgcctc gtatggtgtg cacccccaag   27000
gccactctgc caatctggcg tggagggtgt agcccagaaa tgccgtttaa agcctcaggg   27060
atacgcctag gagcgccttg cggggtgggg gctaggtatt tatacccca gcacattctg   27120
atcgattcta gacgccccac agagcctgat acacgatcaa ccatcccagc atagatcacc   27180
agccctatc ctgcttagct aagcctcaac tatgtggaca gtgtgggata ctgtggggga   27240
agaaggacac ggtaaaaaga aggggggcat cagccttcac acctgaggta cttaagttaa   27300
ccttagggtc ttagcgctga gcatttagca ccgagcccct caagggctcg gcataagccc   27360
gagcaggctc agccgatcag gcacagccct gaaaggggta cacgccatca gggaaggctt   27420
gagagtacga ggagccttag cgacgagtac tcgaaagcct gagggaacac cctcagcact   27480
gatgggccta gcgtgttcgg aaaggacaca agagtacagt gtgacagctg tccgggagtg   27540
```

```
aaacccgttc tgactagggg tttcagcctt aacaaccctc aaaggttaca agactctaag    27600
aaaatttaag gaaaagttta ggtttaattt ttggaccttc actaccaaaa acacccgttt    27660
acacccatca aacccgccta tagagccaaa tccaccagtt tgactcatcc caggtggggt    27720
atgataggct ggacaggtag ccagctggac gcaaggccga aatccgctga cgcggctttc    27780
acccttacat ccatcagtct accaaacact ttaaagcttc aagggcttag cgctaagcac    27840
cgagcccctc aagggctcgg catcagtctt aaagccttaa acacttaaag tacatataaa    27900
accttaacag ttaaacgtta aaagctttaa accttaacac ctaagttaag tataaaacct    27960
taaggcttta gcacttaagg atataaactt aacatcagtg tttaagactt taaaacttaa    28020
aataactatt aagactttaa aaaccttaag tacttaaagt taaccatcag tcttaaactt    28080
taatattata acctataagt cttaaagctt ataggtatta tattataata taagtattaa    28140
agcttataag ttataaaagt tttagaagag ctaagaggtt aacttcttta cttctctact    28200
ctctttggta cttctctcct tctcttcttt tcttcatcag gggagaagag gaaccttta    28260
ccgtgtgact cgtgtgcttc tggtcgcaag ttcccatcgc acactcccca cactctgaca    28320
cccgtgtccc tttacggctt ggcgtgttcg gctgaaggcg tacggcgtgt cacgctcaca    28380
cccttaacac cagatgagac ttaaagtgta tattatatgt agaagacttt aaaaacctat    28440
aaggtgttcc tgctgagcct gtgtccttta acgctaggcg ccaagcgcta agctgtgaaa    28500
cgcgaacaca cacccacccc cattttcctt ccgtgtcctt ctcttttgac acaaccgggg    28560
ggcgatgtga tcttttttcac atgccggggg gtatgagtag aaaacaaaca ccccggcaca    28620
aacagaacac cccctcaaac aaacaaaaca gggcctagaa tcgatcggca gggcaagggt    28680
agagtatttta tacccctaga cgatcccaag cccttataga ggcaaataag acccgtacag    28740
ggctaggcga ggaacagaca catcatggca cgcaccaacc gcacagccag ccaagcccac    28800
cggcgctggc gggcaagact catcacccaa gcccgacaac aaggcaaaac cgaatgccca    28860
ctctgcggag cccagatcgc ctggggcaca cacgatctac caaccagccc cgaagccgac    28920
cacatcacac ccgtcagccg cggggggactc aacaccctcg acaacgggca aatcatctgc    28980
agaacatgca acagaagcaa aggcaacaga acacaaccaa acatcaaatt ccaacaacaa    29040
accacaaaaa ccttgattcc atggtgaaaa acccgccaac ccccaccggg cacacccct    29100
gcacacccg                                                            29109
```

<210> SEQ ID NO 6
<211> LENGTH: 855
<212> TYPE: DNA
<213> ORGANISM: Bacteriophage 103609

<400> SEQUENCE: 6

```
gtgagataca ttcctgcggc gcatcattct gccggctcga atagtccggt gaatagggtt      60
gtgattcatg cgacgtgccc ggatgtgggg tttccgtctg cctcgcgtaa agggcgggcg     120
gtgtctacag caaactattt cgcgtcccca tcgtcgggtg gttcggcgca ttatgtttgc     180
gatattagtg agactgtgca gtgccttgtcg gagtctacga ttgggtggca tgccccgccg     240
aatccgcata gtttgggtat cgagatttgc gcggatgggg gttcgcacgc ctcgttccgg     300
gtgccggggc atgcttacac tcgggagcag tggcttgatc ctagggtgtg gcctgcggtg     360
gagaaggctg ccatcctgtg tagacgtttg tgtgacaaat ataatgttcc gaagaggaag     420
cttagtgcag ccgatttgaa ggctggtagg cggggtgtgt gcggccatgt ggatgtgacg     480
```

```
gatgcgtggc atcagtcgga tcatgacgat ccggggccgt ggtttccgtg ggacaggttt      540
atggccgttg tcaacggcaa agatgagagt ggggagttaa ctgtggctga tgtgaaagcc      600
ttgcatgatc agattaaaca attgtctgct cagcttactg gttcggtgaa taagctgcac      660
catgatgttg gtgtggttca ggttcagaat ggtgatttgg gtaagcgtgt tgacgccttg      720
tcgtgggtga agaatccggt gacggggaag ctgtggcgca caaggatgc tttgtggagt        780 gtctggtatt acgtgctgga gtgtcgtagc cgtattgaca ggcttgagtc gactgtcaac      840 ggttttgaaaa agtga                                                      855

<210> SEQ ID NO 7
<211> LENGTH: 864
<212> TYPE: DNA
<213> ORGANISM: Bateriophage 103672

<400> SEQUENCE: 7
gtgaggttta ttcctgctgc gcatcattct gccggctcga atagtccggt gaatagggtt       60
gtgattcatg cgacatgccc ggatgtgggg tttccgtccg cttcccgtaa ggggcgggcg      120
gtgtctacgg cgaactattt cgcgtcccca tcggcgggcg ttctgccca ttatgtgtgc       180 gatatttcgg acggtgca gtgcttgtcg gagtctacga ttgggtggca tgccccgccg        240
aatccgcata gtttgggtat cgagatttgc gcggatgggg gttcgcacgc ctcgttccgt     300
gtgccagggc atgcttacac gagggagcag tggctggatc ctagggtgtg gcctgcggtg      360
gagaaggctg ccatcctgtg tagacgtttg tgtgacaaat ataatgttcc gaaaaggaag      420
cttagtgcag ccgatttgaa ggctggcagg cggggtgttt gcgggcatgt ggatgttacg      480
gatgcgtggc atcagtcgga tcatgacgat cctgggccgt ggtttccgtg ggacaaattt      540
atggctgtgt gaatggcca cggcggcggt tcaagtagtg aggagttaac ggtggctgat      600
gtgaaagcgt tacataatca gattaaacaa ttgtctgctc agcttactgg ttcggtgaat      660
aagctgcatc acgatgttgg tgtggttcag gtgcagaatg gtgacctggc gcgccgtgtt      720
gatgccttgt cgtgggtgaa gaatccggtg acggggaagc tgtggcgcac taaggatgcc     780
ctgtggagtt tctggtatta cgtgctggag tgtcgtagcc gtattgacag gcttgagtct    840
gctgttaacg gtttgaaaaa gtga                                            864

<210> SEQ ID NO 8
<211> LENGTH: 858
<212> TYPE: DNA
<213> ORGANISM: Bacteriophage 1894

<400> SEQUENCE: 8
gtgaggttta ttcctgctgc gcatcactcg gccggttcga atagtccggt gaaccgggtt       60
gtgattcatg caacatgccc ggatgtgggg tttccgtccg cttcgcgtaa aggacgggcg      120
gtgtctacag cgaactattt cgcgtcccca tcgtcgggcg ttcggcgca ttacgtttgc        180 gatattgggg acggtgca gtgcctgtca gaggggacta ttgggtggca tgccccgccg         240
aatccgcata gtttgggtat agagatttgc gcggatgggg gttcgcacgc ctcgttccgt      300
gtgccggggc atgcttacac gagggagcag tggcttgatc ctcgcgtgtg gcctgcggtg      360
gagcgtgccg ccatcctgtg tagacgtttg tgtgacaaat ataatgttcc aaagaggaag      420
cttagtgcag ccgatttgaa ggctggcagg cggggtgtgt gtggccatgt ggatgttacg      480
gatgcatggc accagtcgga tcacgatgat ccggggccgt ggtttccgtg ggacaggttt      540
atggccgtcg tgaacggcgg cagtggagag agtgaggagt taacggtggc tgatgtacaa      600
```

```
gcgttacata atcagattaa acaattgtct gcccagctta ctggttcggt gaataagctg      660
caccatgatg ttggtgtggt gcaggtgcag aatggtgatt tgggtaaacg tgtggatgcc      720
ctgtcgtggg tgaagaaccc ggtgacgggg aagctgtggc gtactaagga tgctttgtgg      780
agtgtctggt attacgtgct ggagtgtcgc agccgaatag acaggctcga gtctactgtt      840
aacggtttga aaaagtga                                                    858
```

<210> SEQ ID NO 9
<211> LENGTH: 40
<212> TYPE: DNA
<213> ORGANISM: Bacteriophage PA6

<400> SEQUENCE: 9

```
cttgtttgat ggttttgtag tagccgacga ggatgcgctg                             40
```

<210> SEQ ID NO 10
<211> LENGTH: 26
<212> TYPE: DNA
<213> ORGANISM: Bacteriophage PA6

<400> SEQUENCE: 10

```
agtattgtgc cgccacggcg tagcgg                                            26
```

<210> SEQ ID NO 11
<211> LENGTH: 57
<212> TYPE: DNA
<213> ORGANISM: Bacteriophage PA6

<400> SEQUENCE: 11

```
gaaggcgtcc cagcagtatt caataatgtg ttgtagtaca ctatcgggca tgtctcg          57
```

<210> SEQ ID NO 12
<211> LENGTH: 76
<212> TYPE: DNA
<213> ORGANISM: Bacteriophage PA6

<400> SEQUENCE: 12

```
ttcgtcgagc cacgcgtcga caatgatgtt gcgtatggcg cgtttgtctt tggtggtggg       60
tttgaatgcg atgctc                                                       76
```

<210> SEQ ID NO 13
<211> LENGTH: 379
<212> TYPE: DNA
<213> ORGANISM: Bacteriophage PA6

<400> SEQUENCE: 13

```
gatggcttct ttcgcccaat aggatgtgcc accgctggtc cagtatccga gtttgttgcg       60
ctgcatgccc ttggcgtcca tctcgtcgat agtgaggcac ctgcggcgat tggggcctgt      120
cttgaccccg tggtcgcctg tccggtgcat gtcgcctgag gtggtactcg tgaatgtttc      180
atggcagatg gtacagtgct ctggtcgata tccggtgatt gtgctatcgc acttgtggca      240
tgtccattcc atgattgctc ctattttcca ttataagact tcctgtagtg ccattttagc      300
gccttgcggg tcttgggggt acaactatat aggtcaggtg tttctaggcg attctaggct      360
cattgtgtgt ggctgggt                                                    379
```